(12) United States Patent
Osbourn et al.

(10) Patent No.: US 12,391,963 B2
(45) Date of Patent: Aug. 19, 2025

(54) METABOLIC ENGINEERING

(71) Applicant: PLANT BIOSCIENCE LIMITED, Norwich (GB)

(72) Inventors: Anne Osbourn, Norwich (GB); James Reed, Norwich (GB)

(73) Assignee: PLANT BIOSCIENCE LIMITED, Norwich (GB)

( * ) Notice: Subject to any disclaimer, the term of this patent is extended or adjusted under 35 U.S.C. 154(b) by 1423 days.

(21) Appl. No.: 16/762,097

(22) PCT Filed: Dec. 20, 2018

(86) PCT No.: PCT/EP2018/086430
§ 371 (c)(1),
(2) Date: May 6, 2020

(87) PCT Pub. No.: WO2019/122259
PCT Pub. Date: Jun. 27, 2019

(65) Prior Publication Data
US 2023/0279444 A1 Sep. 7, 2023

(30) Foreign Application Priority Data
Dec. 21, 2017 (GB) ...................................... 1721600

(51) Int. Cl.
| | |
|---|---|
| C12P 5/00 | (2006.01) |
| C12N 9/02 | (2006.01) |
| C12N 9/04 | (2006.01) |
| C12N 9/10 | (2006.01) |
| C12N 9/90 | (2006.01) |
| C12N 15/81 | (2006.01) |
| C12N 15/82 | (2006.01) |

(52) U.S. Cl.
CPC ............ *C12P 5/007* (2013.01); *C12N 9/0006* (2013.01); *C12N 9/0042* (2013.01); *C12N 9/0073* (2013.01); *C12N 9/1085* (2013.01); *C12N 9/90* (2013.01); *C12N 15/81* (2013.01); *C12N 15/8243* (2013.01); *C12Y 101/01034* (2013.01); *C12Y 101/01088* (2013.01); *C12Y 106/02004* (2013.01); *C12Y 205/01021* (2013.01); *C12Y 504/99039* (2013.01)

(58) Field of Classification Search
None
See application file for complete search history.

(56) References Cited

U.S. PATENT DOCUMENTS 9,994,883 B2 * 6/2018 Goossens ................ C12P 33/00

FOREIGN PATENT DOCUMENTS

| CN | 105111272 | 12/2015 |
| WO | WO 2013/167751 A1 | 11/2013 |

OTHER PUBLICATIONS

Fukushima et al. Combinatorial Biosynthesis of Legume Natural and Rare Triterpenoids in Engineered Yeast, Plant and Cell Physiology, vol. 54, No. 5, Apr. 12, 2013 (Apr. 12, 2013), pp. 740-749. (Year: 2013).*
Moses et al. Combinatorial biosynthesis of sapogenins and saponins in *Saccharomyces cerevisiae* using a C-16 hydroxylase from Bupleurum falcatum, Proceedings of the National Academy of Sciences of the United States of America, vol. 111, No. 4, Jan. 13, 2014 (Jan. 13, 2014), pp. 1634-1639. (Year: 2014).*
Ragupathi et al. Natural and synthetic saponin adjuvant QS-21 for vaccines against cancer), Expert Review of Vaccines, vol. 10, No. 4, Apr. 1, 2011 (Apr. 1, 2011), pp. 463-470. (Year: 2011).*
Meesapyodsuk et al. Saponin Biosynthesis in Saponaria vaccaria. CDNAs Encoding beta-Amyrin Synthase and a Triterpene Carboxylic Acid Glucosyltransferase, Plant Physiology, vol. 143, No. 2, Dec. 22, 2006 (Dec. 22, 2006), pp. 959-969. (Year: 2006).*
Thimmappa et al. Triterpene biosynthesis in plants. Ann. Rev. Plant Biol. 2014:65:225-57. Epub Jan. 29, 2014. (Year: 2014).*
Liang P.H. et al. Structure, mechanism and function of prenyltransferases. Eur J Biochem. Jul. 2002;269(14):3339-54. Review. (Year: 2002).*
Weeks et al. Constructing de novo biosynthetic pathways for chemical synthesis inside living cells. Biochemistry. Jun. 21, 2011;50(24):5404-18. Epub May 26, 2011. (Year: 2011).*
Matasci et al., "Data access for the 1,000 Plants (1KP) project", GigaScience, 2014, 3:17.
Anonymous: "Details for sample code #OQHZ", 2017, retrieved from the Internet: URL: https://web.archive.org/web/20170712095855/http://www.onekp.com/samples/single.php?id=0QHZ.
Anonymous: "BLAST for 1000 Plants", 2017, retrieved from the Internet: URL: https://web.archive.org/web/20170101231631/http://db.cngb.org/blast4onekp/.
Johnson et al., "Evaluating Methods for Isolating Total RNA and Predicting the Success of Sequencing Phylogenetically Diverse Plant Transcriptomes", PLOS ONE, 2012, 7(11): e50226.
DATABASE UniProt [Online], 2011, "RecName: Full=Beta-amyrin synthase; EC-5.4.99.39;", retrieved from EBI accession No. UNIPROT:Q9MB42, Database accession No. Q9MB42.

(Continued)

*Primary Examiner* — Cynthia E Collins
(74) *Attorney, Agent, or Firm* — James S. Keddie; Bozicevic, Field & Francis LLP

(57) ABSTRACT

The invention relates generally to materials and methods for biosynthesising quillaic acid in a host by expressing heterologous nucleotide sequences in the host each of which encodes a polypeptide which in combination have said QA biosynthesis activity. Example polypeptides include (i) a Beta-amyrin synthase; (ii) an enzyme capable of oxidising Beta-amyrin or an oxidised derivative thereof at the C-28 position to a carboxylic acid; (iii) an enzyme capable of oxidising Beta-amyrin or an oxidised derivative thereof at the C-16α position to an alcohol; and (iv) an enzyme capable of oxidising Beta-amyrin or an oxidised derivative thereof at the C-23 position to an aldehyde. Preferred nucleotide sequences are obtained from, or derived from, *Q. saponaria*.

24 Claims, 18 Drawing Sheets

Figure 1:
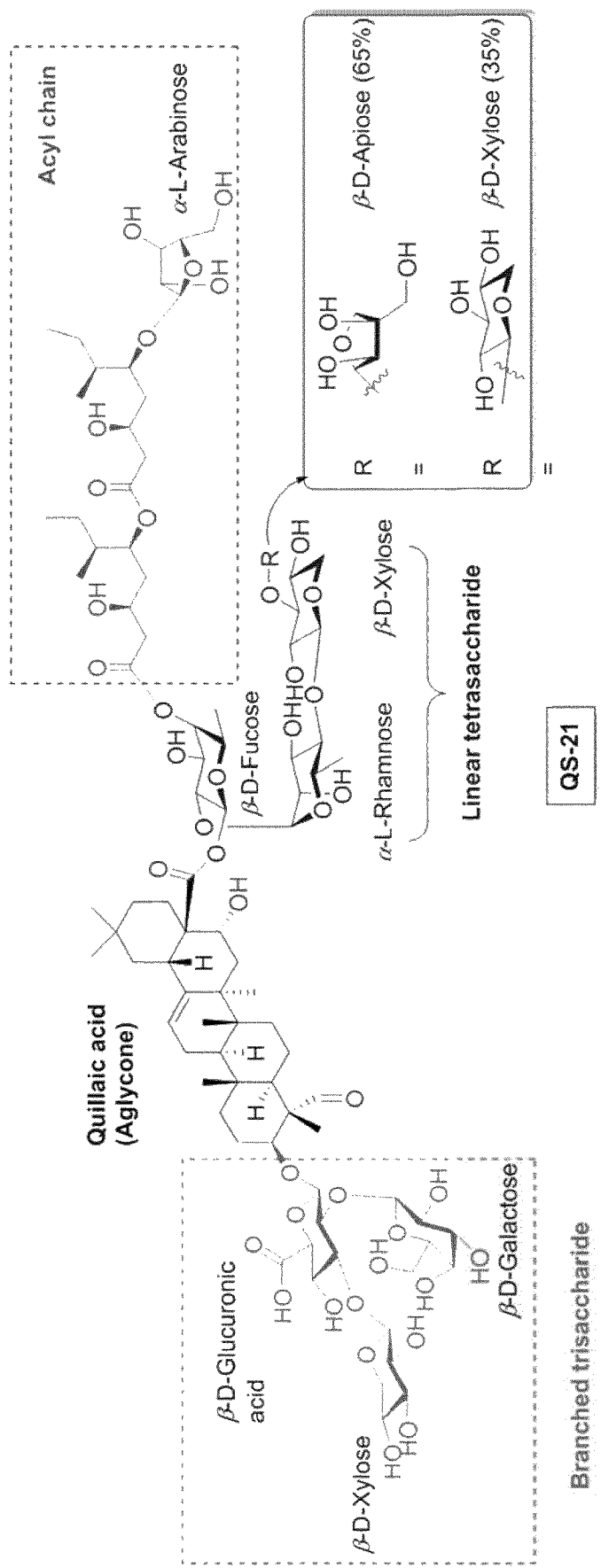

Specification includes a Sequence Listing.

(56) References Cited

OTHER PUBLICATIONS

Database NCBI Reference Sequence [Online] NCBI, 2017, "beta-amyrin 28-oxidase [Herrania umbratica]", Database accession No. XP_021278523.
Database UniProt [Online], 2017, "SubName: Full=Cytochrome P450 {ECO:0000313 | EMBL:0M066628.1};", retrieved from EBI accession No. UNIPROT:A0A1R3H8E3 Database accession No. A0A1R3H8E3 sequence.
Database NCBI Reference Sequence [Online] NCBI, 2017, "cytochrome P450 714C2-like [Momordica charantia]", Database accession No. XP_022156262.
Fukushima et al., "Combinatorial Biosynthesis of Legume Natural and Rare Triterpenoids in Engineered Yeast", Plant Cell Physiol., 2013, 54(5): 740-749.
Moses et al., "Combinatorial biosynthesis of sapogenins and saponins in *Saccharomyces cerevisiae* using a C-16a hydroxylase from Bupleurum falcatum", PNAS, 2014, 111(4): 1634-1639.
Ragupathi et al., "Natural and synthetic saponin adjuvant QS-21 for vaccines against cancer", Expert Rev Vaccines., 2011, 10(4): 463-470.
Meesapyodsuk et al., "Saponin Biosynthesis in Saponaria vaccaria. cDNAs Encoding b-Amyrin Synthase and a Triterpene Carboxylic Acid Glucosyltransferase", Plant Physiology, 2007, 143: 959-969.
Yendo et al., "Production of Plant Bioactive Triterpenoid Saponins: Elicitation Strategies and Target Genes to Improve Yields", Mol Biotechnol, 2010, 46: 94-104.
Thimmappa et al., "Triterpene Biosynthesis in Plants", Annual Review of Plant Biology, 2014, 65(1): 225-257.
Khatuntseva et al., "Triterpenoid saponins from the roots of Acanthophyllum gypsophiloides Regel", Beilstein Journal of Organic Chemistry, 2012, 8: 763-775.
Ye et al., "Synthesis and in vitro Anti-tumor Activity of Fatty Acid Derivatives of Ginsenoside Rg3", Food Science, 2013, 34(11): 45-48.
Genomic Equivalent, Terminology of Molecular Biology for Genomic Equivalent—GenScript, p. 1, https://www.genscript.com/biology-glossary/11941/genomic-equivalent [retrieved on Jun. 1, 2023].
Chemical Name Quillaic Acid, Safety Data Sheet—Version 5.0 (Original Publication Date: Jan. 7, 2016), Toronto Research Chemicals Inc., pp. 1-6.
Gholami et al., "Natural product biosynthesis in Medicago species", Nat. Prod. Rep., 2014, 31: 356-380.
Kim et al., "A Novel Multifunctional C-23 Oxidase, CYP714E19, is Involved in Asiaticoside Biosynthesis", Plant & Cell Physiology, 2018, 59(6): 1200-1213.
Li et al., "De Novo Biosynthesis of the Oleanane-Type Triterpenoids of Tunicosaponins in Yeast", ACS Synthetic Biology, 2021, 10: 1874-1881.
Zeng et al., "Chemical synthesis of quillaic acid, the aglycone of QS-21", Organic Chemistry Frontiers, 2021, 8: 748-753.

* cited by examiner

METABOLIC ENGINEERING

CROSS-REFERENCE TO RELATED APPLICATIONS

This application is a § 371 national phase of International Application No. PCT/EP2018/086430, filed on Dec. 20, 2018, which claims the benefit of United Kingdom Application No. 1721600.3, filed on Dec. 21, 2017, which applications are incorporated by reference herein.

TECHNICAL FIELD

The present invention relates generally to genes and polypeptides which have utility in engineering or modifying quillaic acid production or hydrolysis in host cells. The invention further relates to systems, methods and products employing the same.

BACKGROUND ART

Plants produce a wide variety of cyclic triterpenes, such as sterols and triterpenoids, which are the major products of the mevalonate (MVA) pathway.

QS-21 is a complex triterpenoid saponin synthesised by the Chilean tree *Quillaja saponaria* (order Fabales).

The core QS-21 triterpene backbone is quillaic acid ("QA"); this scaffold is decorated with a branched trisaccharide, present at the C-3 position and a linear tetrasaccharide at the C-28 position. The C-28 linear tetrasaccharide also features a complex arabinosylated acyl chain (FIG. 1).

QS-21 has utility as an immunostimulatory adjuvant. However the biological sources of QS-21 are limited, and due to the complexity of its structure, and that of QA, chemical synthesis is challenging.

Accordingly it can be seen that novel systems for synthesising QA, which has utility inter alia in the preparation of QS-21, would provide a contribution to the art.

DISCLOSURE OF THE INVENTION

Figure 2:
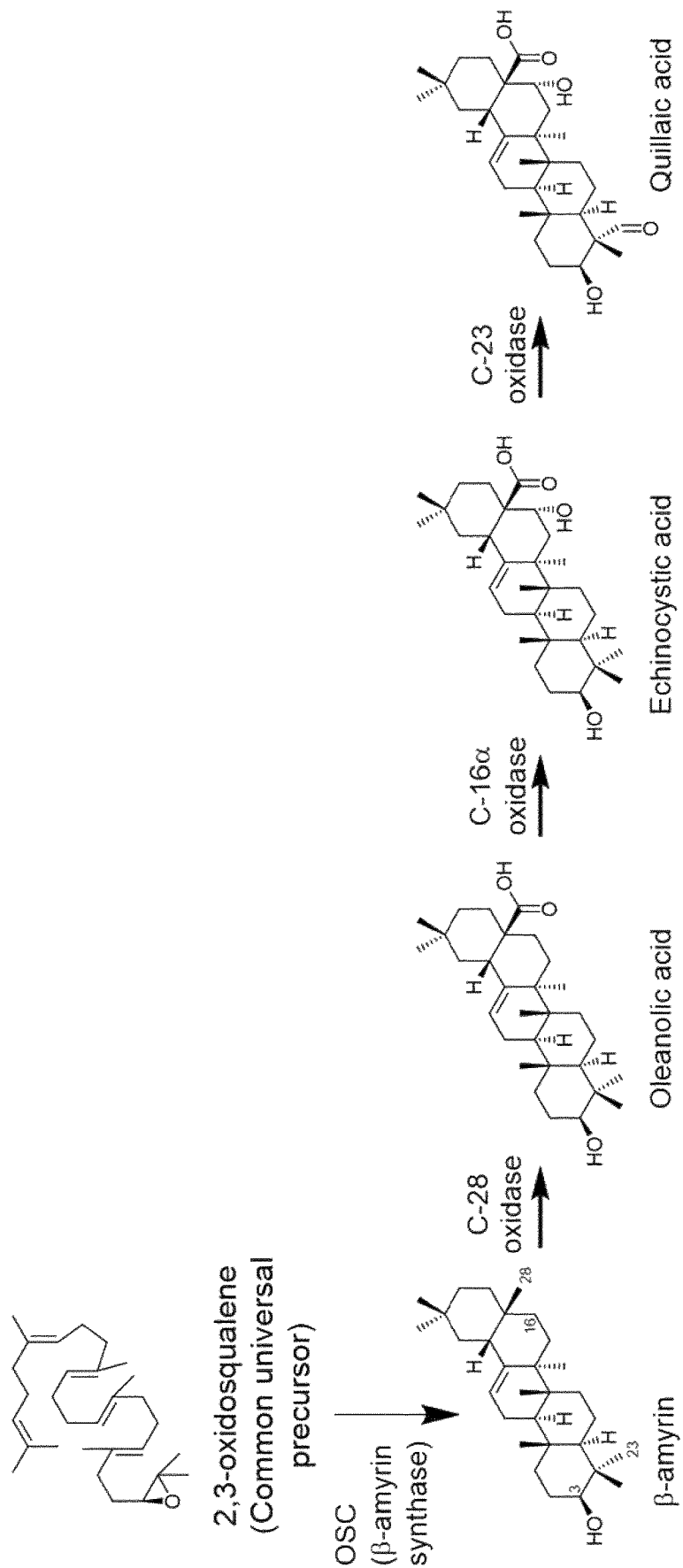

The core aglycone of QS-21 (quillaic acid) is a derivative of the simple triterpene, β-amyrin, which is in turn synthesised by cyclisation of the universal linear precursor 2,3-oxidosqualene (OS) by oxidosqualene cyclases (OSCs) (FIG. 2).

The β-amyrin scaffold is further oxidised with an alcohol, aldehyde and carboxylic acid at the C-16α, C-23 and C-28 positions, respectively, to form quillaic acid. A proposed linear biosynthetic pathway for this is given in FIG. 2, although it will understood that these oxidation reactions may occur in a different order, via different intermediates (see FIG. 11).

QA biosynthesis from OS thus includes at least four different enzymatic steps. The enzymes involved include:
- an oxidosqualene cyclase;
- an enzyme capable of oxidising β-amyrin or an oxidised derivative thereof at the C-28 position to a carboxylic acid;
- an enzyme capable of oxidising β-amyrin or an oxidised derivative thereof such as oleanolic acid at the C-16α position to an alcohol;
- an enzyme capable of oxidising β-amyrin or an oxidised derivative thereof such as echinocystic acid at the C-23 position to an aldehyde.

Figure 11:
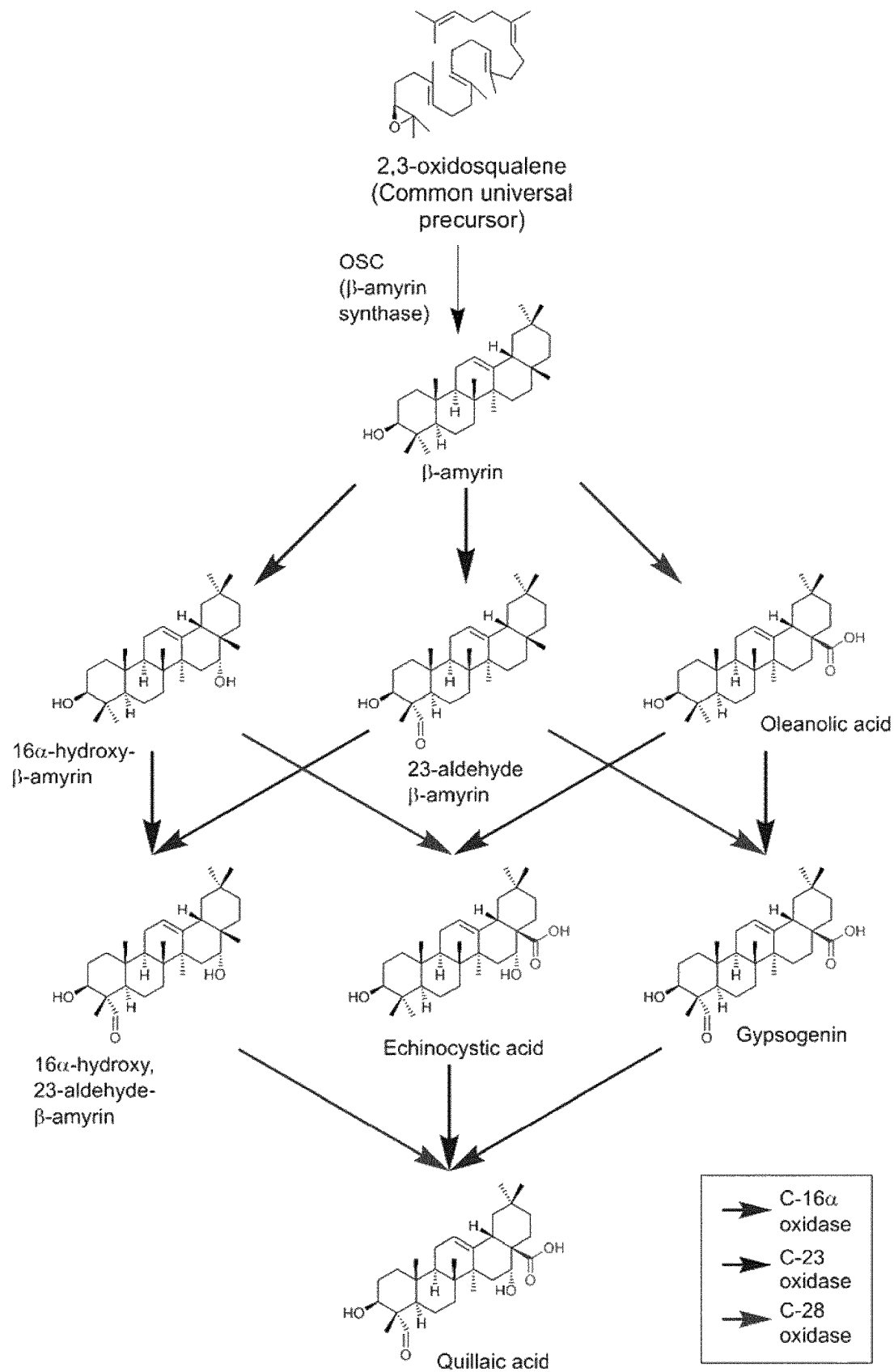

The oxidised derivatives of β-amyrin arising from successive oxidations by these enzymes are shown in FIG. 11 and summarised in the Table below:

| | Substrate | Enzyme | Product |
|---|---|---|---|
| First Oxidation | β-amyrin | C-16α-oxidase | 16α-hydroxy-β-amyrin |
| | β-amyrin | C-23-oxidase | 23-aldehyde-β-amyrin |
| | β-amyrin | C-28-oxidase | Oleanolic acid |
| Second Oxidation | 23-aldehyde-β-amyrin | C-16α-oxidase | 16α-hydroxy, 23-aldehyde-β-myrin |
| | Oleanolic acid | C-23-oxidase | Gypsogenin |
| | 16α-hydroxy-β-amyrin | C-28-oxidase | Echinocystic acid |
| Third Oxidation | Gypsogenin | C-16α-oxidase | Quillaic acid |
| | Echinocystic acid | C-23-oxidase | Quillaic acid |
| | 16α-hydroxy, 23-aldehyde-β-amyrin | C-28-oxidase | Quillaic acid |

By way of example, using the illustrative scheme of FIG. 2, these enzymes could be respectively:
- β-amyrin synthase;
- an enzyme capable of oxidising β-amyrin to oleanolic acid;
- an enzyme capable of oxidising oleanolic to echinocystic acid;
- an enzyme capable of oxidising echinocystic acid to QA.

The present inventors have successfully engineered the entire QA biosynthetic pathway into heterologous organisms which are not otherwise QA producers. Specifically, the present inventors demonstrated the invention by co-infiltration of *Agrobacterium tumefaciens* strains into *N. benthamiana*. This is the first description of heterologous production of quillaic acids achieved by co-expression of biosynthetic genes, and represents a major contribution to the art.

More specifically, the present inventors demonstrated that a minimum of four additional genes was sufficient for QA biosynthesis (bAS, and 3 CYP450s). These were advantageously combined with an optional HMG-CoA reductase to increase product levels.

Furthermore, in a further contribution to the art, the present inventors have identified genes in *Quillaja saponaria* coding for polypeptides affecting QA biosynthesis.

The methods and materials described herein can be used, inter alia, to produce recombinant host organisms (for example plants or microorganisms) which can produce QAs even though they are not naturally produced by the wild-type host.

De novo engineering of quillaic acids according to the present invention can produce plants or microorganisms containing high amounts of QA, which can in turn be used—for example—for further chemical synthesis of QS-21 [18].

Thus in one aspect of the invention there is provided a method of converting a host from a phenotype whereby the host is unable to carry out QA biosynthesis from OS to a phenotype whereby the host is able to carry out said QA biosynthesis,
  which method comprises the step of expressing a heterologous nucleic acid within the host or one or more cells thereof, following an earlier step of introducing the nucleic acid into the host or an ancestor of either,
  wherein the heterologous nucleic acid comprises a plurality of nucleotide sequences each of which encodes a polypeptide which in combination have said QA biosynthesis activity.

Preferably the nucleic acid encodes some or all (one, two, three or four) of the following enzymes:
  a β-amyrin synthase (bAS) for cyclisation of the universal linear precursor 2,3-oxidosqualene (OS) to a triterpene;
  a CYP450 capable of oxidising β-amyrin or an oxidised derivative thereof at the C-28 position to a carboxylic acid; a CYP450 capable of oxidising β-amyrin or an oxidised derivative thereof such as oleanolic acid at the C-16α position to an alcohol;
  a CYP450 capable of oxidising β-amyrin or an oxidised derivative thereof such as echinocystic acid at the C-23 position to an aldehyde.

In certain embodiments these CYP450 enzymes may be:
  a CYP450 capable of oxidising β-amyrin at the C-28 position to a carboxylic acid forming oleanolic acid;
  a CYP450 capable of oxidising oleanolic acid at the C-16α position to an alcohol forming echinocystic acid;
  a CYP450 capable of oxidising echinocystic acid at the C-23 position to an aldehyde forming QA.

Other potential intermediates will be understood by those skilled in the art in the light of the disclosure herein, and in particular FIG. 11.

For brevity these enzymes may be referred to as "bAS", "C-28 oxidase", "C-16α oxidase", and "C-23 oxidase" respectively herein.

For further brevity these enzymes may be referred to collectively as "QA polypeptides" herein.

In one embodiment at least one of the QA polypeptides originates from (is derived from) Q. saponaria Preferably 2, 3 or all 4 of the QA polypeptides originate from Q. saponaria In one embodiment:
  The C-28 oxidase is a CYP716
  The C-16α is a CYP716 or CYP87
  The C-23 oxidase is a CYP714, CYP72 or CYP94

Preferred genes or polypeptides for use in the practice of the invention are shown in the Sequence Annex.

In preferred embodiments, the one, two, three or four of the respective polypeptides are selected from the Q. saponaria sequences listed in Table 1 e.g. as follows:
  β-amyrin synthase (bAS)=SEQ ID: No 2
  The C-28 oxidase=SEQ ID: No 4
  The C-16α oxidase=SEQ ID: No 6
  The C-23 oxidase=SEQ ID: No 8
  or variants or fragments thereof as discussed below.

In other embodiments, the one, two, or three of the respective polypeptides are selected from the non-Q. saponaria sequences listed in Table 2a, 2b or 2c e.g. as follows:
  The C-28 oxidase=SEQ ID: No 18
  The C-16α oxidase=SEQ ID: No 10 or 12
  The C-23 oxidase=SEQ ID: No 14 or 16
  or variants or fragments thereof as discussed below.

In certain embodiments the QA polypeptides are encoded by a nucleotide sequence shown in any of SEQ ID: Nos 1, 3, 5, 7, 9, 11, 13, 15, or 17.
  or variants or fragments thereof as discussed below.

In other embodiments, the C-28 oxidase is a polypeptide encoded by one of the non-Q. saponaria accessions listed in Table 2d as SEQ ID Nos 19-28: (VvCYP716A15, VvCYP716A17, PgCYP716A52v2, MlCYP716A75, CqCYP716A78, CqCYP716A79, BvCYP716A80, BvCYP716A81, MdCYP716A175 or CrCYP716AL1), or is a variant or fragment thereof as discussed below. These nucleotide sequences are respectively referred to herein as SEQ ID NOs: 19-28.

For brevity the nucleotide sequences of any of Tables 1 and 2 may be referred to herein as "QA genes"

Variants

In addition to use of these QA genes (and polypeptides) the invention encompasses use of variants of these genes (and polypeptides).

A "variant" QA nucleic acid or QA polypeptide molecule shares homology with, or is identical to, all or part of the QA genes or polypeptides discussed herein.

A variant polypeptide shares the relevant biological activity of the native QA polypeptide. A variant nucleic acid encodes the relevant variant polypeptide.

In this context the "biological activity" of the QA polypeptide is the ability to catalyse the respective reaction shown in FIG. 2 and described above (i.e. the cyclase or oxidase activity). The relevant biological activities may be assayed based on the reactions shown in FIG. 2 (or corresponding oxidation reactions e.g. as per FIG. 11) in vitro. Alternatively they can be assayed by activity in vivo as described in the Examples i.e. by introduction of a plurality of heterologous constructs to generate QA, which can be assayed by LC-MS or the like.

Table 8 shows pairwise comparisons of the P450 enzymes described herein, obtained using Clustal Omega (version 1.2.4—accessed through https://www.ebi.ac.uk).

Variants of the sequences disclosed herein preferably share at least 50%, 55%, 56%, 57%, 58%, 59%, 60%, 65%, or 70%, or 80% identity, most preferably at least about 90%, 95%, 96%, 97%, 98% or 99% identity. Such variants may be referred to herein as "substantially homologous".

Preferred variants may be:
  (i) Naturally occurring nucleic acids such as alleles (which will include polymorphisms or mutations at one or more bases) or pseudoalleles (which may occur at closely linked loci to the QA genes of the invention). Also included are paralogues, isogenes, or other homologous genes belonging to the same families as the QA genes of the invention. Also included are orthologues or homologues from other plant species.

Table 4 illustrates minor sequence differences identified between the gene sequences as found in the 1 KP dataset and the sequenced clones obtained by PCR from the Q. saponaria plants in the present disclosure. This demonstrates that even with a c. 1500 bp of OQHZ-2012090, there were 19 variations identified (more than 1% variation).

Specifically envisaged by this disclosure are the use of QA genes or polypeptides including one or more of the variations described in Table 4 in the respective sequence. Furthermore, included within the scope of the present invention are nucleic acid molecules which encode amino acid sequences which are homologues of QA genes of the invention. Homology may be at the nucleotide sequence and/or amino acid sequence level, as discussed below.

(ii) Artificial nucleic acids, which can be prepared by the skilled person in the light of the present disclosure. Such derivatives may be prepared, for instance, by site directed or random mutagenesis, or by direct synthesis. Preferably the variant nucleic acid is generated either directly or indirectly (e.g. via one or more amplification or replication steps) from an original nucleic acid having all or part of the sequence of a QA gene of the invention.

Also included are nucleic acids corresponding to those above, but which have been extended at the 3' or 5' terminus.

The term "QA variant nucleic acid" as used herein encompasses all of these possibilities. When used in the context of polypeptides or proteins it indicates the encoded expression product of the variant nucleic acid.

In each case, the preferred QA-biosynthesis modifying nucleic acids are any of SEQ ID Nos 1, 3, 5, 7, 9, 11, 13, 15, and 17, or substantially homologous variants thereof.

The preferred QA-biosynthesis modifying polypeptides are any of SEQ ID Nos 2, 4, 6, 8, 10, 12, 14, 16, and 18, or substantially homologous variants thereof.

Other preferred QA-biosynthesis modifying nucleic acids for use in the invention are any of SEQ ID Nos 19 to 28, or substantially homologous variants or fragments thereof. Other preferred QA-biosynthesis modifying polypeptides are polypeptides encoded by any of these sequences or variants or fragments.

Supplementary Genes

In embodiments of the invention, in addition to the QA genes and variant nucleic acids of the invention described herein, it may be preferable to introduce additional genes which may affect flux of QA production.

For example MVA is an important intermediate in triterpenoid synthesis. Therefore it may be desirable to expression of rate-limiting MVA pathway genes into the host, to maximise yields of QA.

HMG-CoA reductase (HMGR) is believed to be a rate-limiting enzyme in the MVA pathway.

Figure 10:
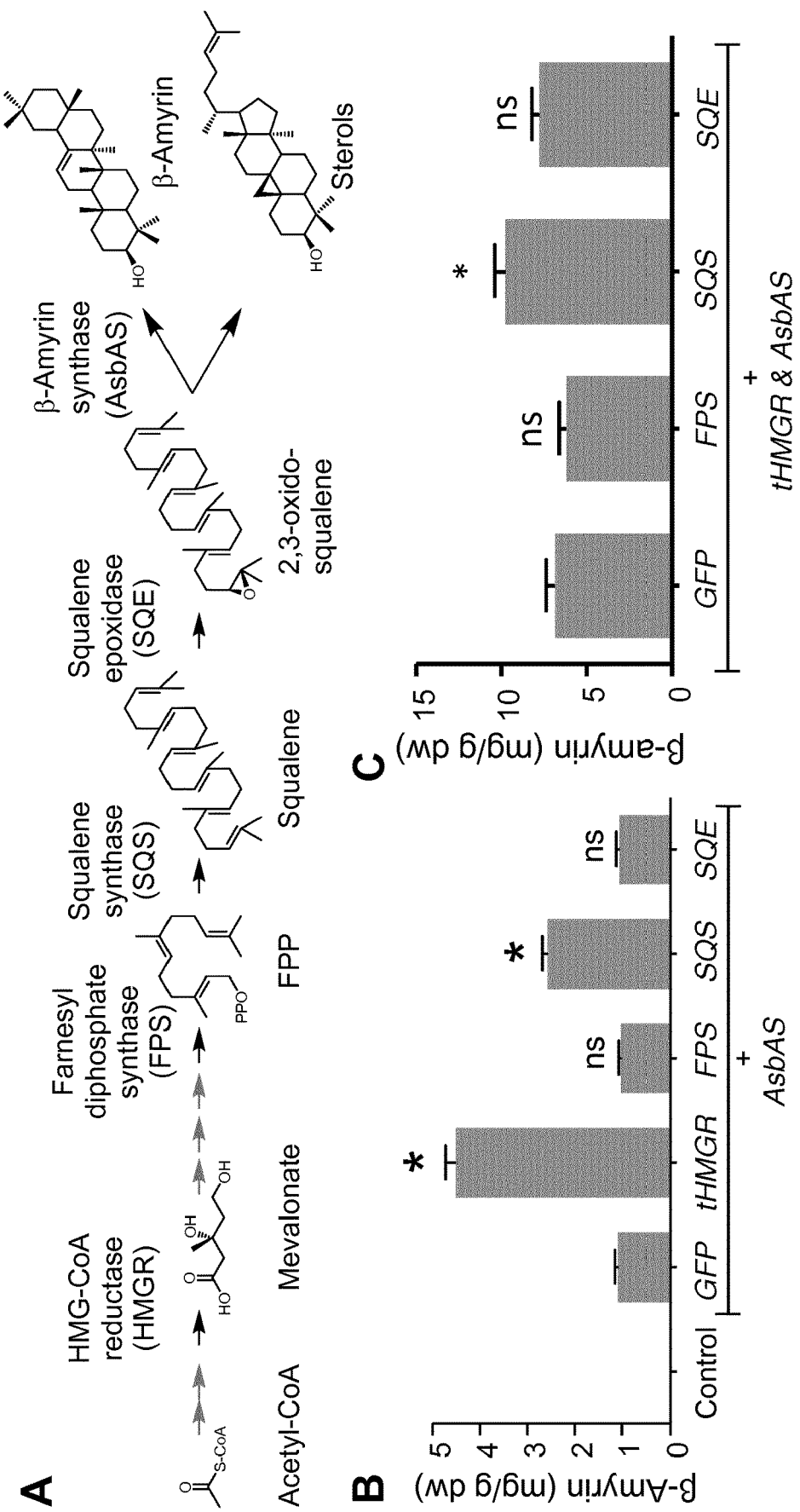

The use of a recombinant feedback-insensitive truncated form of HMGR (tHMGR) has been demonstrated to increase triterpene (β-amyrin) content upon transient expression in *N. benthamiana* [5], also FIG. 10.

Thus one embodiment of the invention comprises the use of a heterologous HMGR (e.g. a feedback-insensitive HMGR) along with the QA genes described herein. Examples of HMGR encoding or polypeptide sequences include SEQ ID Nos 29 to 32, or variants or fragments of these. Variants may be homologues, alleles, or artificial derivatives etc. as discussed in relation to QA genes or polypeptides as described above. For example an HMGR native to the host being utilised may be preferred—for example a yeast HMGR in a yeast host, and so on. HMGR genes are known in the art and may be selected, as appropriate in the light of the present disclosure.

It has also been reported that squalene synthase (SQS; see FIG. 10) is a potential rate-limiting step [5].

Thus one embodiment of the invention comprises the use of a heterologous SQS along with the QA genes and optionally HMGR described herein.

Examples of SQS encoding or polypeptide sequences include SEQ ID Nos 33 to 34, or variants or fragments of these. Variants may be homologues, alleles, or artificial derivatives etc. as discussed in relation to QA genes or polypeptides as described above. For example an SQS native to the host being utilised may be preferred—for example a yeast SQS in a yeast host, and so on. SQS genes are known in the art and may be selected, as appropriate in the light of the present disclosure.

When using certain hosts (for example yeasts) it may be desirable to introduce additional genes to improve the flux of QA production. Examples may include one or more plant cytochrome P450 reductases (CPRs) to serve as the redox partner to the introduced P450s. Thus one embodiment of the invention comprises the use of a heterologous cytochrome P450 reductase such as AtATR2 (*Arabidopsis thaliana* cytochrome P450 reductase 2) along with the QA genes described herein. Examples of HAtATR2 encoding or polypeptide sequences include SEQ ID Nos 35 to 36, or variants or fragments of these. Variants may be homologues, alleles, or artificial derivatives etc. as discussed in relation to QA genes or polypeptides as described above.

It will be understood by those skilled in the art, in the light of the present disclosure, that additional genes may be utilised in the practice of the invention, to provide additional activities and\or improve expression or activity. These include those expressing co-factor or helper proteins, or other factors. Examples may include genes involved in the synthesis of QS-21 from QA.

For brevity any of these nucleic acid sequences (the "QA genes of the invention" and "QA variant nucleic acids", plus other genes effecting QA synthesis, or secondary modifications to QA) may be referred to herein as "QA nucleic acid" or "QA-biosynthesis modifying nucleic acid". Likewise the encoded polypeptides may be referred to herein as "QA polypeptides" or "QA-biosynthesis modifying polypeptides".

It will be appreciated that where these generic terms are used in relation to any aspect or embodiment, the meaning will be taken to applies to any of these sequences individually.

Vectors

As one aspect of the invention there is disclosed a method employing the co-infiltration of a plurality of *Agrobacterium tumefaciens* strains each carrying one or more of the QA nucleic acids discussed above for concerted expression thereof in a biosynthetic pathway discussed above.

In some embodiments at least 3 or 4 different *Agrobacterium tumefaciens* strains are co-infiltrated e.g. each carrying a QA nucleic acid.

The genes may be present from transient expression vectors.

A preferred expression system utilises the called "'Hyper-Translatable' Cowpea Mosaic Virus ('CPMV-HT') system, described in WO2009/087391 the disclosure of which is specifically incorporated herein in support of the embodiments using the CPMV-HT system—for example vectors based on pEAQ-HT expression plasmids.

Thus the vectors (typically binary vectors) for use in the present invention will typically comprise an expression cassette comprising:

(i) a promoter, operably linked to
(ii) an enhancer sequence derived from the RNA-2 genome segment of a bipartite RNA virus, in which a target initiation site in the RNA-2 genome segment has been mutated;
(iii) a QA nucleic acid sequence as described above;
(iv) a terminator sequence; and optionally
(v) a 3' UTR located upstream of said terminator sequence.

Further examples of vectors and expression systems useful in the practice of the invention are described in more detail hereinafter.

Hosts

In aspects of the invention a host may be converted from a phenotype whereby the host is unable to carry out effective QA biosynthesis from OS to a phenotype whereby the host is able to carry out said QA biosynthesis, such that QA can be recovered therefrom or utilised in vivo to synthesize downstream products. Examples hosts includes plants such as *Nicotiana benthamiana* and microorganisms such as yeast. These are discussed in more detail below.

The invention may comprise transforming the host with heterologous nucleic acid as described above by introducing the QA nucleic acid into the host cell via a vector and causing or allowing recombination between the vector and the host cell genome to introduce a nucleic acid according to the present invention into the genome.

In another aspect of the invention there is provided a host cell transformed with a heterologous nucleic acid which comprises a plurality of nucleotide sequences each of which encodes a polypeptide which in combination have said QA biosynthesis activity, wherein expression of said nucleic acid imparts on the transformed host the ability to carry out QA biosynthesis from OS, or improves said ability in the host.

The invention further encompasses a host cell transformed with nucleic acid or a vector as described above (e.g. comprising the QA-biosynthesis modifying nucleotide sequences) especially a plant or a microbial cell. In the transgenic host cell (i.e. transgenic for the nucleic acid in question) the transgene may be on an extra-genomic vector or incorporated, preferably stably, into the genome. There may be more than one heterologous nucleotide sequence per haploid genome.

The methods and materials described herein can be used, inter alia, to generate stable crop-plants that accumulate QA.

Plants which include a plant cell according to the invention are also provided.

Production of Products

The methods described above may be used to generate QA in a heterologous host. The QA will generally be non-naturally occurring in the species into which they are introduced.

QAs from the plants or methods of the invention may be isolated and commercially exploited.

The methods above may form a part of, possibly one step in, a method of producing QS-21 in a host. The method may comprise the steps of culturing the host (where it is a microorganism) or growing the host (where it is a plant) and then harvesting it and purifying the QA or QS-21 product therefrom. The product thus produced forms a further aspect of the present invention. The utility of QA or QS-21 products is described above.

Alternatively, QA may be recovered to allow for further chemical synthesis of QS-21 [18].

Novel Genes of the Invention

In support of the present invention, the present inventors have newly characterised sequences from *Q. saponaria* which are believed to be involved in the synthesis of QA in that species (see SEQ. ID: Nos 1-8)

In preferred embodiments, the methods of the present invention will include the use of one or more of these newly characterised QA nucleic acids of the invention (e.g. one, two, three or four such QA nucleic acids) optionally in conjunction with the manipulation of other genes affecting QA biosynthesis known in the art.

These newly characterised QA sequences from *Q. saponaria* (SEQ. ID: Nos 1-8) form aspects of the invention in their own right, as do derived variants and materials o these sequences, and methods of using them.

Some aspects and embodiments of the present invention will now be described in more detail.

DETAILED DESCRIPTION OF THE INVENTION

In different embodiments, the present invention provides means for manipulation of total levels of QA in host cells such as microorganisms or plants.

In one aspect of the present invention, the QA-biosynthesis modifying nucleic acid described above is in the form of a recombinant and preferably replicable vector.

"Vector" is defined to include, inter alia, any plasmid, cosmid, phage or *Agrobacterium* binary vector in double or single stranded linear or circular form which may or may not be self-transmissible or mobilizable, and which can transform a prokaryotic or eukaryotic host either by integration into the cellular genome or exist extrachromosomally (e.g. autonomous replicating plasmid with an origin of replication).

As is well known to those skilled in the art, a "binary vector" system includes (a) border sequences which permit the transfer of a desired nucleotide sequence into a plant cell genome; (b) desired nucleotide sequence itself, which will generally comprise an expression cassette of (i) a plant active promoter, operably linked to (ii) the target sequence and\or enhancer as appropriate. The desired nucleotide sequence is situated between the border sequences and is capable of being inserted into a plant genome under appropriate conditions. The binary vector system will generally require other sequence (derived from *A. tumefaciens*) to effect the integration. Generally this may be achieved by use of so called "agro-infiltration" which uses *Agrobacterium*-mediated transient transformation. Briefly, this technique is based on the property of *Agrobacterium tumefaciens* to transfer a portion of its DNA ("T-DNA") into a host cell where it may become integrated into nuclear DNA. The T-DNA is defined by left and right border sequences which are around 21-23 nucleotides in length. The infiltration may be achieved e.g. by syringe (in leaves) or vacuum (whole plants). In the present invention the border sequences will generally be included around the desired nucleotide sequence (the T-DNA) with the one or more vectors being introduced into the plant material by agro-infiltration.

Generally speaking, those skilled in the art are well able to construct vectors and design protocols for recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press or *Current Protocols in Molecular Biology*, Second Edition, Ausubel et al. eds., John Wiley & Sons, 1992.

Specifically included are shuttle vectors by which is meant a DNA vehicle capable, naturally or by design, of replication in two different host organisms, which may be selected from actinomycetes and related species, bacteria and eucaryotic (e.g. higher plant, mosses, yeast or fungal cells).

A vector including nucleic acid according to the present invention need not include a promoter or other regulatory sequence, particularly if the vector is to be used to introduce the nucleic acid into cells for recombination into the genome.

Preferably the nucleic acid in the vector is under the control of, and operably linked to, an appropriate promoter or other regulatory elements for transcription in a host cell such as a microbial, e.g. yeast and bacterial, or plant cell. The vector may be a bi-functional expression vector which functions in multiple hosts. In the case of genomic DNA, this may contain its own promoter or other regulatory elements (optionally in combination with a heterologous enhancer, such as the 35S enhancer discussed in the Examples below). The advantage of using a native promoter is that this may avoid pleiotropic responses. In the case of cDNA this may be under the control of an appropriate promoter or other regulatory elements for expression in the host cell By "promoter" is meant a sequence of nucleotides from which transcription may be initiated of DNA operably linked downstream (i.e. in the 3' direction on the sense strand of double-stranded DNA).

"Operably linked" means joined as part of the same nucleic acid molecule, suitably positioned and oriented for transcription to be initiated from the promoter. DNA operably linked to a promoter is "under transcriptional initiation regulation" of the promoter.

In a preferred embodiment, the promoter is an inducible promoter.

The term "inducible" as applied to a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus.

Thus nucleic acid according to the invention may be placed under the control of an externally inducible gene promoter to place expression under the control of the user. An advantage of introduction of a heterologous gene into a plant cell, particularly when the cell is comprised in a plant, is the ability to place expression of the gene under the control of a promoter of choice, in order to be able to influence gene expression, and therefore QA biosynthesis, according to preference. Furthermore, mutants and derivatives of the wild-type gene, e.g. with higher or lower activity than wild-type, may be used in place of the endogenous gene.

Thus this aspect of the invention provides a gene construct, preferably a replicable vector, comprising a promoter (optionally inducible) operably linked to a nucleotide sequence provided by the present invention, such as the QA-biosynthesis modifying gene, most preferably one of the Qs QA nucleic acids which are described below, or a derivative thereof.

Particularly of interest in the present context are nucleic acid constructs which operate as plant vectors. Specific procedures and vectors previously used with wide success upon plants are described by Guerineau and Mullineaux (1993) (Plant transformation and expression vectors. In: Plant Molecular Biology Labfax (Croy RRD ed) Oxford, BIOS Scientific Publishers, pp 121-148). Suitable vectors may include plant viral-derived vectors (see e.g. EP-A-194809).

Preferably the vectors of the present invention which are for use in plants comprise border sequences which permit the transfer and integration of the expression cassette into the plant genome. Preferably the construct is a plant binary vector. Preferably the binary transformation vector is based on pPZP (Hajdukiewicz, et al. 1994). Other example constructs include pBin19 (see Frisch, D. A., L. W. Harris-Haller, et al. (1995). "Complete Sequence of the binary vector Bin 19." Plant Molecular Biology 27: 405-409).

Suitable promoters which operate in plants include the Cauliflower Mosaic Virus 35S (CaMV 35S). Other examples are disclosed at pg. 120 of Lindsey & Jones (1989) "Plant Biotechnology in Agriculture" Pub. OU Press, Milton Keynes, UK. The promoter may be selected to include one or more sequence motifs or elements conferring developmental and/or tissue-specific regulatory control of expression. Inducible plant promoters include the ethanol induced promoter of Caddick et al (1998) Nature Biotechnology 16: 177-180.

If desired, selectable genetic markers may be included in the construct, such as those that confer selectable phenotypes such as resistance to antibiotics or herbicides (e.g. kanamycin, hygromycin, phosphinotricin, chlorsulfuron, methotrexate, gentamycin, spectinomycin, imidazolinones and glyphosate). Positive selection system such as that described by Haldrup et al. 1998 Plant molecular Biology 37, 287-296, may be used to make constructs that do not rely on antibiotics.

As explained above, a preferred vector is a'CPMV-HT' vector as described in WO2009/087391. The Examples below demonstrate the use of these pEAQ-HT expression plasmids.

These vectors (typically binary vectors) for use in the present invention will typically comprise an expression cassette comprising:
(i) a promoter, operably linked to
(ii) an enhancer sequence derived from the RNA-2 genome segment of a bipartite RNA virus, in which a target initiation site in the RNA-2 genome segment has been mutated;
(iii) a QA nucleic acid sequence as described above;
(iv) a terminator sequence; and optionally
(v) a 3' UTR located upstream of said terminator sequence.

"Enhancer" sequences (or enhancer elements), as referred to herein, are sequences derived from (or sharing homology with) the RNA-2 genome segment of a bipartite RNA virus, such as a comovirus, in which a target initiation site has been mutated. Such sequences can enhance downstream expression of a heterologous ORF to which they are attached. Without limitation, it is believed that such sequences when present in transcribed RNA, can enhance translation of a heterologous ORF to which they are attached.

A "target initiation site" as referred to herein, is the initiation site (start codon) in a wild-type RNA-2 genome segment of a bipartite virus (e.g. a comovirus) from which the enhancer sequence in question is derived, which serves as the initiation site for the production (translation) of the longer of two carboxy coterminal proteins encoded by the wild-type RNA-2 genome segment.

Typically the RNA virus will be a comovirus as described hereinbefore.

Most preferred vectors are the pEAQ vectors of WO2009/087391 which permit direct cloning version by use of a polylinker between the 5' leader and 3' UTRs of an expression cassette including a translational enhancer of the invention, positioned on a T-DNA which also contains a suppressor of gene silencing and an NPTII cassettes.

The presence of a suppressor of gene silencing in such gene expression systems is preferred but not essential. Suppressors of gene silencing are known in the art and described in WO/2007/135480. They include HcPro from Potato virus Y, He-Pro from TEV, P19 from TBSV, rgsCam, B2 protein from FHV, the small coat protein of CPMV, and coat protein from TCV. A preferred suppressor when producing stable transgenic plants is the P19 suppressor incorporating a R43W mutation.

The present invention also provides methods comprising introduction of such a construct into a plant cell or a microbial (e.g. bacterial, yeast or fungal) cell and/or induction of expression of a construct within a plant cell, by application of a suitable stimulus e.g. an effective exogenous inducer.

As an alternative to microorganisms, cell suspension cultures of QA-producing plant species, including also the moss *Physcomitrella patens* may be cultured in fermentation tanks (see e.g. Grotewold et al. (Engineering Secondary Metabolites in Maize Cells by Ectopic Expression of Transcription Factors, Plant Cell, 10, 721-740, 1998).

In a further aspect of the invention, there is disclosed a host cell containing a heterologous construct according to the present invention, especially a plant or a microbial cell.

The discussion of host cells above in relation to reconstitution of QA biosynthesis in heterologous organisms applies mutatis mutandis here.

Thus a further aspect of the present invention provides a method of transforming a plant cell involving introduction of a construct as described above into a plant cell and causing or allowing recombination between the vector and the plant cell genome to introduce a nucleic acid according to the present invention into the genome.

The invention further encompasses a host cell transformed with nucleic acid or a vector according to the present invention (e.g. comprising the QA-biosynthesis modifying nucleotide sequence) especially a plant or a microbial cell. In the transgenic plant cell (i.e. transgenic for the nucleic acid in question) the transgene may be on an extra-genomic vector or incorporated, preferably stably, into the genome. There may be more than one heterologous nucleotide sequence per haploid genome.

Yeast has seen extensive employment as a triterpene-producing host [6-8, 19-22] and is therefore potentially well adapted for QA biosynthesis.

Therefore in one embodiment, the host is a yeast. For such hosts, it may be desirable to introduce additional genes to improve the flux of QA production as described above. Examples may include one or more plant cytochrome P450 reductases (CPRs) to serve as the redox partner to the introduced P450s [6], as well as an HMGR.

Plants, which include a plant cell transformed as described above, form a further aspect of the invention.

If desired, following transformation of a plant cell, a plant may be regenerated, e.g. from single cells, callus tissue or leaf discs, as is standard in the art. Almost any plant can be entirely regenerated from cells, tissues and organs of the plant. Available techniques are reviewed in Vasil et al., Cell Culture and Somatic Cell Genetics of Plants, Vol I, II and Ill, Laboratory Procedures and Their Applications, Academic Press, 1984, and Weissbach and Weissbach, Methods for Plant Molecular Biology, Academic Press, 1989.

In addition to the regenerated plant, the present invention embraces all of the following: a clone of such a plant, seed, selfed or hybrid progeny and descendants (e.g. F1 and F2 descendants). The invention also provides a plant propagule from such plants, that is any part which may be used in reproduction or propagation, sexual or asexual, including cuttings, seed and so on. It also provides any part of these plants, which in all cases include the plant cell or heterologous QA-biosynthesis modifying DNA described above.

The present invention also encompasses the expression product of any of the coding QA-biosynthesis modifying nucleic acid sequences disclosed and methods of making the expression product by expression from encoding nucleic acid therefore under suitable conditions, which may be in suitable host cells.

As described below, plant backgrounds such as those above may be natural or transgenic e.g. for one or more other genes relating to QA biosynthesis, or otherwise affecting that phenotype or trait.

In modifying the host phenotypes, the QA nucleic acids described herein may be used in combination with any other gene, such as transgenes affecting the rate or yield of QA, or its modification, or any other phenotypic trait or desirable property.

By use of a combination of genes, plants or microorganisms (e.g. bacteria, yeasts or fungi) can be tailored to enhance production of desirable precursors, or reduce undesirable metabolism.

As an alternative, down-regulation of genes in the host may be desired e.g. to reduce undesirable metabolism or fluxes which might impact on QA yield.

Such down regulation may be achieved by methods known in the art, for example using anti-sense technology.

In using anti-sense genes or partial gene sequences to down-regulate gene expression, a nucleotide sequence is placed under the control of a promoter in a "reverse orientation" such that transcription yields RNA which is complementary to normal mRNA transcribed from the "sense" strand of the target gene. See, for example, Rothstein et al, 1987; Smith et al, (1988) *Nature* 334, 724-726; Zhang et al, (1992) *The Plant Cell* 4, 1575-1588, English et al., (1996) *The Plant Cell* 8, 179-188. Antisense technology is also reviewed in Bourque, (1995), *Plant Science* 105, 125-149, and Flavell, (1994) *PNAS USA* 91, 3490-3496.

An alternative to anti-sense is to use a copy of all or part of the target gene inserted in sense, that is the same, orientation as the target gene, to achieve reduction in expression of the target gene by co-suppression. See, for example, van der Krol et al., (1990) *The Plant Cell* 2, 291-299; Napoli et al., (1990) *The Plant Cell* 2, 279-289; Zhang et al., (1992) *The Plant Cell* 4, 1575-1588, and U.S. Pat. No. 5,231,020. Further refinements of the gene silencing or co-suppression technology may be found in WO95/34668 (Biosource); Angell & Baulcombe (1997) The EMBO Journal 16, 12:3675-3684; and Voinnet & Baulcombe (1997) Nature 389: pg 553.

Double stranded RNA (dsRNA) has been found to be even more effective in gene silencing than both sense or antisense strands alone (Fire A. et al *Nature*, Vol 391, (1998)). dsRNA mediated silencing is gene specific and is often termed RNA interference (RNAi) (See also Fire (1999) *Trends Genet.* 15: 358-363, Sharp (2001) *Genes Dev.* 15: 485-490, Hammond et al. (2001) *Nature Rev. Genes* 2: 1110-1119 and Tuschl (2001) *Chem. Biochem.* 2: 239-245).

RNA interference is a two step process. First, dsRNA is cleaved within the cell to yield short interfering RNAs (siRNAs) of about 21-23 nt length with 5' terminal phosphate and 3' short overhangs (~2 nt) The siRNAs target the corresponding mRNA sequence specifically for destruction (Zamore P. D. Nature Structural Biology, 8, 9, 746-750, (2001)

Another methodology known in the art for down-regulation of target sequences is the use of "microRNA" (miRNA) e.g. as described by Schwab et al 2006, Plant Cell 18, 1121-1133. This technology employs artificial miRNAs, which may be encoded by stem loop precursors incorporating suitable oligonucleotide sequences, which sequences can be generated using well defined rules in the light of the disclosure herein.

The methods of the present invention embrace both the in vitro and in vivo production, or manipulation, of one or more QAs. For example, QA polypeptides may be employed in fermentation via expression in microorganisms such as e.g. *E. coli*, yeast and filamentous fungi and so on. In one embodiment, one or more newly characterised Qs QA sequences of the present invention may be used in these organisms in conjunction with one or more other biosynthetic genes.

In vivo methods are describe extensively above, and generally involve the step of causing or allowing the transcription of, and then translation from, a recombinant nucleic acid molecule encoding the QA polypeptides.

In other aspects of the invention, the QA polypeptides (enzymes) may be used in vitro, for example in isolated, purified, or semi-purified form. Optionally they may be the product of expression of a recombinant nucleic acid molecule.

As explained above QS-21 is a purified plant extract that enhances the ability of the immune system to respond to vaccine antigens.

QS-21 has utility as an immunologic adjuvant believed to enhance both humoral and cell-mediated immunity. QS-21 has been under clinical evaluation as an additive for various trial vaccines, including those for HIV, malaria and cancer. It is a component of the FDA-approved Shingrix shingles vaccine.

Newly Characterised Sequences from *Quillaja* Saponaria

As noted above, in support of the present invention, the inventors have identified genes from *Q. saponaria* which are believed to encode polypeptides which affect QA biosynthesis (see SEQ. ID: Nos 1-8 in Table 1).

In certain aspects of the present invention, the QA nucleic acid is derived from *Q. saponaria* (SEQ. ID: Nos 1-8). Although it is believe that the key steps described herein for QA production (synthesis and oxidation of triterpenes) are likely to take place on the cytosolic face of the endoplasmic reticulum, such genes may be preferred, particularly for use in the preparation of stable transgenic plant hosts, since these native plant genes may be processed and function most effectively in the appropriate compartments of these hosts.

The above newly characterised QA biosynthetic genes from *Q. saponaria*. Thus form aspects of the present invention in their own right.

In a further aspect of the present invention there are disclosed nucleic acids which are variants of the QA nucleic acid is derived from *Q. saponaria* discussed above.

Such variants, as with the native QA genes discussed herein, may be used to alter the QA content of a plant, as assessed by the methods disclosed herein. For instance a variant nucleic acid may include a sequence encoding a variant QA polypeptide sharing the relevant biological activity of the native QA polypeptide, as discussed above. Examples include variants of any of SEQ ID Nos 2, 4, 6, or 8.

Derivatives

Described herein are methods of producing a derivative nucleic acid comprising the step of modifying any of the QA genes of the present invention disclosed above, particularly the QA sequences from *Q. saponaria*.

Changes may be desirable for a number of reasons. For instance they may introduce or remove restriction endonuclease sites or alter codon usage. This may be particularly desirable where the Qs genes are to be expressed in alternative hosts e.g. microbial hosts such as yeast. Methods of codon optimizing genes for this purpose are known in the art (see e.g. Elena, Claudia, et al. "Expression of codon optimized genes in microbial systems: current industrial applications and perspectives." *Frontiers in microbiology* 5 (2014)). Thus sequences described herein including codon modifications to maximise yeast expression represent specific embodiments of the invention.

Alternatively changes to a sequence may produce a derivative by way of one or more (e.g. several) of addition, insertion, deletion or substitution of one or more nucleotides in the nucleic acid, leading to the addition, insertion, deletion or substitution of one or more (e.g. several) amino acids in the encoded polypeptide.

Such changes may modify sites which are required for post translation modification such as cleavage sites in the encoded polypeptide; motifs in the encoded polypeptide for phosphorylation etc. Leader or other targeting sequences (e.g. membrane or golgi locating sequences) may be added to the expressed protein to determine its location following expression if it is desired to isolate it from a microbial system.

Other desirable mutations may be random or site directed mutagenesis in order to alter the activity (e.g. specificity) or stability of the encoded polypeptide. Changes may be by way of conservative variation, i.e. substitution of one hydrophobic residue such as isoleucine, valine, leucine or methionine for another, or the substitution of one polar residue for another, such as arginine for lysine, glutamic for aspartic acid, or glutamine for asparagine. As is well known to those skilled in the art, altering the primary structure of a polypeptide by a conservative substitution may not significantly alter the activity of that peptide because the side-chain of the amino acid which is inserted into the sequence may be able to form similar bonds and contacts as the side chain of the amino acid which has been substituted out. This is so even when the substitution is in a region which is critical in determining the peptides conformation. Also included are variants having non-conservative substitutions. As is well known to those skilled in the art, substitutions to regions of a peptide which are not critical in determining its conformation may not greatly affect its activity because they do not greatly alter the peptide's three dimensional structure. In regions which are critical in determining the peptides conformation or activity such changes may confer advantageous properties on the polypeptide. Indeed, changes such as those described above may confer slightly advantageous properties on the peptide e.g. altered stability or specificity.

Fragments

The present invention may utilise fragments of the polypeptides encoding the QA genes of the present invention disclosed above, particularly the QA sequences from *Q. saponaria*.

Thus the present invention provides for the production and use of fragments of the full-length QA polypeptides of the invention disclosed herein, especially active portions thereof. An "active portion" of a polypeptide means a peptide which is less than said full length polypeptide, but which retains its essential biological activity.

A "fragment" of a polypeptide means a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids. Fragments of the polypeptides may include one or more epitopes useful for raising antibodies to a portion of any of the amino acid sequences disclosed herein. Preferred epitopes are those to which antibodies are able to bind specifically, which may be taken to be binding a polypeptide or fragment thereof of the invention with an affinity which is at least about 1000× that of other polypeptides.

A specific fragment disclosed herein is the shorter isoform of CYP716-2012090, which is shown within in SEQ ID No 6 i.e. one which lacks the N-terminal 21 amino acids underlined in the sequence Annex.

For brevity, and of these QA sequences from *Q. saponaria* or variants (e.g. derivatives such as fragments thereof) may be referred to as "Qs QA sequences (or nucleic acid, or polypeptide)". These Qs QA polypeptides, and nucleic acids encoding them, form one aspect of the invention.

It will be appreciated that where this term is used generally, it also applies to any of these sequences individually.

Thus in one aspect of the invention, there is disclosed isolated nucleic acid encoding any of these polypeptides (2, 4, 6, or 8). Preferably this may have the sequence of 1, 3, 5, or 7. Other nucleic acids of the invention include those which are degeneratively equivalent to these, or homologous variants (e.g. derivatives) of these.

Aspects of the invention further embrace isolated nucleic acid comprising a sequence which is complementary to any of those discussed hereinafter.

Use of a Qs QA sequence to catalyse its respective biological activity (as described in FIG. 1) forms another aspect of the invention. For brevity any of these sequences may be referred to as "Qs QA sequences".

Thus the invention further provides a method of influencing or affecting QA biosynthesis in a host such as a plant, the method including causing or allowing transcription of a heterologous Qs QA nucleic acid as discussed above within the cells of the plant. The step may be preceded by the earlier step of introduction of the Qs QA nucleic acid into a cell of the plant or an ancestor thereof.

Such methods will usually form a part of, possibly one step in, a method of producing a QA in a host such as a plant. Preferably the method will employ a QA modifying polypeptide of the present invention (e.g. in Table 1) or derivative thereof, as described above, or nucleic acid encoding either.

In a further embodiment, there are provided antibodies raised to a Qs QA polypeptides or peptides of the invention Some aspects of the invention as it relates to heterologous reconstitution of the biosynthetic pathways discussed above will now be discussed in more detail.

"Nucleic acid" according to the present invention may include cDNA, RNA, genomic DNA and modified nucleic acids or nucleic acid analogs (e.g. peptide nucleic acid). Where a DNA sequence is specified, e.g. with reference to a figure, unless context requires otherwise the RNA equivalent, with U substituted for T where it occurs, is encompassed. Nucleic acid molecules according to the present invention may be provided isolated and/or purified from their natural environment, in substantially pure or homogeneous form, or free or substantially free of other nucleic acids of the species of origin, and double or single stranded. Where used herein, the term "isolated" encompasses all of these possibilities. The nucleic acid molecules may be wholly or partially synthetic. In particular they may be recombinant in that nucleic acid sequences which are not found together in nature (do not run contiguously) have been ligated or otherwise combined artificially. Nucleic acids may comprise, consist, or consist essentially of, any of the sequences discussed hereinafter.

The term "heterologous" is used broadly herein to indicate that the gene/sequence of nucleotides in question (e.g. encoding QA-biosynthesis modifying polypeptides) have been introduced into said cells of the host or an ancestor thereof, using genetic engineering, i.e. by human intervention. Nucleic acid heterologous to a host cell will be non-naturally occurring in cells of that type, variety or species. Thus the heterologous nucleic acid may comprise a coding sequence of or derived from a particular type of plant cell or species or variety of plant, placed within the context of a plant cell of a different type or species or variety of plant. A further possibility is for a nucleic acid sequence to be placed within a cell in which it or a homologue is found naturally, but wherein the nucleic acid sequence is linked and/or adjacent to nucleic acid which does not occur naturally within the cell, or cells of that type or species or variety of plant, such as operably linked to one or more regulatory sequences, such as a promoter sequence, for control of expression.

"Transformed" in this context means that the nucleotide sequences of the heterologous nucleic acid alter one or more of the cell's characteristics and hence phenotype e.g. with respect to QA biosynthesis. Such transformation may be transient or stable.

"Unable to carry out QA biosynthesis" means that the host, prior to the conversion, does not, or is not believed to, naturally produce detectable or recoverable levels of QA under normal metabolic circumstances of that host.

The nucleotide sequence information provided herein may be used to design probes and primers for probing or amplification. An oligonucleotide for use in probing or PCR may be about 30 or fewer nucleotides in length (e.g. 18, 21 or 24). Generally specific primers are upwards of 14 nucleotides in length. For optimum specificity and cost effectiveness, primers of 16-24 nucleotides in length may be preferred. Those skilled in the art are well versed in the design of primers for use in processes such as PCR. If required, probing can be done with entire restriction fragments of the gene disclosed herein which may be 100's or even 1000's of nucleotides in length. Small variations may be introduced into the sequence to produce 'consensus' or 'degenerate' primers if required.

Probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridised to the single stranded DNA fragments on the filter and binding determined. DNA for probing may be prepared from RNA preparations from cells. Probing may optionally be done by means of so-called 'nucleic acid chips' (see Marshall & Hodgson (1998) Nature Biotechnology 16: 27-31, for a review).

In one embodiment, a variant encoding a QA-biosynthesis modifying polypeptide in accordance with the present invention is obtainable by means of a method which includes:

(a) providing a preparation of nucleic acid, e.g. from plant cells. Test nucleic acid may be provided from a cell as genomic DNA, cDNA or RNA, or a mixture of any of these, preferably as a library in a suitable vector. If genomic DNA is used the probe may be used to identify untranscribed regions of the gene (e.g. promoters etc.), such as are described hereinafter, (b) providing a nucleic acid molecule which is a probe or primer as discussed above, (c) contacting nucleic acid in said preparation with said nucleic acid molecule under conditions for hybridisation of said nucleic acid molecule to any said gene or homologue in said preparation, and, (d) identifying said gene or homologue if present by its hybridisation with said nucleic acid molecule. Binding of a probe to target nucleic acid (e.g. DNA) may be measured using any of a variety of techniques at the disposal of those skilled in the art. For instance, probes may be radioactively, fluorescently or enzymatically labelled. Other methods not employing labelling of probe include amplification using PCR (see below), RN'ase cleavage and allele specific oligonucleotide probing. The identification of successful hybridisation is followed by isolation of the nucleic acid which has hybridised, which may involve one or more steps of PCR or amplification of a vector in a suitable host.

Preliminary experiments may be performed by hybridising under low stringency conditions. For probing, preferred conditions are those which are stringent enough for there to be a simple pattern with a small number of hybridisations identified as positive which can be investigated further.

For example, hybridizations may be performed, according to the method of Sambrook et al. (below) using a hybridization solution comprising: 5×SSC (wherein 'SSC'=0.15 M sodium chloride; 0.15 M sodium citrate; pH 7), 5×Denhardt's reagent, 0.5-1.0% SDS, 100 μg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42-65° C. in 1×SSC and 1% SDS, changing the solution every 30 minutes.

One common formula for calculating the stringency conditions required to achieve hybridization between nucleic acid molecules of a specified sequence homology is (Sambrook et al., 1989): $T_m=81.5° C.+16.6 \text{ Log } [Na+]+0.41$ (% G+C)−0.63 (% formamide)−600/#bp in duplex As an illustration of the above formula, using [Na+]= [0.368] and 50-% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C. Such a sequence would be considered substantially homologous to the nucleic acid sequence of the present invention.

It is well known in the art to increase stringency of hybridisation gradually until only a few positive clones remain. Other suitable conditions include, e.g. for detection of sequences that are about 80-90% identical, hybridization overnight at 42° C. in 0.25M $Na_2HPO_4$, pH 7.2, 6.5% SDS, 10% dextran sulfate and a final wash at 55° C. in 0.1×SSC, 0.1% SDS. For detection of sequences that are greater than about 90% identical, suitable conditions include hybridization overnight at 65° C. in 0.25M $Na_2HPO_4$, pH 7.2, 6.5% SDS, 10% dextran sulfate and a final wash at 60° C. in 0.1×SSC, 0.1% SDS.

In a further embodiment, hybridization of a nucleic acid molecule to a variant may be determined or identified indirectly, e.g. using a nucleic acid amplification reaction, particularly the polymerase chain reaction (PCR). PCR requires the use of two primers to specifically amplify target nucleic acid, so preferably two nucleic acid molecules with sequences characteristic of a QA gene of the present invention are employed. Using RACE PCR, only one such primer may be needed (see "PCR protocols; A Guide to Methods and Applications", Eds. Innis et al, Academic Press, New York, (1990)).

Thus a method involving use of PCR in obtaining nucleic acid according to the present invention may include:
 (a) providing a preparation of plant nucleic acid, e.g. from a seed or other appropriate tissue or organ,
 (b) providing a pair of nucleic acid molecule primers useful in (i.e. suitable for) PCR, at least one of said primers being a primer according to the present invention as discussed above,
 (c) contacting nucleic acid in said preparation with said primers under conditions for performance of PCR,
 (d) performing PCR and determining the presence or absence of an amplified PCR product. The presence of an amplified PCR product may indicate identification of a variant.

In all cases above, if need be, clones or fragments identified in the search can be extended. For instance if it is suspected that they are incomplete, the original DNA source (e.g. a clone library, mRNA preparation etc.) can be revisited to isolate missing portions e.g. using sequences, probes or primers based on that portion which has already been obtained to identify other clones containing overlapping sequence.

Purified protein according to the present invention, or a fragment, mutant, derivative or variant thereof, e.g. produced recombinantly by expression from encoding nucleic acid therefor, may be used to raise antibodies employing techniques which are standard in the art. Antibodies and polypeptides comprising antigen-binding fragments of antibodies may be used in identifying homologues from other species as discussed further below.

Methods of producing antibodies include immunising a mammal (e.g. human, mouse, rat, rabbit, horse, goat, sheep or monkey) with the protein or a fragment thereof. Antibodies may be obtained from immunised animals using any of a variety of techniques known in the art, and might be screened, preferably using binding of antibody to antigen of interest. For instance, Western blotting techniques or immunoprecipitation may be used (Armitage et al, 1992, Nature 357: 80-82). Antibodies may be polyclonal or monoclonal.

As an alternative or supplement to immunising a mammal, antibodies with appropriate binding specificity may be obtained from a recombinantly produced library of expressed immunoglobulin variable domains, e.g. using lambda bacteriophage or filamentous bacteriophage which display functional immunoglobulin binding domains on their surfaces; for instance see WO92/01047.

Antibodies raised to a polypeptide or peptide can be used in the identification and/or isolation of homologous polypeptides, and then the encoding genes.

Antibodies may be modified in a number of ways. Indeed the term "antibody" should be construed as covering any specific binding substance having a binding domain with the required specificity. Thus, this term covers antibody fragments, derivatives, functional equivalents and homologues of antibodies, including any polypeptide comprising an immunoglobulin binding domain, whether natural or synthetic.

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Any sub-titles herein are included for convenience only, and are not to be construed as limiting the disclosure in any way.

The invention will now be further described with reference to the following non-limiting Figures and Examples. Other embodiments of the invention will occur to those skilled in the art in the light of these.

The disclosure of all references cited herein, inasmuch as it may be used by those skilled in the art to carry out the invention, is hereby specifically incorporated herein by cross-reference.

FIGURES

FIG. 1: QS-21.

FIG. 2: Production of quillaic acid via β-amyrin, from common universal precursors. The pathway from β-amyrin requires oxidation at three (C-16α, C-23 and C-28) positions. These oxidation steps are shown in a linear fashion for simplicity only, although as explained above they can in principle progress in in other sequence (see FIG. 11).

Figure 3:
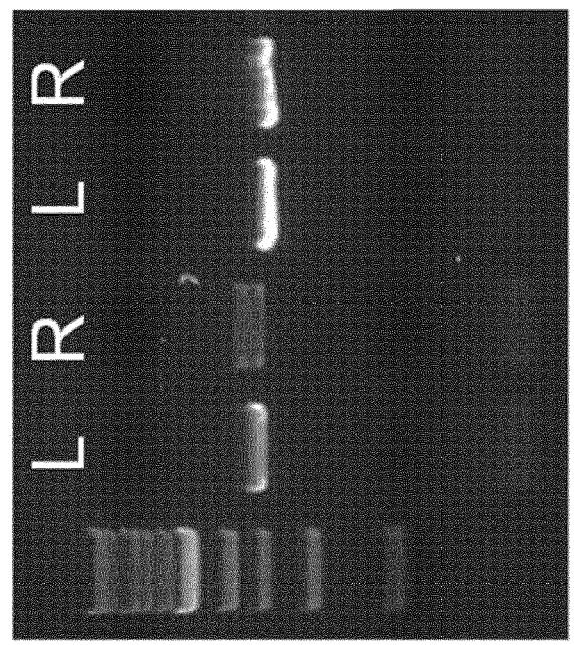
Figure 3:
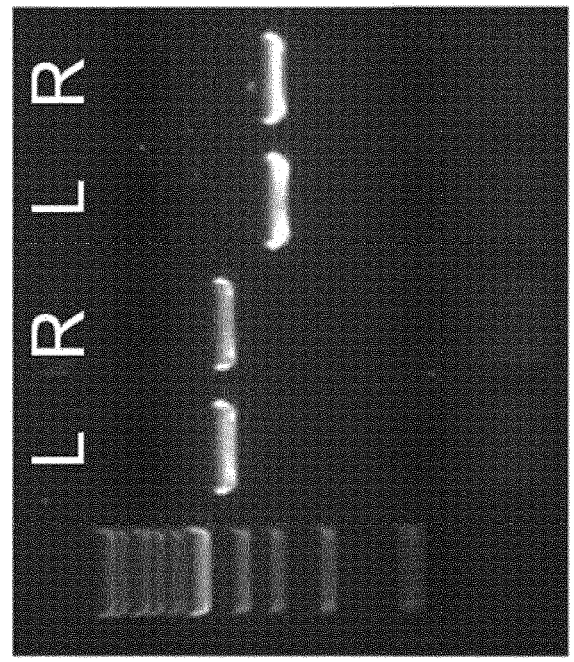

FIG. 3: PCR amplification of candidate genes in leaf (L) and root (R) tissue of *Q. saponaria*. It was possible to get a product for most candidates in both tissues.

Figure 4:
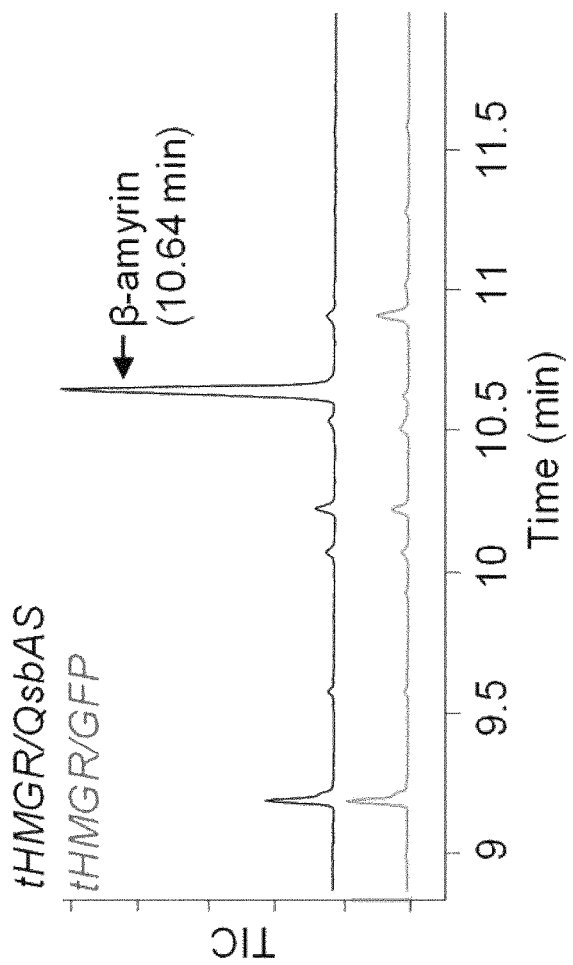
Figure 4:
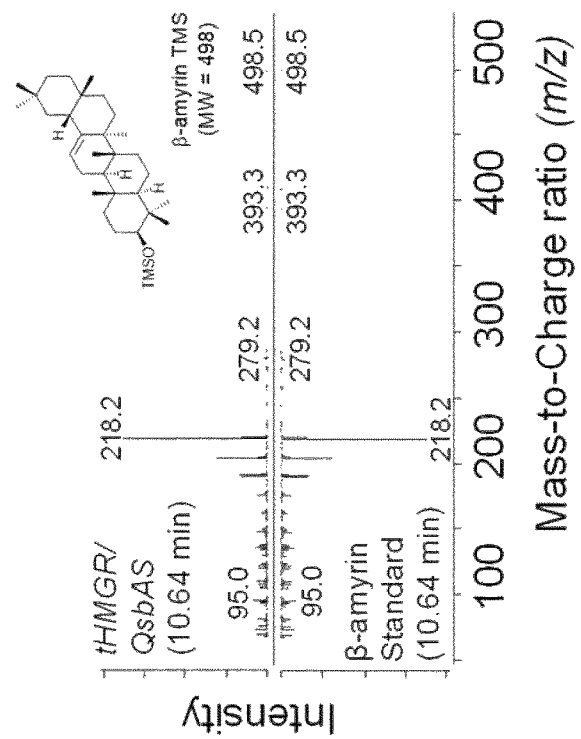

FIG. 4: Expression of *Q. saponaria* β-amyrin synthase (QsbAS) in *Nicotiana benthamiana*. GC-MS analysis of leaf extracts reveals production of β-amyrin only in leaves expressing the cloned β-amyrin synthase, but not in control (GFP) leaves.

Figure 5:
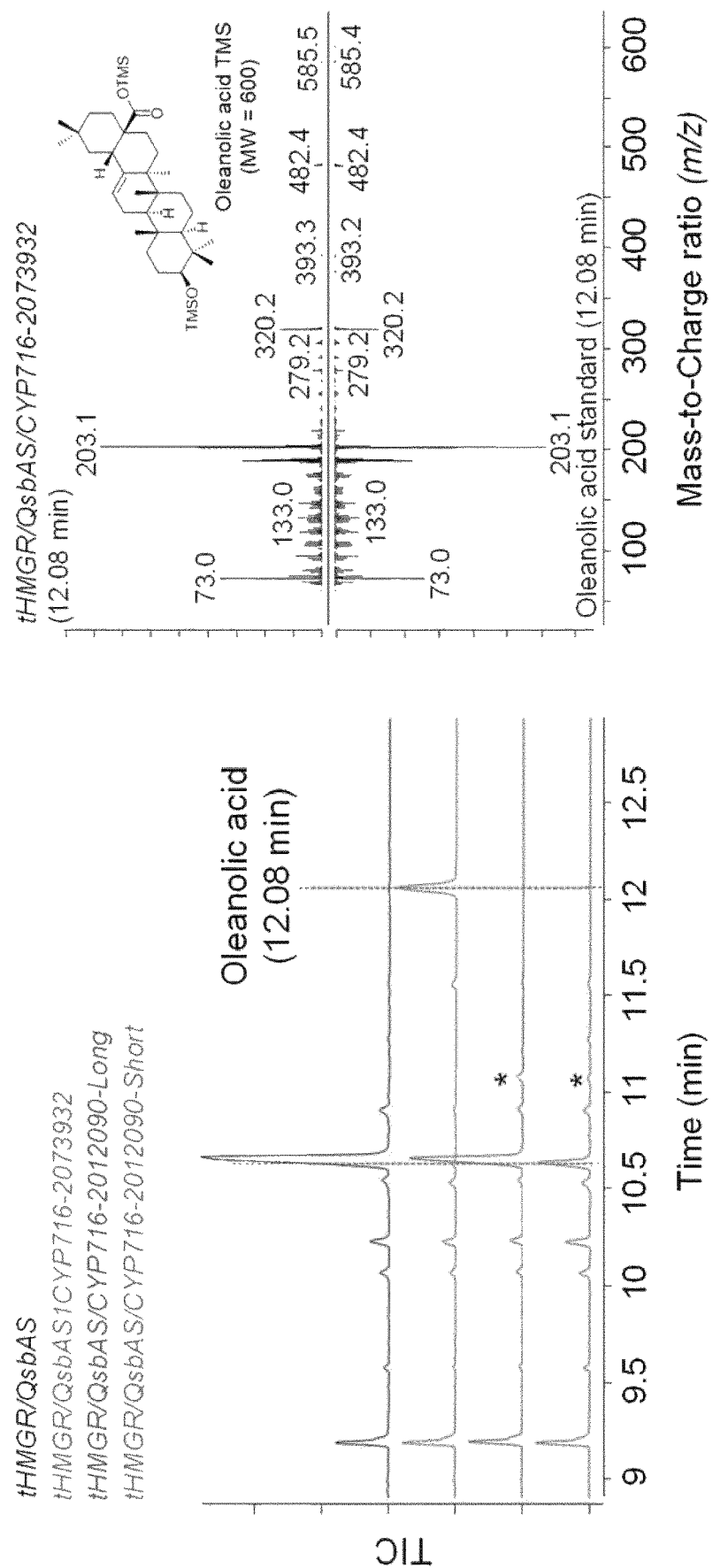

FIG. 5: Conversion of β-amyrin by P450s from *Q. saponaria*. Two P450s in the CYP716 family were found to oxidise β-amyrin. Left side: GC-MS analysis of *N. benthamiana* leaf extracts showing that CYP716-2073932 converted the majority of β-amyrin to a new product identified as oleanolic acid at 12.08 min. The mass spectrum for this product versus an authentic oleanolic acid standard is shown on the right side. CYP716-2012090 (both long and short isoforms) converted a small amount of β-amyrin putatively identified as 16α-hydroxy-β-amyrin (marked with *). The mass spectrum for this product is given in FIG. 5*i* s.

Figure 5S:
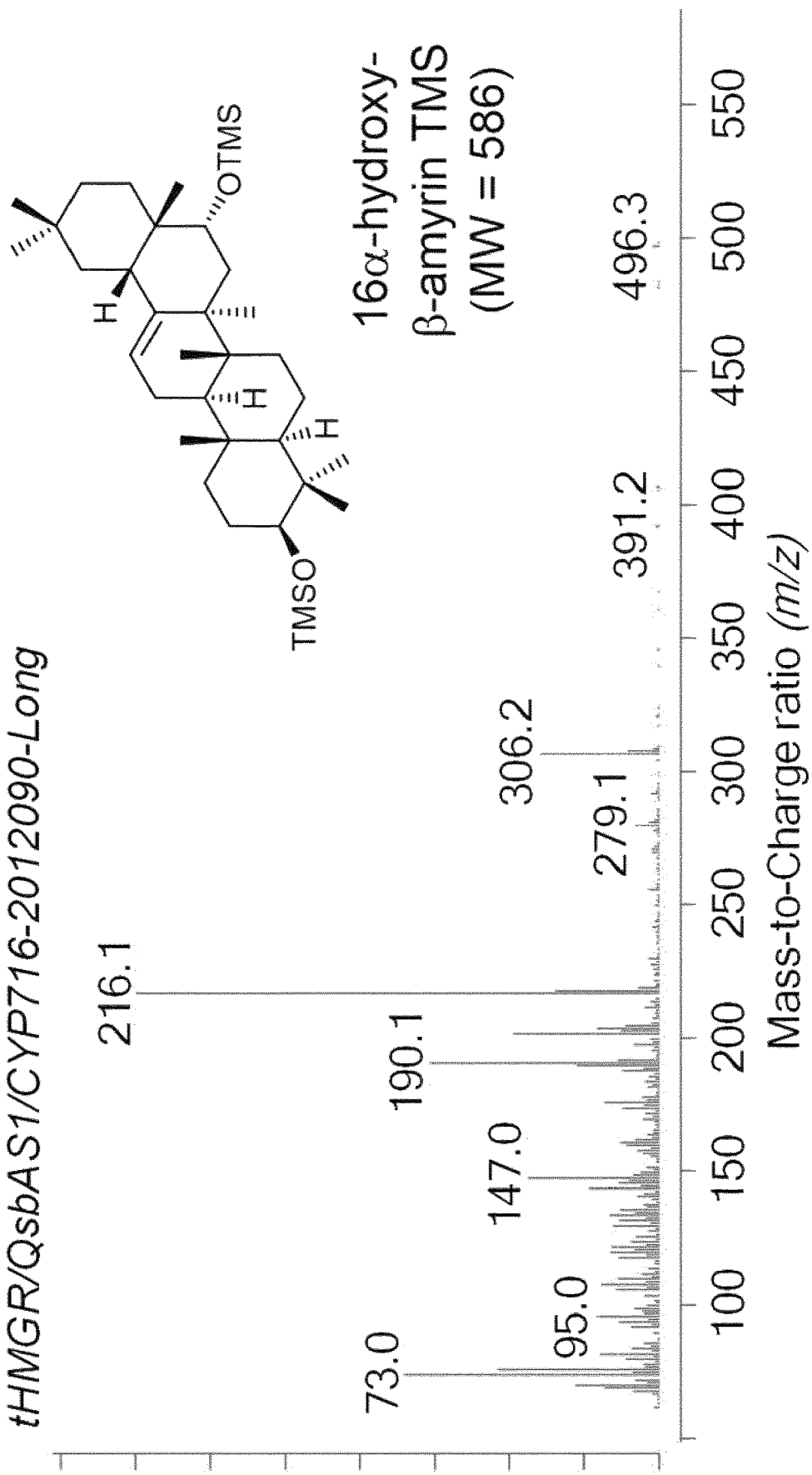

FIG. 5S: EI mass spectrum for the putative 16α-hydroxy-β-amyrin. Trace amounts of this product were formed upon coexpression of QsbAS and CYP716-2012090.

Figure 6A:
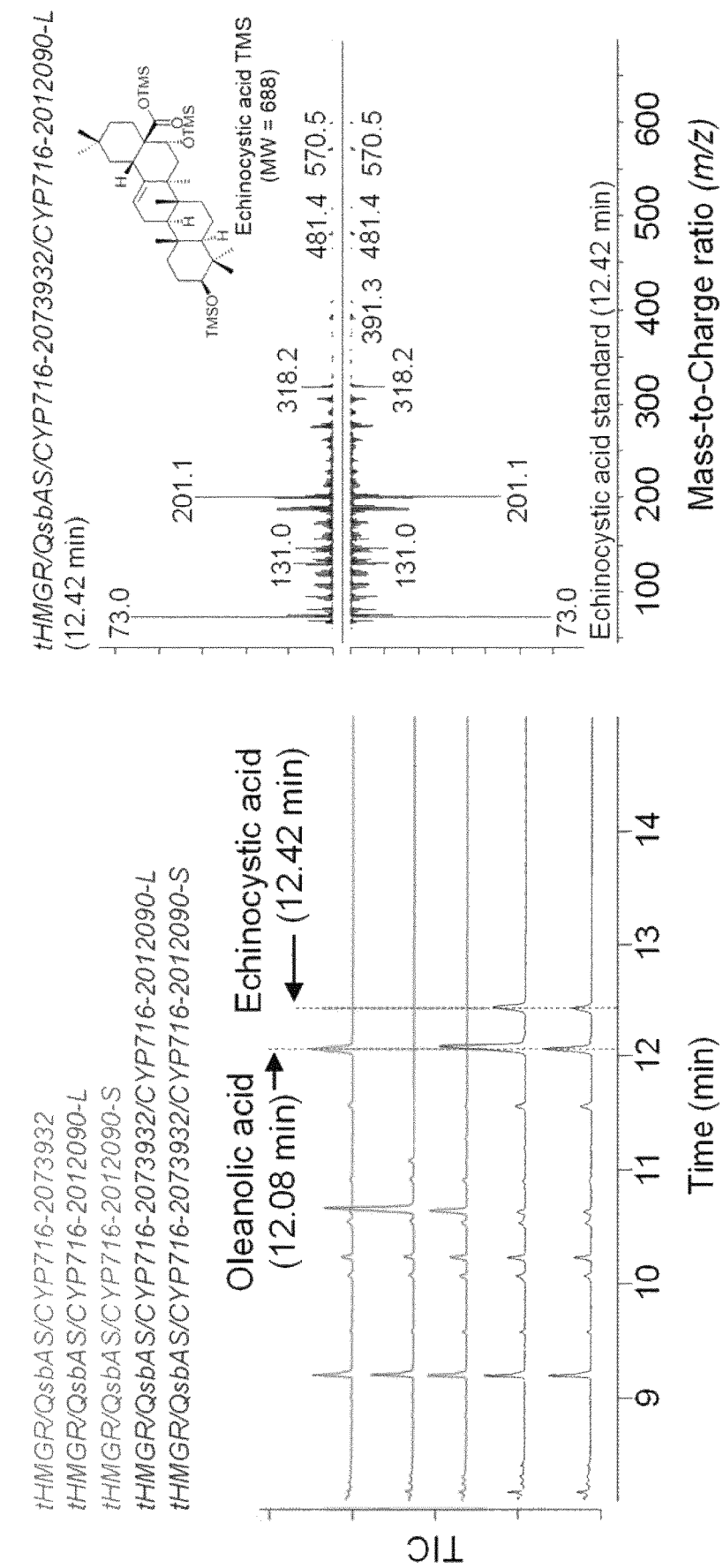

FIG. 6A: Conversion of oleanolic acid to echinocystic acid by CYP716-2012090. Left side: GC-MS analysis of *N. benthamiana* leaf extracts showing that coexpression of the two CYP716 members from *Q. saponaria* with QsbAS and CYP716-2073932 results in accumulation of a product at 12.42 min identified as echinocystic acid. The mass spectrum for this compound versus an authentic echinocystic acid standard is shown on the right side.

Figure 6B:
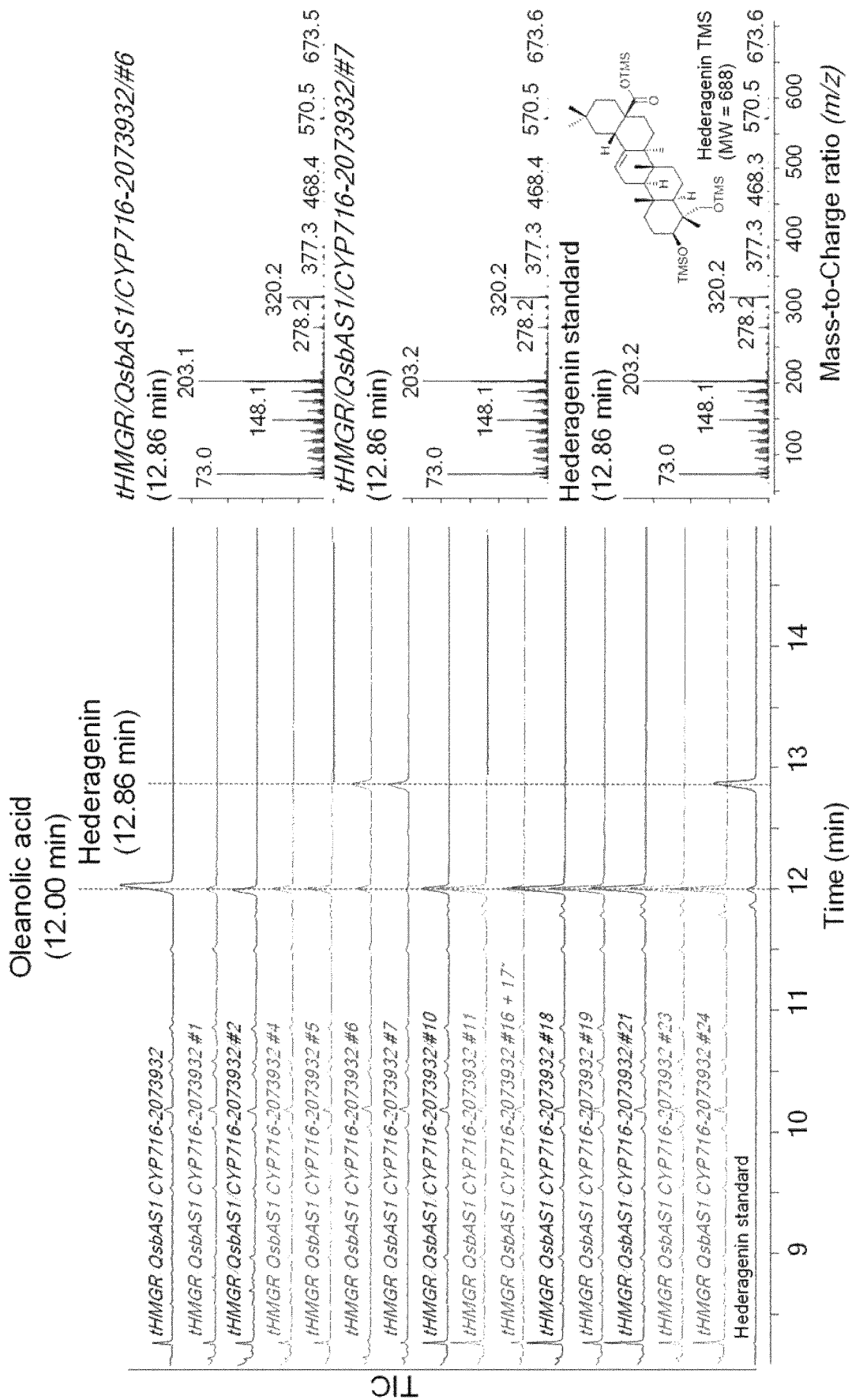

FIG. 6B: Conversion of oleanolic acid to hederagenin by OQHZ-2018687. Screening C-23 oxidase candidates for oleanolic acid-oxidising activity. Reveled that a new product was observed in samples expressing candidates #6 and #7 (which carry the same enzyme, also referred to as CYP714-7 herein). This new product had an identical retention time and mass spectrum to a 23-hydroxy-oleanolic acid (hederagenin) standard and suggests that the enzyme is a C-23 oxidase.

Figure 7:
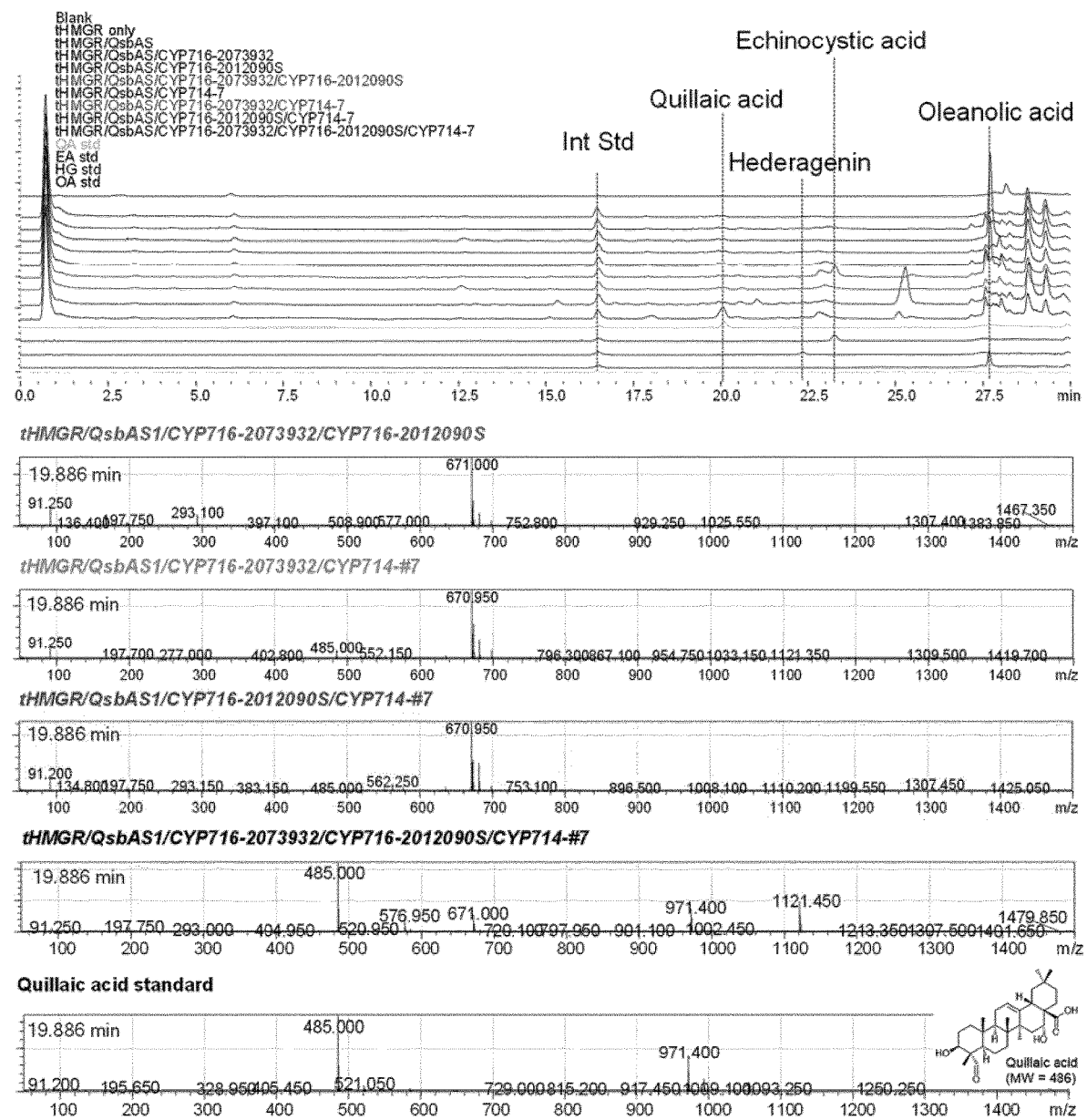

FIG. 7: LC-MS analysis of leaf extracts of *N. benthamiana* expressing combinations of QsbAS and the C-28 (CYP716-2073932), C-16α (CYP716-2012090) and C-23 (CYP714-7) oxidases from *Q. saponaria*. Quillaic acid (19.886 min) was observed only in the samples expressing all three P450s. Mass spectra for the various samples at 19.886 min are shown below along with a quillaic acid standard.

Figure 8:
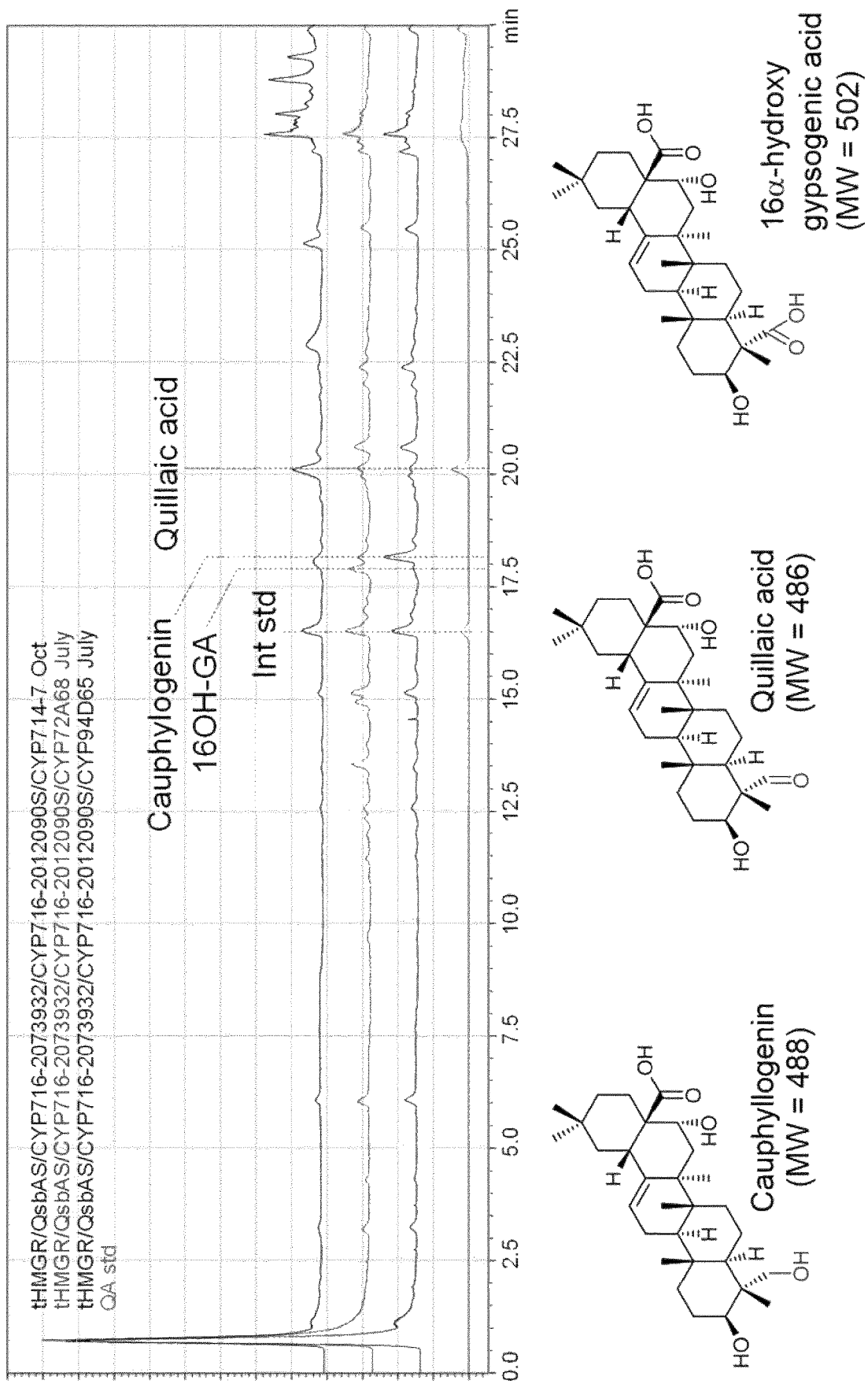

FIG. 8: Comparison of quillaic acid production between plant samples expressing different C-23 oxidases. All samples derive from leaves expressing tHMGR, QsbAS, and *Q. saponaria* C-28 (CYP716-2073932) and C-16α (CYP716-2012090) oxidases. The C-23 oxidases were derived from either *Q. saponaria* (CYP714-7, top), *M. truncatula* (CYP72A68, 2$^{nd}$ down) or *A. strigosa* (CYP94D65, 3$^{rd}$ down).

The CAD chromatogram is shown at the top. Mass spectra (negative mode) of interest are shown below.

A common ion with m/z 485 (shown in red) was common to both the quillaic acid standard and novel peak in tHMGR/QsbAS/CYP716-2073932/CYP716-2012090/CYP94D65 samples. This ion fits the expected molecular mass of quillaic acid (minus H). *A second compound was found in high abundance with m/z 487 that was putatively identified as cauphyllogenin (featuring a C-23 alcohol instead of an aldehyde as seen in quillaic acid). Mass spectra for these products are shown in FIG. 8*i* s.

Fewer alternative C-23-oxidised side products, including the C-23 alcohol (cauphylogenin) and acid (16α-hydroxy-gypsogenic acid (16OH-GA)) were found in the *Q. saponaria* C-23-expressing sample, suggesting greater specificity for production of the aldehyde.

Figure 9:
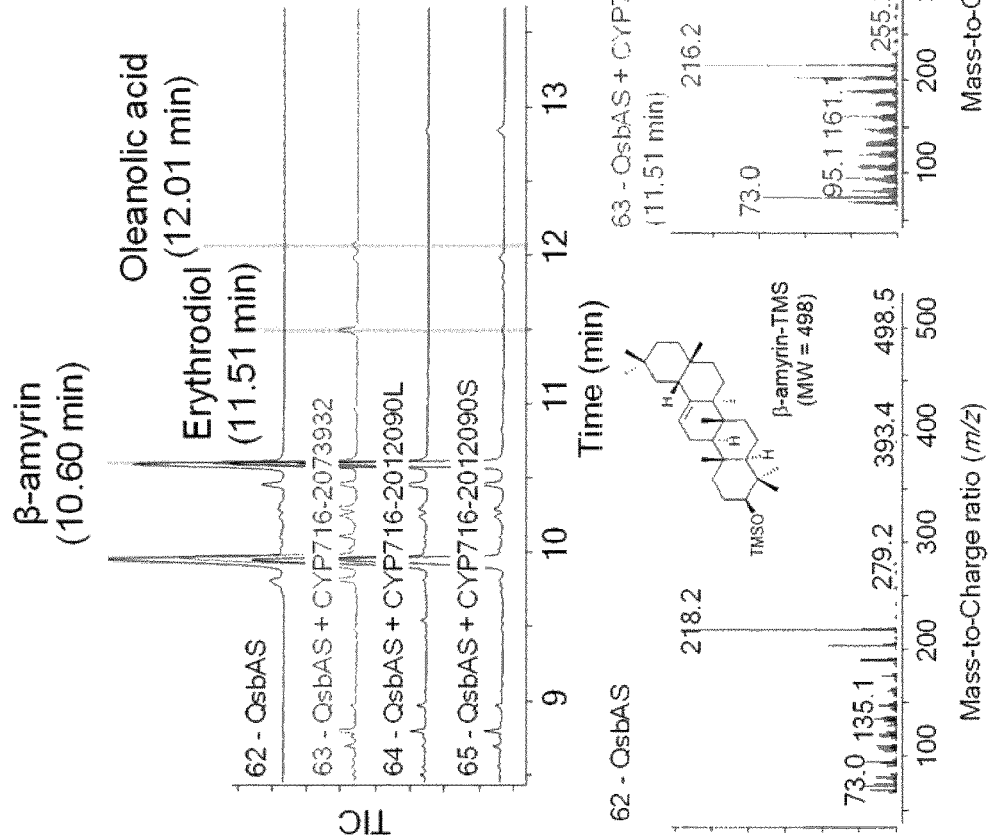

FIG. 9: Expression of *Q. saponaria* genes in yeast. GC-MS traces are given at the top for the different strains, mass spectra for peaks of interest are given below.

FIG. 10: A) Simplified overview of the mevalonate (MVA) pathway required for triterpene biosynthesis and potential rate-limiting enzymes. B) β-amyrin content in *N. benthamiana* can be improved from coexpression of tHMGR or SQS with an oat β-amyrin synthase (AsbAS). C) Coexpression of SQS with tHMGR further improves β-amyrin content over tHMGR alone.

FIG. 11: Oxidised derivatives of β-amyrin.

Figure 12:
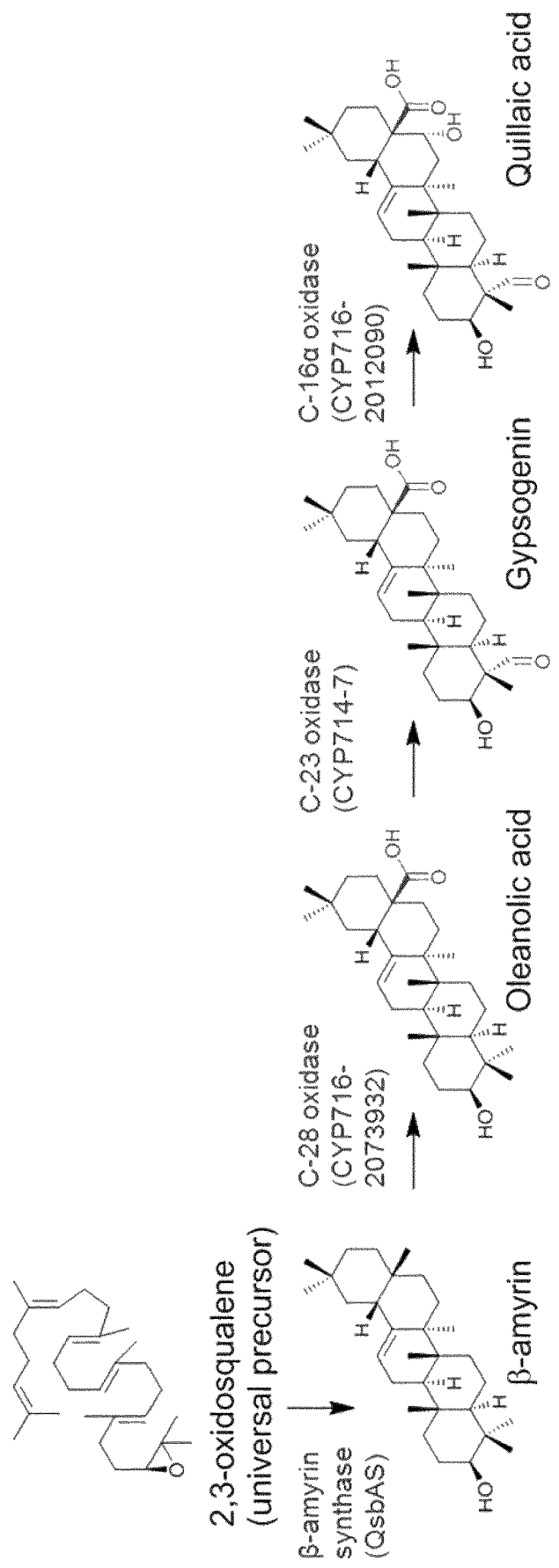

FIG. 12: Biosynthesis of quillaic acid from 2,3-oxidosqualene and the associated enzymes from *Q. saponaria*. The oxidation steps may not occur exactly in this order.

Figure 13:
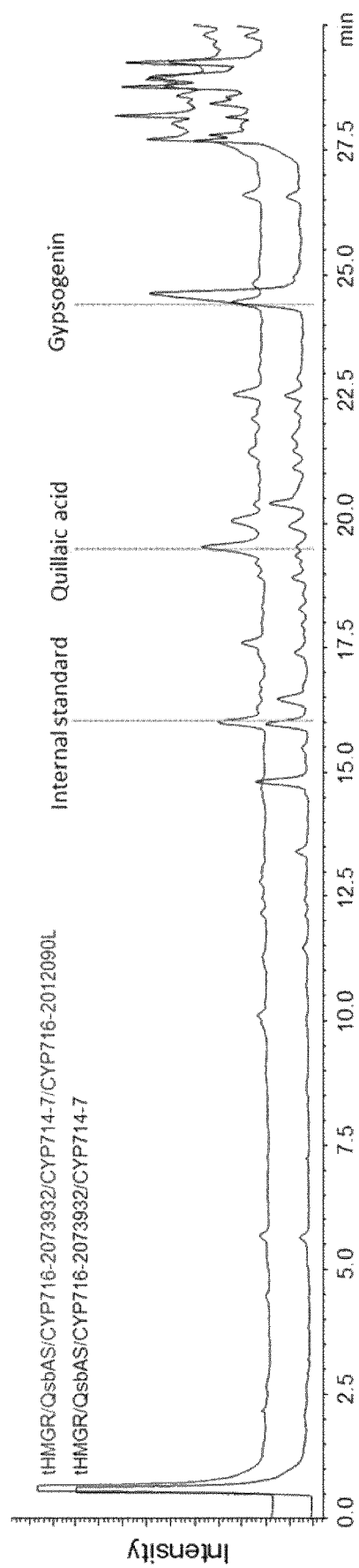

FIG. 13: LC-CAD analysis of representative leaves expressing the four characterised enzymes from *Q. saponaria* required to make quillaic acid (upper). As a control, the C-16a oxidase was excluded (lower) and instead accumulates the precursor gypsogenin (see FIG. 12).

Figure 14:
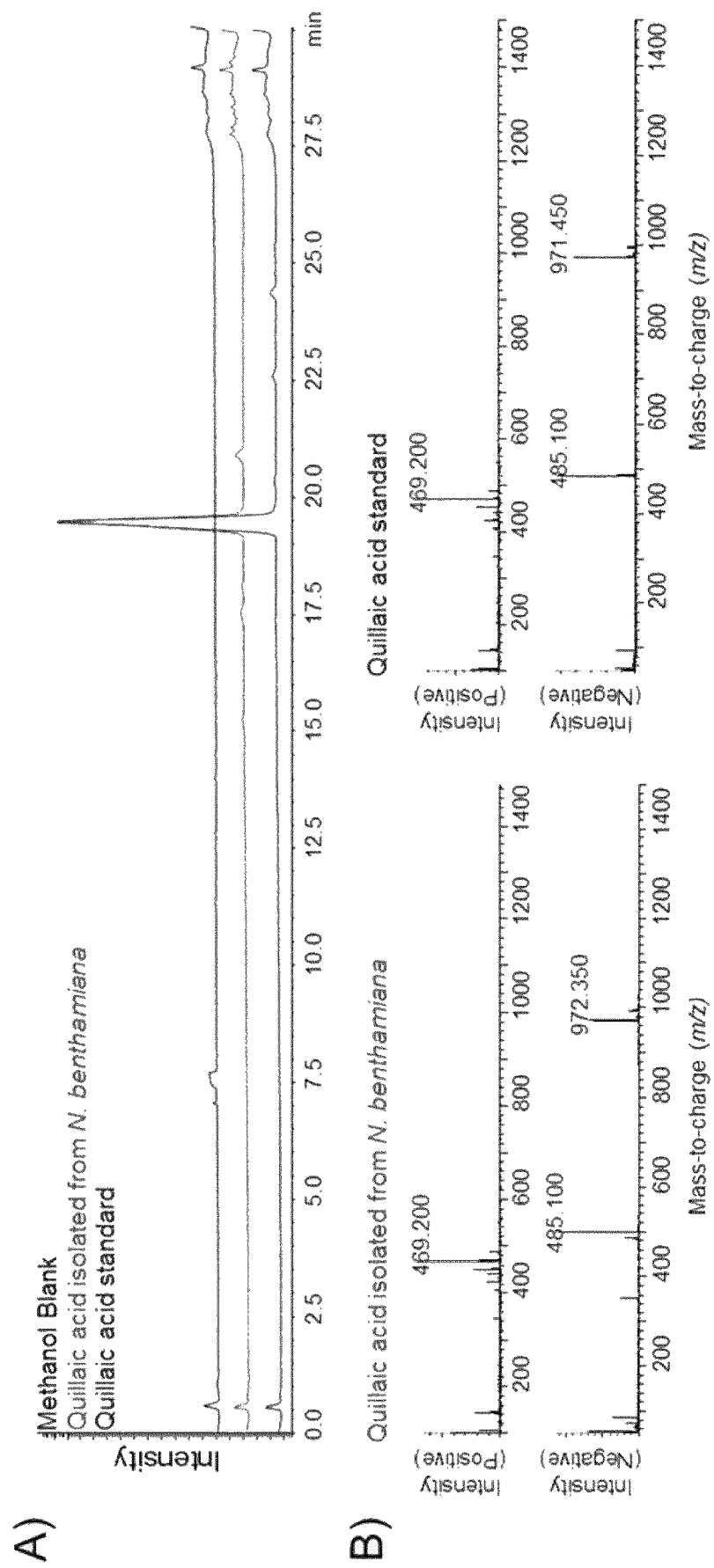

FIG. 14: LC analysis of a quillaic acid standard versus the product isolated from *N. benthamiana*. A) LC-CAD traces showing analysis of the isolated product (middle) and the quillaic acid standard (lower). Both samples showed a major peak at 19.5 minutes. A methanol-only blank run is shown in the top trace. B) MS (ESI/APC) analysis of the product at 19.5 minutes in both positive (upper) and negative (lower) mode. The isolated product is shown to the left with the quillaic acid standard on the right.

Figure 15:
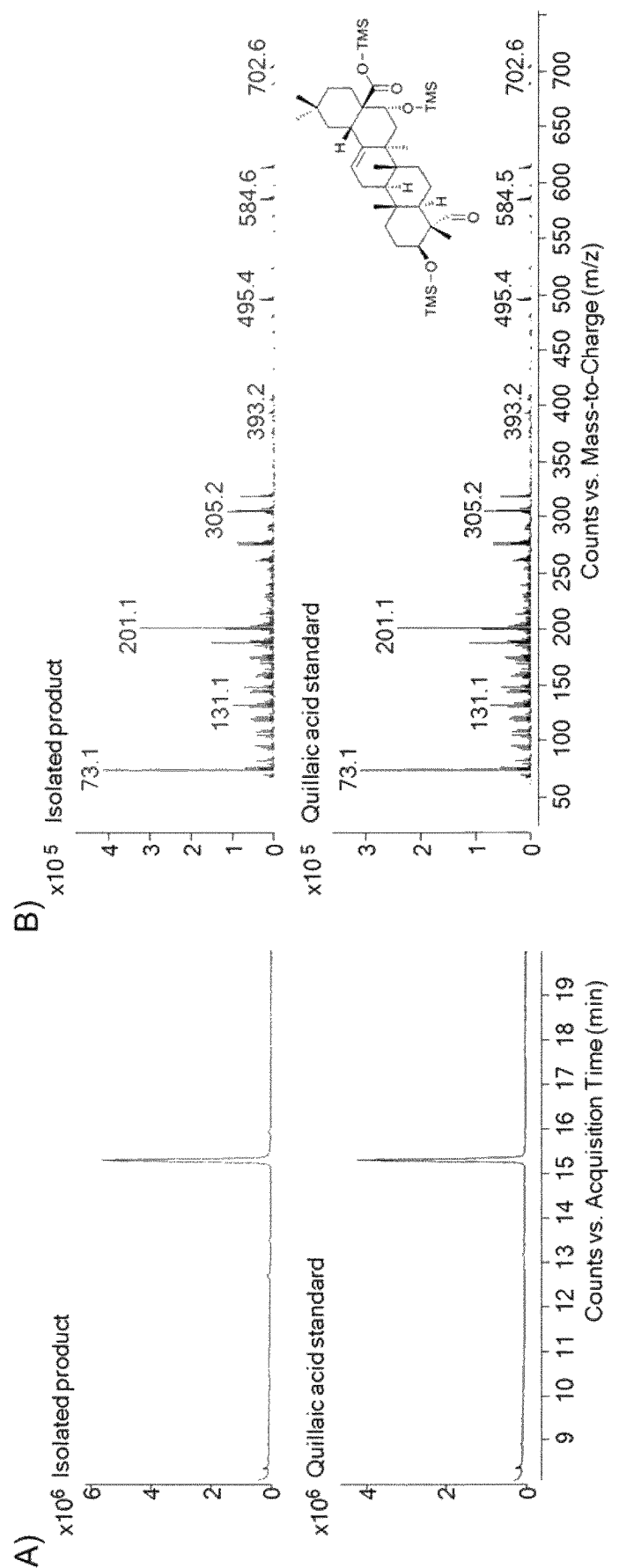

FIG. 15: GC-MS analysis of a quillaic acid standard versus the product isolated from *N. benthamiana*. A) The standard is shown in the lower trace, with the isolated product shown in the upper trace. Both samples showed a major peak at 15.3 minutes. B) Comparison of EI mass spectra of the two products at 15.3 min. The isolated product is shown above, with the quillaic acid standard below.

Figure 16:
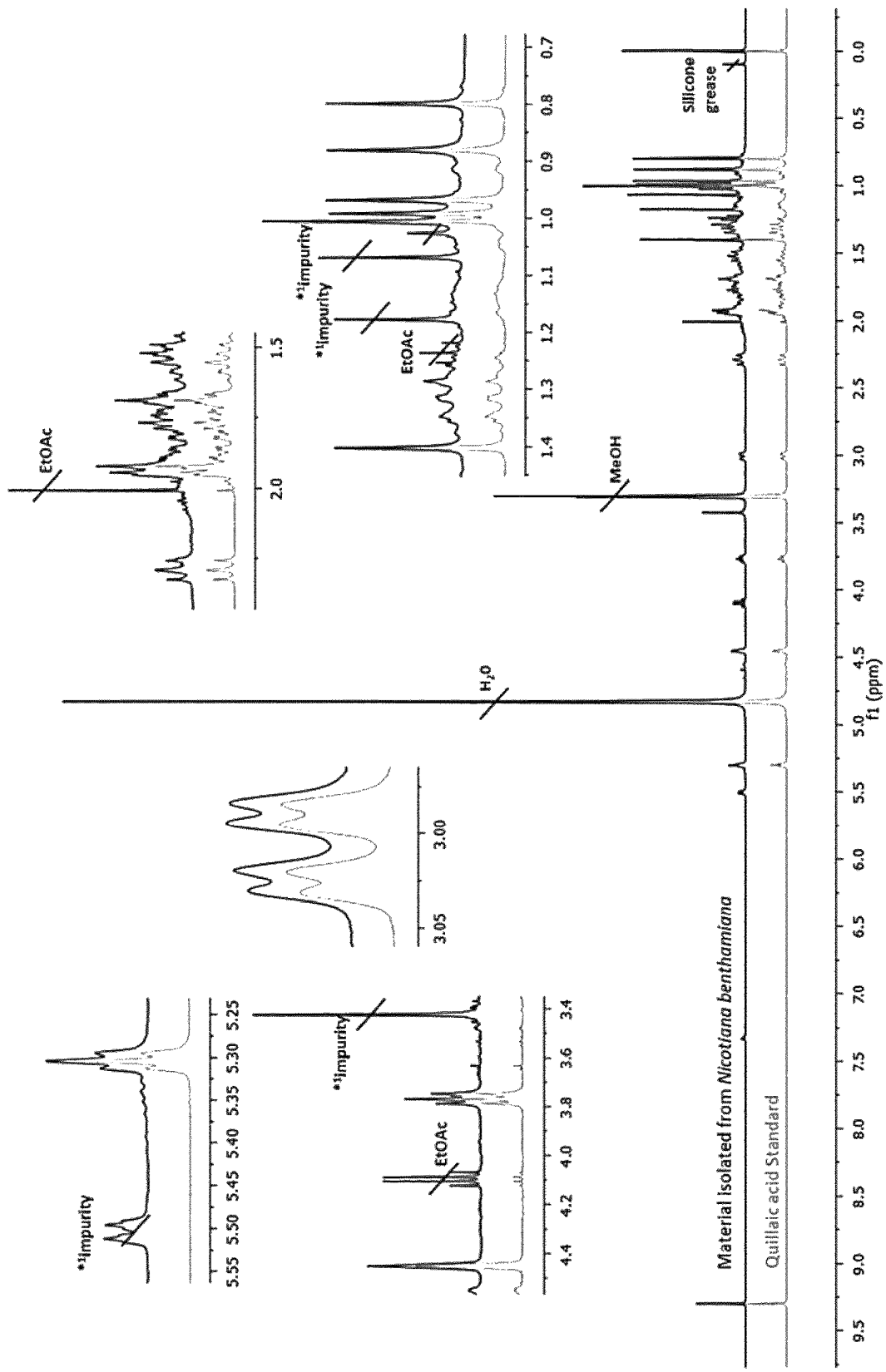

FIG. 16: $^{1}H\ NMR\ (methanol\ d_4)$ comparison of a quillaic acid standard (bottom) versus the isolated product from *N. benthamiana* (top).

EXAMPLES

Example 1—Mining for Candidate Quillaic Acid Biosynthetic Genes in a *Q. saponaria* Transcriptome Recently, a transcriptomic dataset from *Q. saponaria* was made available through the 1KP project [1]. This dataset is derived from HiSeq sequencing (Illumina) of *Q. saponaria* leaf tissue.

Although commercial sources of QS-21 are usually derived from bark, the leaf tissue has also been shown to be a substantial source of QS-21 and other saponins [2], so we reasoned the relevant biosynthetic genes might be present in this database. The transcriptome dataset was mined for potential biosynthetic genes.

β-Amyrin Synthase

The first candidate searched for was the β-amyrin synthase (bAS) OSC. Numerous bAS enzymes are characterised, including from related Fabales species.

A bAS enzyme from *Glycyrrhiza glabra* (Genbank ID Q9MB42.1) was used as a query to identify OSC sequences. This returned a single full-length sequence (OQHZ-2074321) predicted to be a triterpene synthase (henceforth referred to as QsbAS).

Other partial OSC sequences were also identified in this dataset, however these were predicted to be sterol (cycloartenol) synthases and were discounted.

The full nucleotide and predicted protein sequence of QsbAS are given as SEQ ID NOs: 1 and 2 in Sequence Appendix A.

β-Amyrin Oxidases

We surmised that a likely class of enzymes responsible for oxidation of β-amyrin would be cytochrome P450s (P450s). These enzymes are encoded by very large gene superfamilies with usually more than 200 representatives in a single plant genome.

Although function is often difficult to predict based on sequence homology, in recent years, the CYP716 family has emerged as a preeminent family of triterpene oxidases [3]. Previously 11 CYP716s had been characterised as β-amyrin C-28 oxidases (Sequence Appendix B). These P450s were isolated from taxonomically distinct species, (including Fabales species), suggesting that the C-28 β-amyrin oxidase in *Q. saponaria* may possibly be catalysed by a member of this family.

Furthermore CYP716 enzymes have also been shown to be capable of catalysing oxidation at other (non-C-28) positions around the β-amyrin scaffold, including one C-16α oxidase (CYP716Y1), from *Bupleurum falcatum* (Sequence Appendix B). Two full-length CYP716s were identified in the transcriptome dataset, using the *Medicago truncatula* C-28 oxidase CYP716A12 as a search query. These are OQHZ-2073932 and OQHZ-2012090 (which may be referred to herein as CYP716-2073932 and CYP716-2012090).

(Note that CYP716-2073932 has also been formally designated CYP716A224 by the P450 nomenclature committee [3]). The full nucleotide and predicted protein sequence of these CYP716s are given in as SEQ ID NOs: 3 and 4 in Sequence Appendix A.

Example 2—Cloning Candidate Genes from *Q. saponaria*

*Q. saponaria* trees were sourced from a nursery (Burncoose Nurseries, Cornwall) within the UK. RNA was extracted from the leaves and roots of a single tree using a Qiagen RNeasy Plant RNA extraction kit, with a modified protocol as detailed by [26]. This RNA was further used as a template for cDNA synthesis using Superscript III (Invitrogen) according to the manufacturer's instructions.

For amplification of target genes, primers were designed for each of the four genes described above (SEQ ID NOs: 1, 3, 5, and 7). For CYP716-2012090, two sets of primers were designed allowing cloning of both long and short isoforms of the protein, differing at the N-terminus by 21 amino acids. This was due to poor alignment of this region with other characterised CYP716s.

Each of the primers incorporated attB adapters at the 5' end to allow directional Gateway®-based cloning. These adapters are shown in italics at the 5' end, with the gene-specific sequences following in the 5'->3' direction.

| Primer name | Sequence 5' --> 3' |
|---|---|
| QsbAS1_F: | *GGGGACAAGTTTGTACAAAAAAGCAGGCTTA*ATGTGGAGGCTGAAGATAGCAGAAGG |
| QsbAS1_R: | *GGGGACCACTTTGTACAAGAAAGCTGGGTA*TTAAGGCAATGGAACCCGCCTCC |
| QsCYP716_2012090L_F: | *GGGGACAAGTTTGTACAAAAAAGCAGGCTTA*ATGATATATAATAATGATAGTAATGATAATG |
| QsCYP716_2012090S_F: | *GGGGACAAGTTTGTACAAAAAAGCAGGCTTA*ATGGATCCTTTCTTCATTTTTGGC |
| QsCYP716_2012090_R: | *GGGGACCACTTTGTACAAGAAAGCTGGGTA*TCATTGGTGCTTGTGAGG |
| QsCYP716_2073932_F: | *GGGGACAAGTTTGTACAAAAAAGCAGGCTTA*ATGGAGCACTTGTATCTCTCCCTTGTG |
| QsCYP716_2073932_R: | *GGGGACCACTTTGTACAAGAAAGCTGGGTA*TCAAGCTTTGTGAGGATAAAGGCGAAC |
| QsCYP714_2018687_F: | *GGGGACAAGTTTGTACAAAAAAGCAGGCTTA*ATGTGGTTCACAGTAGGATTGG |
| QsCYP714_2018687_R: | *GGGGACCACTTTGTACAAGAAAGCTGGGTA*TTAGAGCTTCTTCATGATGACATTG |

Two PCR reactions were performed for each gene, utilising either leaf or root cDNA as a template. As described above, two sets of PCRs were setup for CYP716-2012090 separate reactions, utilising different forward primers. PCRs were performed in a total volume of 50 μL using iProof (BioRad) with HF buffer according to the manufacturer's instructions. For amplification of OsbAS and CYP716 enzymes, PCR thermal cycling involved an initial denaturation step at 98° C. (30 sec), followed by 30 cycles of denaturation (98° C., 10 sec), annealing (50° C., 10 sec) and extension (72° C., 3 min), with a final extension at 72° C. (5 mins). These parameters were identical for amplification of the CYP714, except that the extension time during the 30 cycles was reduced to 2 mins.

Successful amplification of all genes was observed using the cDNA from both root and leaf tissues as a PCR template (FIG. 3). PCR products derived from the leaf cDNA were further purified and recombined into a pDONR207 Entry vector as described previously [5]. The resulting plasmids were sequenced by Eurofins Genomics to verify the presence and sequence of the inserted genes. A single representative plasmid was chosen for each gene and recombined into the binary vector pEAQ-HT-DEST1 [4], before transformation into competent *Agrobacterium tumefaciens* as described previously [5]. For transient expression in *N. benthamiana*, *A. tumefaciens* strains were grown and prepared for infiltration as described previously [5, 27].

Example 3—Transient Expression of *Q. saponaria* Genes in *N. benthamiana*

QsbAS is a Monofunctional β-Amyrin Synthase

Transient expression of the various cloned genes was performed in *N. benthamiana*. All combinations included coinfiltration of a strain carrying a feedback-insensitive truncated form of the *A. strigosa* HMG-CoA reductase (tHMGR). This enzyme has been demonstrated to increase triterpene content upon transient expression in *N. benthamiana* [5]. The sequences utilised are shown as SEQ ID Nos 29-32.

Leaves were harvested, extracted and analysed by GC-MS as described previously [5]. GC-MS analysis of QsbAS-expressing, leaves revealed the presence of compound identified as β-amyrin by comparison of the retention time and mass spectra of a β-amyrin standard (FIG. 4). No other new products were found in the chromatogram suggesting that QsbAS is a monofunctional β-amyrin synthase.

Discovery of the C-28 and C-16α Oxidases.

Next, QsbAS was tested with combinations of the various P450s. This revealed that both of the CYP716 enzymes showed activity towards β-amyrin. The CYP716-2073932 was found to be the C-28 oxidase and converted most of the β-amyrin to oleanolic acid. CYP716-2012090 converted a small amount of β-amyrin to a product putatively identified as 16α-hydroxy-β-amyrin (based on comparison to previously published mass spectra [6, 7](FIG. 5; FIG. 5s).

When these two CYP716 enzymes were combined, a third product was identified with an identical retention time and mass spectrum to echinocystic acid, an intermediate to quillaic acid consisting of β-amyrin plus the C-28 carboxylic acid and C-16α alcohol (FIG. 6A).

Example 4—Discovery of the C-23 Oxidase from *Q. saponaria*

Following the discovery of the C-28 and C-16α oxidases, attention was focused on the outstanding *Q. saponaria* C-23 oxidase. The identification of the C-28 and C-16α oxidases was facilitated by homology-based searches of known triterpene-oxidising P450s. Other candidates were considered based on homology to known triterpene oxidases, including two CYP72 family members (OQHZ-2012357 and OQHZ-2019977), for which a C-23 oxidase has been identified in the related Fabaceae species *Medicago truncatula*. However upon cloning and testing in planta neither of these candidates displayed obvious activity towards β-amyrin, or its C-28/C-16α oxidised derivatives (data not shown).

Consequently, it was deduced that the outstanding *Q. saponaria* C-23 oxidase may be within a P450 family not previously implicated in triterpene oxidation.

The 1 KP transcriptome data was therefore searched for all putative cytochrome P450s.

Approximately 150 P450-encoding contigs were found in the dataset. Out of these, 35 appeared to encode a full-length enzyme (approx. 1500 bp, see Table 5).

TABLE 5

List of all 35 full-length cytochrome P450s represented in the *Q. saponaria* 1KP dataset. Putative families/clans were assigned based on Genbank BLAST searches. Candidates anticipated to be involved in primary metabolism were not considered further. This resulted in 25 final candidates ("QuickRef" column). Note candidate names used here derive from the contig number of the independently assembled transcriptome. Consequently this number results in a different naming system from the one used previously for the CYP716/CYP72 enzymes.

| Quick Ref | Name | Putative Clan | Putative Family | Comments | Potential Candidate | Cloned/ Tested |
|---|---|---|---|---|---|---|
| — | >CYP51_c13199_g1_i1 | 51 | 51G | Sterol demethylase | | |
| — | >CYP701_c35443_g1_i2 | 71 | 701A | Gibberellin biosynthesis | | |
| 1 | >CYP704_c31665_g1_i1 | 86 | 704C | | ✓ | ✓ |
| 2 | >CYP704_c36842_g1_i1 | 86 | 704C | | ✓ | ✓ |
| 3 | >CYP704_c36842_g1_i3 | 86 | 704C | | ✓ | |
| — | >CYP707_c29564_g1_i1 | 85 | 707A | Abscisic acid deactivation | | |
| 4 | >CYP71_c35642_g1_i1 | 71 | 71D | | ✓ | ✓ |
| — | >CYP710_c19839_g1_i1 | 710 | 710A | Sterol C-22 desaturase | | |
| 5 | >CYP712_c19176_g1_i2 | 71 | 93A | | ✓ | ✓ |
| 6 | >CYP714_c36368_g1_i1 | 72 | 714C | Identical to 7 *Q. saponaria* | ✓ | ✓ |

TABLE 5-continued

List of all 35 full-length cytochrome P450s represented in the *Q. saponaria* 1KP dataset. Putative families/clans were assigned based on Genbank BLAST searches. Candidates anticipated to be involved in primary metabolism were not considered further. This resulted in 25 final candidates ("QuickRef" column). Note candidate names used here derive from the contig number of the independently assembled transcriptome. Consequently this number results in a different naming system from the one used previously for the CYP716/CYP72 enzymes.

| Quick Ref | Name | Clan | Putative Family | Comments | Potential Candidate | Cloned/Tested |
|---|---|---|---|---|---|---|
| 7 | >CYP714_c36368_g1_i2 | 72 | 714C | C23 oxidase 1KP: OHQZ-2018687 *Q. saponaria* | ✓ | ✓ |
| — | >CYP716_c41117_g1_i1 | 85 | 716A | C28 oxidase (CYP716-2073932) *Q. saponaria* | | |
| — | >CYP716_c23557_g1_i1 | 85 | 716A | C16a oxidase CYP716-2012090 | | |
| — | >CYP72_c34500_g2_i1 | 72 | 72A | Cloned (OQHZ-2012357) | | |
| — | >CYP721_c37141_g1_i1 | 72 | 734A | Brassinosteroid inactivation | | |
| — | >CYP73_c37071_g1_i2 | 71 | 73A | Transcinnamate-4-monooxygenase | | |
| 8 | >CYP74_c32585_g1_i1 | 71 | 74A | | ✓ | |
| 9 | >CYP75_c4825_g1_i1 | 71 | 75B | | ✓ | |
| 10 | >CYP75_c38772_g1_i1 | 71 | 75B | | ✓ | ✓ |
| 11 | >CYP77_c33191_g1_i1 | 71 | 77A | | ✓ | ✓ |
| 12 | >CYP78_c41068_g1_i1 | 71 | 78A | | ✓ | |
| 13 | >CYP81_c36730_g1_12 | 71 | 81E | | ✓ | |
| 14 | >CYP82_c34310_g1_i1 | 71 | 82C | | ✓ | |
| 15 | >CYP82_c36962_g1_i1 | 71 | 82C | | ✓ | |
| 16 | >CYP82_c37078_g1_i1 | 71 | 82D | Identical to 17 | ✓ | ✓ |
| 17 | >CYP82_c37078_g1_i2 | 71 | 82D | | ✓ | ✓ |
| 18 | >CYP82_c3431_g1_i1 | 71 | 82D | | ✓ | ✓ |
| 19 | >CYP84_c28124_g1_i1 | 71 | 84A | | ✓ | ✓ |
| 20 | >CYP86_c36146_g2_i1 | 86 | 86A | | ✓ | |
| 21 | >CYP89_c37100_g1_i1 | 71 | 89A | | ✓ | ✓ |
| — | >CYP90_c31983_g1_i1 | 85 | 90A | Brassinosteroid biosynthesis | | |
| 22 | >CYP92_c28169_g1_i1 | 71 | 71A | | ✓ | |
| 23 | >CYP94_c30674_g1_i1 | 86 | 94A | | ✓ | ✓ |
| 24 | >CYP94_c11979_g1_i1 | 86 | 94A | | ✓ | ✓ |
| 25 | >CYP96_c36742_g2_i1 | 86 | 86B | | ✓ | |

Amongst these full-length contigs were the C-28 and C-16α oxidases described above. It was therefore reasoned that the outstanding C-23 oxidase might also be represented within these sequences.

The 35 P450 candidates were further assigned putative clan and families based on their homology to named P450s from other species (Table 5). A number of the candidates were anticipated to be involved in primary metabolism (and shared a high degree of sequence conservation to enzymes from unrelated species such as *Arabidopsis*), and were subsequently eliminated from the list.

This gave a final list of 25 candidates, for which cloning primers were ordered. For easy reference, these are numbered 1-25 in Table 5 and described herein using these numbers.

PCR amplification of the 25 candidates was next attempted. As with the previous candidates, two PCRs were performed for each candidate using cDNA templates derived from both leaf (L) and root (R) respectively. Strong PCR products were successfully produced for 20 out of the 25 candidates (data not shown). These were subsequently purified (from the leaf cDNA template samples) and cloned into the Gateway® Entry vector pDONR207.

Candidates were sequenced to verify the correct gene had been cloned. In most cases the cloned sequences closely matched the anticipated sequence. Some redundancy was found amongst the clones; the sequences of #6 and #7 were found to be identical, as were #16 and #17. Upon checking the predicted sequence in the original transcriptomic data, it was realised that the contigs for these pairs were highly similar and primers had not been designed to distinguish between them. Regardless, the clones were treated as separate and cloned into the pEAQ-HT-DEST1 binary vector before transformation in *A. tumefaciens*.

The 15 candidates were next transiently expressed in *N. benthamiana*. The candidates were first assessed for their potential to oxidise β-amyrin by coexpression with the *Q. saponaria* β-amyrin synthase (QsbAS). No new products were detected in these samples by GC-MS analysis. Candidates were therefore further assessed for their ability to oxidise oleanolic acid, by coexpression with QsbAS and the C-28 oxidase (CYP716-2073932). This time, a distinct new product could be detected in extracts of leaves expressing candidates #6 and #7 (6 and 7 encode the same enzyme, as described above). The new products had identical retention times and mass spectra to a standard of 23-hydroxy-oleanolic acid (aka hederagenin). The enzyme encoded by candidate #7 is expected to be a CYP714 family member (yet to be formally named). Before the presently claimed priority date is it believed that no members of this family had been reported to be triterpene oxidases. Since the priority date other examples have been reported (see e.g. Kim et. al (2018). "A Novel Multifunctional C-23 Oxidase, CYP714E19, Is Involved in Asiaticoside Biosynthesis". Plant Cell Physiol.) 1200-1213.

The sequences are included in Appendix A as SEQ ID Nos 7 and 8.

As the C-23 candidates were derived from our own assembly of this data, the corresponding sequence in the 1 KP dataset were searched for by BLASTn (https://db.cng-b.org/blast4onekp/). Surprisingly, #7 is not represented by a full-length sequence in this database but several smaller contigs are returned (Table 6). The top hit from these is OHQZ-2018687, an 821 bp contig.

TABLE 6

List of contigs from the 1KP dataset which are returned from a BLASTn query of the C-23 oxidase. The top-scoring hit is OQHZ-2018687.

| Sequences producing significant alignments: | Length | Score (Bits) | E-Value |
|---|---|---|---|
| scaffold-OQHZ-2018687-Quillaja_saponaria | 821 bp | 1222 | 0.0 |
| scaffold-OQHZ-2012766-Quillaja_saponaria | 705 bp | 985 | 0.0 |
| scaffold-OQHZ-2018686-Quillaja_saponaria | 859 bp | 843 | 0.0 |
| scaffold-OQHZ-2012767-Quillaja_saponaria | 661 bp | 841 | 0.0 |
| scaffold-OQHZ-2022788-Quillaja_saponaria | 102 bp | 185 | 9e–46 |
| scaffold-OQHZ-2041685-Quillaja_saponaria | 129 bp | 170 | 2e–41 |
| scaffold-OQHZ-2022787-Quillaja_saponaria | 102 bp | 161 | 1e–38 |
| scaffold-OQHZ-2008891-Quillaja_saponaria | 323 bp | 95.1 | 1e–18 |
| scaffold-OQHZ-2072427-Quillaja_saponaria | 1046 bp | 66.2 | 6e–10 |
| scaffold-OQHZ-2049459-Quillaja_saponaria | 196 bp | 50.0 | 4e–05 |
| scaffold-OQHZ-2007159-Quillaja_saponaria | 892 bp | 50.0 | 4e–05 |

Example 5—Combinatorial Biosynthesis with *Q. saponaria* Enzymes Allows for Synthesis of Quillaic Acid in *N. benthamiana*

The β-amyrin synthase and C-28, C-16α and C-23 oxidases from *Q. saponaria* described above should be sufficient for production of quillaic acid when expressed together (see FIG. 2).

Prior to testing the C-23 oxidase from *Q. saponaria*, the other candidate genes from *Q. saponaria* were combined with C-23 β-amyrin oxidases characterised from other species i.e. CYP72A68v2 from *M. truncatula* (barrel medic) and CYP94D65 from *Avena strigosa* (black oat) (SEQ ID Nos 13-16).

In this first experiment, the QsbAS and two CYP716 enzymes from *Q. saponaria* were combined with the *M. truncatula* and *A. strigosa* C-23 oxidases using transient expression in *N. benthamiana* to determine whether quillaic acid could be observed in these samples. LC-MS-CAD analysis revealed that both sets of combinations tHMGR/QsbAS/CYP716-2073932/CYP716-2012090/CYP72A68v2 tHMGR/QsbAS/CYP716-2073932/CYP716-2012090/CYP94D65 resulted in appearance of novel products which matched the retention time and mass spectrum of a quillaic acid standard (results not shown).

The abundance of quillaic acid appeared to be highest in the sample expressing CYP72A68v2.

Other related products were also observed in these samples: In the combination expressing the oat C-23 oxidase (CYP94D65), the most abundant new peak was identified as cauphyllogenin (C-23 alcohol instead of the aldehyde seen in quillaic acid), while the *Medicago* C-23 oxidase (CYP72A68v2) gave rise to substantial accumulation of 16α-hydroxy gypsogenin (C-23 carboxyllic acid instead of the aldehyde seen in quillaic acid).

To verify that quillaic acid could be produced in *N. benthamiana* with the exclusive use of the *Q. saponaria* enzymes, the OsbAS enzyme was transiently expressed with various combinations of the P450s. As expected, analysis of leaves coexpressing OsbAS with all P450s resulted in appearance of a peak which matched the retention time and mass spectrum of a quillaic acid standard. This peak was absent in samples from leaves expressing any less than the full pathway (FIG. 7).

Furthermore, a comparison was made between the present sample expressing the full *Q. saponaria* complement of enzymes, versus the equivalent (stored) samples where C-23 oxidases from *M. truncatula* and oat had been used. This revealed that the amount of quillaic acid appeared to be highest in the sample expressing the *Q. saponaria* C-23 oxidase (FIG. 8). The sample expressing the *Q. saponaria* C-23 oxidase also appeared to contain significantly less of the unwanted putative side products cauphyllogenin and 16α-hydroxy gypsogenic acid (FIG. 8). These metabolites reflect the different C-23 oxidase specificity of the oat and *Medicago* enzymes, which predominantly make the C-23 alcohol and acid, respectively. Hence, the *Q. saponaria* C-23 oxidase appears to be much more specific for the C-23 aldehyde, reflecting its expected function in QS-21 biosynthesis.

Example 6—Expressing *Q. saponaria* Genes in Yeast

*Saccharomyces cerevisiae* may be utilised as a host chassis for commercial QA production.

We therefore demonstrated cloned *Quillaja* genes are active in this host. A strain of *S. cerevisiae* derived from S288C (Genotype: MATa/MATα; ura3Δ0/ura3Δ0; leu2Δ0/eu2Δ0; his3Δ1/his3Δ1; met15Δ0/MET15; LYS2/lys2Δ0; YHR072w/YHR072w::kanM) was used which contains three auxotrophic selection markers (-URA/-HIS/-LEU) allowing for expression of genes from up to three plasmids.

Three Gateway-compatible yeast expression vectors were employed, including pYES-DEST52 (uracil selection), pAG423 (histidine selection) and pAG435 (leucine selection). The *Q. saponaria* enzymes were recombined into these vectors as described in Table 7. Briefly, the β-amyrin synthase (QsbAS) was recombined into the pYES-DEST52 vector, while the C-28 oxidase (CYP716-2073932) and C-16α oxidase (both long (L) and short (S) isoforms) were recombined into pAG423.

To enhance the efficiency of functioning of the cytochrome P450s, the third plasmid (pAG435) was used to express the *Arabidopsis thaliana* cytochrome P450 reductase 2 (AtATR2) enzyme. This serves as a coenzyme for reducing plant P450s back to an active state following substrate oxidation. All vectors contain galactose-inducible promoters for expression of the inserted genes.

TABLE 7

List of yeast strains generated.

| Strain Number | Media | Vectors | | |
|---|---|---|---|---|
| | | pYES2 URA3 | pAG423 HIS3 | pAG435 LEU2 |
| 62 | -URA | QsbAS | — | — |
| 63 | -URA -LEU -HIS | QsbAS | QsCYP716-2073932 | AtATR2 |
| 64 | -URA -LEU -HIS | QsbAS | QsCYP716-2012090-long | AtATR2 |
| 65 | -URA -LEU -HIS | QsbAS | QsCYP716-2012090-short | AtATR2 |

The yeast strains were cultured in synthetic yeast media with galactose and incubated for 2 days at 30° C. Strains were pelleted by centrifugation, saponified and metabolites were extracted with ethyl acetate. GC-MS analysis revealed that all strains accumulated a peak at 10.6 minutes which was identified as β-amyrin (FIG. 9). Strain 63, (expressing the C-28 oxidase) was found to accumulate small amounts of additional products which were identified as C-28 oxidised β-amyrin derivatives, including oleanolic acid (12.01 min) and intermediate C-28 alcohol erythrodiol (11.51 min) (FIG. 9, $2^{nd}$ trace down). No products were identified in strain 64 or 65 (expressing C-16α oxidase isoforms) which could readily be identified as 16-hydroxy-β-amyrin implying this may not be optimal substrate for this enzyme.

The above data demonstrates that yeast can be engineered to produce quillaic acid precursors.

Example 7—Production of QA by Stable Transformation

Triterpenes have previously been produced using engineered transgenic plant lines (e.g. *Arabidopsis*, Wheat). A series of Golden Gate [23] vectors which allow for construction of multigene vectors and allow integration of an entire pathway into a single locus have been reported. These can be applied analogously to the present invention, in the light of the disclosure herein.

Example 8—Conclusions from Examples 1 to 7

Quillaic acid is a triterpenoid and a key precursor to the saponin QS-21 produced by *Quillaja* saponaria.

Here, four enzymes (a β-amyrin synthase and C-16α, C-23 and C-28 oxidases) from *Q. saponaria* were identified which were capable of production of quillaic acid when transiently expressed in *Nicotiana benthamiana*. These enzymes are predicted to be involved in the early steps of the QS-21 biosynthetic pathway, required for generation of the quillaic acid scaffold (FIG. 1).

The identity of the products described herein were validated through use of authentic standards, giving a high degree of confidence in these results.

The activity of the β-amyrin synthase (QsbAS) and three cytochrome P450 monoxygenases which oxidise β-amyrin at the C-28, C-23 and C-16α positions (referred to herein as CYP716-2073932, CYP714-7 and CYP716-2012090, respectively) in the biosynthesis of quillaic acid is shown schematically in FIG. 12.

Example 9—Estimating Production of Quillaic Acid in *N. benthamiana*

To estimate quillaic acid production in *N. benthamiana* following transient expression, an analysis was carried out by LC-CAD. Agroinfiltration was performed as previously described using the *Q. saponaria* β-amyrin synthase and C-16α, C-23 and C-28 oxidases. As a control, leaves infiltrated with only two (C-23 and C-28) oxidases were used and accumulate gypsogenin instead of quillaic acid (FIG. 12).

The oat HMG-CoA reductase (tHMGR) was also included in all infiltrations as it increases production of β-amyrin. Representative chromatograms from these samples are shown in FIG. 13. Three leaves from different plants were used for each test condition as biological replicates.

To estimate production of quillaic acid in these leaves, the area of the quillaic acid peak was compared to that of the internal standard (included at 1.1 mg/g dry leaf weight). The average value from the three replicates was found to be 1.44 mg/g.

Example 10—Purification of Quillaic Acid from *N. benthamiana*

To determine unambiguously that quillaic acid production had been achieved in *N. benthamiana*, purification of the product was undertaken.

A total of 209 *N. benthamiana* plants were vacuum infiltrated with *A. tumefaciens* carrying the pEAQ-HT-DEST1 constructs harbouring the *Q. saponaria* β-amyrin synthase, C-16α, C-23 and C-28 oxidases. The oat tHMGR was also included to boost yields. Leaves were harvested four days after infiltration yielding 150.3 g dry material after lyophilisation. Metabolites were extracted with ethanol using a Buchi Speed Extractor E-914 and several rounds of silica gel flash chromatography was used to isolate a total of 30 mg of product. The isolated product was found to have an identical retention time and mass spectrum to that of an authentic quillaic acid standard (Extrasynthese) by LC-MS (FIG. 14) and GC-MS (FIG. 15). Furthermore, $^1$H NMR spectroscopic analysis of the isolated product was also in accordance with the quillaic acid standard (FIG. 16).

This confirms that quillaic acid can be produced through transient expression in *N. benthamiana* through transient expression of the *Q. saponaria* enzymes. The isolated yield of the product was in the region of 0.2 mg/g dry weight, although some minor impurities were detected in the sample. This yield is lower than the estimated yield from LC-CAD in Example 9, indicating losses of the product during this isolation process. Nevertheless this demonstrates that practical quantities of quillaic acid can be produced and isolated from *N. benthamiana* using the presently characterised enzymes.

Methods

Infiltration

Agroinfiltration was performed using a needleless syringe as previously described (Reed et al., 2017). All genes were expressed from pEAQ-HT-DEST1 binary expression vectors (Sainsbury et al., 2009) in *A. tumefaciens* LBA4404. All plants co-expressed the oat tHMGR, the *Quillaja* β-amyrin synthase (QsbAS), and β-amyrin C-28 (CYP716-2073932) and C-16α (CYP716-2012090S) oxidases. For quillaic acid production the C-23 (CYP714-7) oxidase was also co-expressed while green fluorescent protein (GFP) was used instead for controls. Cultivation of bacteria and plants is as described in (Reed et al., 2017). Three plants were infiltrated per test condition and analysed separately as biological replicates.

LC-MS Analysis

Leaves were harvested 5 days after agroinfiltration and freeze-dried. Freeze-dried leaf material (10 mg per sample) was ground at 1000 rpm for 1 min (Geno/Grinder 2010, Spex SamplePrep). Extractions were carried out in 550 µL 80% methanol with 20 µg/mL of digitoxin (internal standard; Sigma) for 20 min at 40° C., with shaking at 1400 rpm (Thermomixer Comfort, Eppendorf). The sample was partitioned twice with 400 µL hexane. The aqueous phase was dried under vacuum at 40° C. (EZ-2 Series Evaporator, Genevac). Dried material was resuspended in 75 µL of 100% methanol and filtered at 12, 500 g for 30 sec (0.2 µm, Spin-X, Costar). Filtered samples were transferred to glass vials and analysed as detailed below.

Preparation of *N. benthamiana* Leaf Extracts

Analysis was carried out using a Prominence HPLC system with single quadrupole mass spectrometer LCMS-2020 (Shimadzu) and Corona Veo RS Charged Aerosol Detector (CAD) (Dionex). Detection: MS (dual ESI/APCI ionization, DL temp 250° C., neb gas flow 15 L·min-1, heat block temp 400° C., spray voltage Pos 4.5 kV, Neg −3.5 kV) CAD: data collection rate 10 Hz, filter constant 3.6 s, 925 evaporator temp. 35° C., ion trap voltage 20.5 V. Method: Solvent A: [$H_2O$+0.1% formic acid] Solvent B: [acetonitrile ($CH_3CN$)+0.1% formic acid. Injection volume: 10 µL. Gradient: 15% [B] from 0 to 1.5 min, 15% to 60% [B] from 1.5 to 26 min, 60% to 100% [B] from 26 to 26.5 min, 100% [B] from 26.5 to 28.5 min, 100% to 15% [B] from 28.5 to 29 min, 35% [B] from 29 to 30 min. Method was performed using a flow rate of 0.3 mL·min-1 and a Kinetex column 2.6 µm XB-C18 100 Å, 50×2.1 mm (Phenomenex).

Analysis of *N. benthamiana* Leaf Extracts

Analysis was performed using LabSolutions software (Shimadzu). To provide an estimate of product yields, the area of the peak for quillaic acid (as determined by CAD) was divided by that of the internal standard (digitoxin, 1.1 µg/mg dry leaf tissue). Results were averaged from the three replicates. A minor peak for an endogenous *N. benthamiana* product with the same retention time as quillaic acid was observed in controls (calculated average 0.25 µg/mg). Therefore his value was subtracted from the estimated quillaic acid yield.

Large Scale Infiltration

Agroinfiltration was carried out as detailed above using tHMGR, QsbAS, CYP716-2073932, CYP716-2012090S and CYP714-7 oxidases. A total of 209 plants were infiltrated by vacuum as previously described (Reed et al., 2017) and were harvested after four days.

Purification of Quillaic Acid from *N. benthamiana*

Leaves from the large scale infiltration were harvested, lyophilised and extraction was performed using a SpeedExtractor E-914 (Buchi) as detailed in (Reed et al., 2017) with the exception that the program involved four cycles (100° C. and 130 bar pressure). Cycle one (hexane) had zero hold time, and cycles two to four (ethanol) had 5 min hold times. The run finished with a 2 min solvent flush and 6 min $N_2$ flush. The hexane portion of the extraction was discarded and the ethanol portion was used for subsequent flash chromatography, performed using an Isolera One (Biotage) with details of individual columns given below. Fractions were checked for quillaic acid after each column by GC-MS and thin layer chromatography (TLC) as detailed in (Reed et al., 2017). At each stage, the purest fractions were pooled and dried onto silica gel 60 (Material Harvest) for loading onto the subsequent column. Column 1: SNAP Ultra 50 g (Biotage), flow rate: 100 mL/min, 90 mL fractions with the following gradient: Solvent A: [hexane]Solvent B: [ethyl acetate]; gradients: 5% [B] to 100% [B] over 10 column volumes, and held at 100% [B] for a further 5 column volumes. Column 2: SNAP Ultra 50 g (Biotage), flow rate 100 mL/min, 90 mL fractions with the following gradient: Solvent A: [dichloromethane]Solvent B: [ethyl acetate]; 10% [B] to 60% [B] over 10 column volumes, and held at 100% [B] for a further 2 column volumes. Column 3: SNAP Ultra 10 g (Biotage), flow rate: 36 mL/min, 17 mL fractions with same gradient as column 2. Following column 3 the fractions were treated with activated charcoal to remove coloured impurities and loaded onto column 4. Column 4: SNAP Ultra 10 g column (Biotage) (36 mL/min, 17 mL fractions) with an isocratic mobile phase 15% ethyl acetate in dichloromethane over 20 column volumes. The pooled fractions were treated with a small amount of HCl (400 µL of conc HCl in −40 mL ethanol) which helped to reduce streaking on the TLC plate. Column 5: SNAP Ultra 10 g column (Biotage) (36 mL/min, 17 mL fractions) with an isocratic mobile phase 15% ethyl acetate in dichloromethane over 30 column volumes with a final flush of 100% ethyl acetate over 5 column volumes. The purest fractions were pooled and dried to yield a 30 mg of a white powder with small amounts of yellow impurities. This was analysed by GC-MS, LC-MS and NMR as below.

GC-MS, LC-MS and NMR Analysis of Purified Quillaic Acid.

GC-MS analysis was performed as described in (Reed et al., 2017). LC-MS analysis was performed as described above for quillaic acid quantification. NMR spectra were recorded in Fourier transform mode at a nominal frequency of 400 MHz for $^1$H NMR in deuterated methanol. For each method of analysis a quillaic acid standard (Extrasynthese) was used for comparison.

References for Materials and Methods

Reed J, Stephenson M J, Miettinen K, Brouwer B, Leveau A, Brett P, Goss R J M, Goossens A, O'Connell M A, Osbourn A. 2017. A translational synthetic biology platform for rapid access to gram-scale quantities of novel drug-like molecules. *Metab Eng* 42: 185-193.

Sainsbury F, Thuenemann E C, Lomonossoff G P. 2009. pEAQ: versatile expression vectors for easy and quick transient expression of heterologous proteins in plants. *Plant Biotechnol J* 7(7): 682-693.

OTHER REFERENCES

1. Johnson, M. T. J., et al., *Evaluating Methods for Isolating Total RNA and Predicting the Success of Sequencing Phylogenetically Diverse Plant Transcriptomes*. PLOS ONE, 2012. 7(11): p. e50226.
2. Schlotterbeck, T., et al., *The Use of Leaves from Young Trees of Quillaja saponaria (Molina) Plantations as a New Source of Saponins*. Economic Botany, 2015. 69(3): p. 262-272.
3. Miettinen, K., et al., *The ancient CYP716 family is a major contributor to the diversification of eudicot triterpenoid biosynthesis*. Nat Commun, 2017. 8: p. 14153.
4. Sainsbury, F., E. C. Thuenemann, and G. P. Lomonossoff, *pEAQ: versatile expression vectors for easy and quick transient expression of heterologous proteins in plants*. Plant Biotechnol J, 2009. 7(7): p. 682-93.
5. Reed, J., et al., *A translational synthetic biology platform for rapid access to gram-scale quantities of novel drug-like molecules*. Metab Eng, 2017.
6. Moses, T., et al., *Combinatorial biosynthesis of sapogenins and saponins in Saccharomyces cerevisiae using a C-16α hydroxylase from Bupleurum falcatum*. Proc Nati Acad Sci USA, 2014. 111(4): p. 1634-39.

7. Moses, T., et al., *Unravelling the Triterpenoid Saponin Biosynthesis of the African Shrub Maesa lanceolata*. Mol Plant, 2014. 8: p. 122-35.
8. Fukushima, E. O., et al., *Combinatorial biosynthesis of legume natural and rare triterpenoids in engineered yeast*. Plant Cell Physiol, 2013. 54(5): p. 740-9.
9. Fukushima, E. O., et al., *CYP716A subfamily members are multifunctional oxidases in triterpenoid biosynthesis*. Plant Cell Physiol, 2011. 52(12): p. 2050-61.
10. Carelli, M., et al., *Medicago truncatula CYP716A12 is a multifunctional oxidase involved in the biosynthesis of hemolytic saponins*. Plant Cell, 2011. 23(8): p. 3070-81.
11. Han, J. Y., et al., *The involvement of β-amyrin 28-oxidase (CYP716A52v2) in oleanane-type ginsenoside biosynthesis in Panax ginseng*. Plant Cell Physiol, 2013. 54(12): p. 2034-46.
12. Fiallos-Jurado, J., et al., *Saponin determination, expression analysis and functional characterization of saponin biosynthetic genes in Chenopodium quinoa leaves*. Plant Sci, 2016. 250: p. 188-97.
13. Khakimov, B., et al., *Identification and genome organization of saponin pathway genes from a wild crucifer, and their use for transient production of saponins in Nicotiana benthamiana*. Plant J, 2015. 84(3): p. 478-90.
14. Andre, C. M., et al., *Multifunctional oxidosqualene cyclases and cytochrome P450 involved in the biosynthesis of apple fruit triterpenic acids*. New Phytol, 2016. 211(4): p. 1279-94.
15. Huang, L., et al., *Molecular characterization of the pentacyclic triterpenoid biosynthetic pathway in Catharanthus roseus*. Planta, 2012. 236(5): p. 1571-81.
16. Xu, G., et al., *A novel glucuronosyltransferase has an unprecedented ability to catalyse continuous two-step glucuronosylation of glycyrrhetinic acid to yield glycyrrhizin*. New Phytologist, 2016. 212(1): p. 123-135.
17. Shibuya, M., et al., *Identification and characterization of glycosyltransferases involved in the biosynthesis of soyasaponin I in Glycine max*. FEBS Lett, 2010. 584(11): p. 2258-64.
18. Wang, P., et al., *Synthesis of the potent immunostimulatory adjuvant QS-21A*. J Am Chem Soc, 2005. 127(10): p. 3256-7.
19. Moses, T., et al., *Comparative analysis of CYP93E proteins for improved microbial synthesis of plant triterpenoids*. Phytochemistry, 2014. 108: p. 47-56.
20. Dai, Z., et al., *Producing aglycons of ginsenosides in bakers' yeast*. Sci Rep, 2014. 4: p. 3698.
21. Dai, Z., et al., *Metabolic engineering of Saccharomyces cerevisiae for production of ginsenosides*. Metab Eng, 2013. 20(0): p. 146-56.
22. Salmon, M., et al., *A conserved amino acid residue critical for product and substrate specificity in plant triterpene synthases*. Proc Natl Acad Sci USA, 2016. 113(30): p. E4407-14.
23. Engler, C., et al., *A golden gate modular cloning toolbox for plants*. ACS Synth Biol, 2014. 3(11): p. 839-43.
24. Mugford, S. T., et al., *Modularity of plant metabolic gene clusters: a trio of linked genes that are collectively required for acylation of triterpenes in oat*. Plant Cell, 2013. 25(3): p. 1078-92.
25. Paddon, C. J., et al., *High-level semi-synthetic production of the potent antimalarial artemisinin*. Nature, 2013. 496(7446): p. 528-32.
26. MacKenzie, D. J., et al., Improved RNA Extraction from Woody Plants for the Detection of Viral Pathogens by Reverse Transcription-Polymerase Chain Reaction. *Plant Disease*, 1997. 81(2): p. 222-226.
27. Sainsbury, F. and G. P. Lomonossoff, Transient expressions of synthetic biology in plants. Current Opinion in Plant Biology, 2014. 19(0): p. 1-7.

Appendix A: Sequence Tables and Sequences

TABLE 1

*Q. saponaria* sequences
Clone number refers to the contig number from
the original 1KP transcriptome assembly
(https://db.cngb.org/blast4onekp/)

| Activity | SID | Clone/name | Length | Other comment |
|---|---|---|---|---|
| QsbAS | 1 | OQHZ-2074321 | 2277 bp | *Q. saponaria* |
| | 2 | | 758 aa | β-amyrin synthase, QsbAS1 |
| C-28 | 3 | OQHZ-2073932 | 1443 bp | *Q. saponaria* β-amyrin - |
| | 4 | CYP716A224 | 480 aa | C-28 oxidase |
| C-16α | 5 | OQHZ-2012090 | 1506 bp | *Q. saponaria* β-amyrin/ |
| | 6 | CYP716 | 501 aa | oleanolic acid C-16a oxidase |
| C-23 | 7 | OQHZ-2018687 | 1524 bp | *Q. saponaria* oleanolic |
| | 8 | CYP714 | 507 aa | acid C-23 oxidase |

TABLE 2

Non-*Q. saponaria* sequences
Cytochrome P450s which oxidise β-amyrin (or derivatives thereof) at the relevant positions (16α, 28, 23) found in quillaic acid. Enzymes named in bold have been tested by transient expression in *N. benthamiana* and found to generate products consistent with those reported by the referenced studies.
Initials preceding gene name are species as follows: As - *Avena strigosa*, At - *Arabidopsis thaliana*, Bf - *Bupleurum falcatum*, Bv - *Barbarea vulgaris*, Cq - *Chenopodium quinoa*, Cr - *Catharanthus roseus*, Md - *Malus domestica*, Ml - *Maesa lanceolata*, Mt - *Medicago truncatula*, Pg - *Panax ginseng*, Vv - *Vitis vinifera*.

| | Gene | Enzyme preferred Substrate | Genbank ID (nucleotide) | Reference (P lab). |
|---|---|---|---|---|
| Table 2a | | | | |
| C-16α | 9 nt BfCYP716Y1 | β-amyrin | KC963423.1 | [6] (Goosens lab, VIB, Ghent, Belgium) |
| | 10 aa | | | |
| | 11 nt MlCYP87D16 | β-amyrin | KF318735.1 | [7] (Goosens lab, VIB, Ghent, Belgium) |
| | 12 aa | | | |

TABLE 2-continued

Non-*Q. saponaria* sequences
Cytochrome P450s which oxidise β-amyrin (or derivatives thereof) at the relevant positions (16α, 28, 23) found in quillaic acid. Enzymes named in bold have been tested by transient expression in *N. benthamiana* and found to generate products consistent with those reported by the referenced studies.
Initials preceding gene name are species as follows: As - *Avena strigosa*, At - *Arabidopsis thaliana*, Bf - *Bupleurum falcatum*, Bv - *Barbarea vulgaris*, Cq - *Chenopodium quinoa*, Cr - *Catharanthus roseus*, Md - *Malus domestica*, Ml - *Maesa lanceolata*, Mt - *Medicago truncatula*, Pg - *Panax ginseng*, Vv - *Vitis vinifera*.

|  |  | Gene | Enzyme preferred Substrate | Genbank ID (nucleotide) | Reference (P lab). |
|---|---|---|---|---|---|
| Table 2b |  |  |  |  |  |
| C-23 | 13 nt 14 aa | MtCYP72A68v2 | Oleanolic acid | AB558150.1 | [8] (Muranaka Lab, Osaka, Japan). |
|  | 15 nt 16 aa | AsCYP94D65 | β-amyrin | UNPUBLISHED | UNPUBLISHED (Osbourn Lab, JIC) |
| Table 2c |  |  |  |  |  |
| C-28 | 17 nt 18 aa | MtCYP716A12 | β-amyrin | FN995113.1 | [9, 10] (Muranaka Lab, Osaka, Japan/ Calderini Lab, IGV, Perugia Italy) |
| Table 2d |  |  |  |  |  |
|  | 19 | VvCYP716A15 | β-amyrin |  | [9] |
|  | 20 | VvCYP716A17 | β-amyrin | AB619803.1 | [9] |
|  | 21 | PgCYP716A52v2 | β-amyrin | JX036032.1 | [11] |
|  | 22 | MlCYP716A75 | β-amyrin | KF318733.1 | [7] |
|  | 23 | CqCYP716A78 | β-amyrin | KX343075.1 | [12] |
|  | 24 | CqCYP716A79 | β-amyrin | KX343076.1 | [12] |
|  | 25 | BvCYP716A80 | β-amyrin | KP795926.1 | [13] |
|  | 26 | BvCYP716A81 | β-amyrin | KP795925.1 | [13] |
|  | 27 | MdCYP716A175 | β-amyrin | XM_008392874.2 | [14] |
|  | 28 | CrCYP716AL1 | β-amyrin | JN565975.1 | [15] |

TABLE 3

Accessory enzymes

| SEQ ID NO: | Name |
|---|---|
| 29 | AsHMGR (Avena strigosa HMG-CoA reductase) coding sequence (1689 bp): |
| 30 | AsHMGR (Avena strigosa HMG-CoA reductase) translated nucleotide sequence (562 aa): |
| 31 | AstHMGR (Avena strigosa truncated HMG-CoA reductase) coding sequence (1275 bp): |
| 32 | AstHMGR (Avena strigosa truncated HMG-CoA reductase) translated nucleotide sequence (424 aa): |
| 33 | AsSQS (Avena strigosa squalene synthase) coding sequence (1212 bp): |
| 34 | AsSQS (Avena strigosa squalene synthase) translated nucleotide sequence (403 aa): |
| 35 | AtATR2 (Arabidopsis thaliana cytochrome P450 reductase 2) coding sequence (2325 bp): |
| 36 | AtATR2 (Arabidopsis thaliana cytochrome P450 reductase 2) translated nucleotide sequence (774 aa): |

TABLE 4

Comparisons between the gene sequences as found in the 1KP dataset and the sequenced clones obtained by PCR from the *Q. saponaria* plants in the present disclosure

| Name | 1kP Contig Number | Nucleotide substitutions | Amino acid substitution |
|---|---|---|---|
| QsbAS | OQHZ-2074321 | C1020G | F340L |
|  |  | G1635A | — |
| C-28 | OQHZ-2073932 | G904A | I304V |
|  |  | G1296A | — |
|  |  | T1305C | — |
|  |  | T1311C | — |
|  |  | T1314A | — |
|  |  | A1317C | — |
|  |  | T1326C | — |
|  |  | A1347G | — |
|  |  | G1359C | — |
|  |  | T1363C | — |
| C-16 | OQHZ-2012090 | G1368A | — |
|  |  | G1371A | — |
|  |  | G1374T | — |
|  |  | G1377T | — |
|  |  | T1395G | — |
|  |  | A1397C | K466T |
|  |  | A1407T | K469N |
|  |  | G1412A | G471E |
|  |  | A1413G | — |
|  |  | T1467C | — |
| C-23 | OQHZ-2018687 | A564T | — |

TABLE 8

Pairwise alignments of the 18 P450s were made using Clustal Omega (version 1.2.4-accessed through https://www.ebi.ac.uk). Numbers in the table represent percentage amino acid identity between genes. Sequences are organised according to function and the *Q. saponaria* genes characterised herein are given in bold. All pairwise values are represented twice, therefore redundant sequences are shown in the upper right of the table with a grey background. The Table is split across pages for ease of presentation.

|  |  | C-16α oxidases | | | C-23 oxidases | | |
|---|---|---|---|---|---|---|---|
|  |  | QsCYP 716 (C16) | BfCYP 716Y1 | MlCYP 87D16 | QsCYP 714(C23) | MtCYP 72A68v2 | AsCYP 94D65 |
| C-16α oxi-dases | QsCYP716 (C16) | 100.00 | 42.86 | 24.78 | 17.94 | 17.76 | 19.26 |
|  | BfCYP716Y1 | 42.86 | 100.00 | 23.67 | 21.44 | 20.97 | 19.82 |
|  | MlCYP87D16 | 24.78 | 23.67 | 20.23 | 20.23 | 17.69 | 18.43 |
| C-23 oxi-dases | QsCYP714 (C23) | 17.94 | 21.44 | 20.23 | 100.00 | 30.32 | 22.46 |
|  | MtCYP72A68v2 | 17.76 | 20.97 | 17.69 | 30.32 | 100.00 | 18.82 |
|  | AsCYP94D65 | 19.26 | 19.82 | 18.43 | 22.46 | 18.82 | 100.00 |
| C-28 oxi-dases | QsCYP716 (C28) | 60.25 | 48.10 | 24.51 | 19.55 | 19.08 | 21.81 |
|  | MtCYP716A12 | 29.87 | 47.35 | 25.44 | 19.00 | 19.21 | 20.80 |
|  | VvCYP716A15 | 59.00 | 47.68 | 24.95 | 18.65 | 18.42 | 21.81 |
|  | VvCYP716A17 | 59.21 | 47.89 | 24.51 | 19.33 | 18.64 | 22.03 |
|  | PgCYP716A52v2 | 58.66 | 46.74 | 26.64 | 20.63 | 20.35 | 20.66 |
|  | MlCYP716A75 | 56.16 | 45.17 | 25.05 | 18.40 | 19.26 | 20.92 |
|  | CqCYP716A78 | 58.49 | 47.16 | 24.40 | 20.54 | 21.37 | 20.70 |
|  | CqCYP716A79 | 58.49 | 46.95 | 24.40 | 20.32 | 21.37 | 20.93 |
|  | BvCYP716A80 | 51.60 | 43.01 | 24.17 | 17.23 | 19.87 | 20.71 |
|  | BvCYP716A81 | 51.17 | 43.23 | 23.73 | 17.23 | 19.64 | 21.16 |
|  | MdCYP716A175 | 56.58 | 46.85 | 26.04 | 20.22 | 19.08 | 20.48 |
|  | CrCYP716AL1 | 58.58 | 46.62 | 25.66 | 20.72 | 19.56 | 20.97 |

|  |  | C-28 oxidases | | | | | | | | | | |
|---|---|---|---|---|---|---|---|---|---|---|---|---|
|  |  | QsCYP 716 (C28) | MtCYP 716A12 | VvCYP 716A15 | VvCYP 76A17 | PgCYP 716A52v2 | MlCYP 716A75 | CqCYP 716A78 | CqCYP 716A79 | BvCYP 716A80 | BvCYP 716A81 | MdCYP 716A175 | CrCYP 716AL1 |
| C-16α oxi-dases | QsCYP716 (C16) | 60.25 | 59.87 | 59.00 | 59.21 | 58.66 | 56.16 | 58.49 | 58.49 | 51.60 | 51.17 | 56.58 | 58.58 |
|  | BfCYP716Y1 | 48.10 | 47.35 | 47.68 | 47.89 | 46.74 | 45.17 | 47.16 | 46.95 | 43.01 | 43.23 | 46.85 | 46.62 |
|  | MlCYP87D16 | 24.51 | 25.44 | 24.95 | 24.51 | 26.64 | 25.05 | 24.40 | 24.40 | 24.17 | 23.73 | 26.04 | 25.66 |
| C-23 oxi-dases | QsCYP714 (C23) | 19.55 | 19.00 | 18.65 | 19.33 | 20.63 | 18.40 | 20.54 | 20.32 | 17.23 | 17.23 | 20.22 | 20.72 |
|  | MtCYP72A68v2 | 19.08 | 19.21 | 18.42 | 18.64 | 20.35 | 19.26 | 21.37 | 21.37 | 19.87 | 19.64 | 19.08 | 19.56 |
|  | AsCYP94D65 | 21.81 | 20.80 | 21.81 | 22.03 | 20.66 | 20.92 | 20.70 | 20.93 | 20.71 | 21.16 | 20.48 | 20.97 |
| C-28 oxi-dases | QsCYP716 (C28) | 100.00 | 79.25 | 80.83 | 80.83 | 75.42 | 72.08 | 73.58 | 73.38 | 62.34 | 61.28 | 77.08 | 76.62 |
|  | MtCYP716A12 | 79.25 | 100.00 | 75.47 | 75.26 | 73.17 | 67.51 | 68.70 | 69.33 | 60.90 | 60.04 | 73.38 | 73.11 |
|  | VvCYP716A15 | 80.83 | 75.47 | 100.00 | 95.83 | 71.88 | 69.79 | 71.28 | 71.70 | 58.94 | 57.87 | 75.42 | 75.78 |
|  | VvCYP716A17 | 80.83 | 75.26 | 95.83 | 100.00 | 71.67 | 70.00 | 71.49 | 71.91 | 58.51 | 57.02 | 75.21 | 75.78 |
|  | PgCYP716A52v2 | 45.42 | 73.17 | 71.83 | 71.67 | 100.00 | 71.52 | 72.59 | 73.01 | 57.54 | 57.11 | 73.33 | 80.79 |
|  | MlCYP716A75 | 72.08 | 67.51 | 69.79 | 70.00 | 71.52 | 100.00 | 68.20 | 68.20 | 56.05 | 54.99 | 68.96 | 73.90 |
|  | CqCYP716A78 | 73.58 | 68.70 | 71.28 | 71.49 | 72.59 | 68.20 | 100.00 | 97.10 | 55.96 | 55.11 | 68.61 | 72.12 |
|  | CqCYP716A79 | 73.38 | 69.33 | 71.70 | 71.91 | 73.01 | 68.20 | 97.10 | 100.00 | 55.96 | 55.11 | 68.81 | 72.75 |
|  | BvCYP716A80 | 62.34 | 60.90 | 58.94 | 58.51 | 57.54 | 56.05 | 55.96 | 55.96 | 100.00 | 95.37 | 57.87 | 58.64 |
|  | BvCYP716A81 | 61.28 | 60.04 | 57.87 | 57.02 | 57.11 | 54.99 | 55.11 | 55.11 | 95.37 | 100.00 | 56.81 | 57.57 |
|  | MdCYP716A175 | 77.08 | 73.38 | 75.42 | 75.21 | 73.33 | 68.96 | 68.61 | 68.81 | 57.87 | 56.81 | 100.00 | 74.17 |
|  | CrCYP716AL1 | 76.62 | 73.11 | 75.78 | 75.78 | 80.79 | 73.90 | 72.12 | 72.75 | 58.64 | 57.57 | 74.17 | 100.00 |

SEQ ID NO: 1 - Q. saponaria β-amyrin synthase, QsbAS (OQHZ-2074321) coding sequence (2277bp):
ATGTGGAGGCTGAAGATAGCAGAAGGTGGTTCCGATCCATATCTGTTCAGCACAAACAACTTCGTGGG

TCGCCAGACATGGGAGTTCGAACCGGAGGCCGGCACACCTGAGGAGCGAGCAGAGGTCGAAGCTGCCC

GCCAAAACTTTTACAACAACCGTTACCAGGTCAAGCCCTGTGACGACCTCCTTTGGAGATATCAGTTC

CTGAGAGAGAAGAATTTCAAACAAACAATACCGCCTGTCAAGGTTGAAGATGGCCAAGAAATTACTTA

TGAGATGGCCACAACCTCAATGCAGAGGGCGGCCCGTCACCTATCAGCCTTGCAGGCCAGCGATGGCC

ATTGGCCAGCTCAAATTGCTGGCCCCTTGTTCTTCATGCCACCCTTGGTCTTTTGTGTGTACATTACT

GGGCATCTTAATACAGTATTCCCATCTGAACATCGCAAAGAAATCCTTCGTTACATGTACTATCACCA

-continued

```
GAACGAAGATGGTGGGTGGGGACTGCACATAGAGGGTCACAGCACCATGTTTTGCACAGCACTCAACT
ACATTTGTATGCGTATCCTTGGGGAAGGACCAGAGGGGGGTCAAGACAATGCTTGTGCCAGAGCACGA
ATGTGGATTCTTGATCATGGTGGTGTAACACATATTCCATCTTGGGGAAAGACCTGGCTTTCGATACT
TGGTCTATTTGAGTGGTCTGGAAGCAATCCAATGCCTCCAGAGTTTTGGATCCTTCCTTCATTTCTTC
CTATGCATCCAGCAAAAATGTGGTGCTATTGCCGGATGGTTTACATGCCCATGTCTTATTTATATGGG
AAAAGGTTTGTTGGCCCAATCACGCCTCTCATTGTTCAGTTAAGAGAGGAAATACACACTCAAAATTA
CCATGAAATCAACTGGAAGTCAGTCCGCCATCTATGTGCAAAGGAGGATATCTACTATCCCCATCCAC
TCATCCAAGATTTGATTTGGGACAGTTTGTACATACTAACGGAGCCTCTTCTCACTCGCTGGCCCTTG
AACAAGTTGGTGCGGGAGAGGGCTCTCCAAGTAACAATGAAGCATATCCACTATGAAGATGAAAATAG
TCGATACATAACCATTGGATGTGTGGAAAAGGTGTTATGTATGCTTGCTTGTTGGGTTGATGATCCAA
ATGGAGATGCTTTCAAGAAGCACCTTGCTCGAGTCCCAGATTACGTATGGGTCTCTGAAGATGGAATT
ACTATGCAGAGTTTTGGTAGTCAAGAATGGGATGCTGGCTTTGCCGTCCAGGCTCTGCTTGCTTCTAA
TCTTACCGAGGAACTTGGCCCTGCTCTTGCCAAAGGACATGACTTCATAAAGCAATCTCAGGTTAAGG
ACAATCCTTCAGGTGACTTCAAAAGCATGTATCGTCACATTTCTAGAGGATCATGGACCTTCTCTGAC
CAAGATCATGGATGGCAAGTTTCTGATTGCACTGCAGAAGGTCTGAAGTGTTGCCTGCTTTTGTCGAT
GTTGCCACCAGAAATTGTTGGTGAAAAAATGGAACCACAAAGGCTATTTGATTCTGTCAATGTGCTGC
TCTCTCTACAGAGCAAAAAGGTGGTTTAGCTGCCTGGGAGCCAGCAGGGGCGCAAGATTGGTTGGAA
TTACTCAATCCCACAGAATTTTTTGCGGACATTGTCGTTGAGCATGAATATGTTGAATGTACTGGATC
AGCAATTCAGGCATTAGTTTTGTTCAAGAAGCTGTATCCGGGGCACAGGAAAAAAGAGATTGACAGTT
TCATTACAAATGCTGTCCGGTTCCTTGAGAATACACAAACGGCAGATGGCTCTTGGTATGGAAACTGG
GGAGTTTGCTTCACCTATGGTTGTTGGTTCGCACTGGGAGGGCTAGCAGCAGCTGGCAAGACTTACAA
CAACTGTCCTGCAATACGCAAAGCTGTTAATTTCCTACTTACAACACAAAGAGAAGACGGTGGTTGGG
GAGAAAGCTATCTTTCAAGCCCAAAAAAGATATATGTACCCCTGGAAGGAAGCCGATCAAATGTGGTA
CATACTGCATGGGCTATGATGGGTCTAATTCATGCTGGGCAGGCTGAAAGAGACTCAACTCCTCTTCA
TCGTGCAGCAAAGTTGATCATCAATTATCAACTAGAAAATGGCGATTGGCCGCAACAGGAAATCACTG
GAGTATTCATGAAAAACTGCATGTTACATTACCCTATGTACAGAAACATCTACCCAATGTGGGCTCTT
GCAGAATACCGGAGGCGGGTTCCATTGCCTTAA
```

SEQ ID NO: 2 - QsbAS (OQHZ-2074321) translated nucleotide sequence (758aa):

```
MWRLKIAEGGSDPYLFSTNNFVGRQTWEFEPEAGTPEERAEVEAARQNFYNNRYQVKPCDDLLWRYQF
LREKNFKQTIPPVKVEDGQEITYEMATTSMQRAARHLSALQASDGHWPAQIAGPLFFMPPLVFCVYIT
GHLNTVFPSEHRKEILRYMYYHQNEDGGWGLHIEGHSTMFCTALNYICMRILGEGPEGGQDNACARAR
MWILDHGGVTHIPSWGKTWLSILGLFEWSGSNPMPPEFWILPSFLPMHPAKMWCYCRMVYMPMSYLYG
KRFVGPITPLIVQLREEIHTQNYHEINWKSVRHLCAKEDIYYPHPLIQDLIWDSLYILTEPLLTRWPL
NKLVRERALQVTMKHIHYEDENSRYITIGCVEKVLCMLACWVDDPNGDAFKKHLARVPDYVWVSEDGI
QDHGWQVSDCTAEGLKCCLLLSMLPPEIVGEKMEPQRLEDSVNVLLSLQSKKGGLAAWEPAGAQDWLE
TMQSFGSQEWDAGFAVQALLASNLTEELGPALAKGHDFIKQSQVKDNPSGDFKSMYRHISRGSWTFSD
LLNPTEFFADIVVEHEYVECTGSAIQALVLFKKLYPGHRKKEIDSFITNAVRFLENTQTADGSWYGNW
GVCFTYGCWFALGGLAAAGKTYNNCPAIRKAVNFLLTTQREDGGWGESYLSSPKKIYVPLEGSRSNVV
HTAWAMMGLIHAGQAERDSTPLHRAAKLIINYQLENGDWPQQEITGVEMKNCMLHYPMYRNIYPMWAL
AEYRRRVPLP*
```

SEQ ID NO: 3 - QsCYP716_2073932 (OQHZ-2073932) (C-28 oxidase, named
previously as CYP716A224 [3]) coding sequence (1443bp):
ATGGAGCACTTGTATCTCTCCCTTGTGCTCCTGTTTGTTTCCTCAATCTCCCTCTCCCTCTTCTTCCT

GTTCTACAAACACAAATCTATGTTCACCGGGGCCAACCTACCACCTGGTAAAATCGGTTACCCATTGA

TCGGAGAGAGCTTGGAGTTCTTGTCCACGGGATGGAAGGGCCACCCGGAGAAATTCATCTTCGATCGC

ATGAGCAAGTACTCATCCCAAATCTTCAAGACCTCGATTTTAGGGGAACCAACGGCGGTGTTCCCGGG

AGCCGTATGCAACAAGTTCCTCTTCTCCAACGAGAACAAGCTGGTGAATGCATGGTGGCCTGCCTCCG

TGGACAAGATCTTTCCTTCCTCACTCCAGACATCCTCCAAAGAAGAGGCCAAGAAGATGAGGAAGTTG

CTTCCTCAGTTTCTCAAGCCCGAAGCTCTGCACCGCTACATTGGTATTATGGATTCTATTGCCCAGAG

ACACTTTGCCGATAGCTGGGAAAACAAAAACCAAGTCATTGTCTTTCCTCTAGCAAAGAGGTATACTT

TCTGGCTGGCTTGCCGTTTGTTCATTAGCGTCGAGGATCCGACCCACGTATCCAGATTTGCTGACCCG

TTCCAACTTTTGGCCGCCGGAATCATATCAATCCCAATCGACTTGCCAGGGACACCGTTCCGCAAGGC

AATCAATGCGTCCCAGTTCATCAGGAAGGAATTGTTGGCCATCATCAGGCAGAGAAAGATCGATTTGG

GTGAAGGGAAGGCATCTCCGACGCAGGACATACTGTCTCACATGTTGCTCACATGCGACGAGAACGGA

CAATACATGAATGAATTGGACATTGCCGACAAGATTCTTGGCTTGTTGGTCGGCGGACATGACACTGC

CAGTGCCGCTTGCACTTTCATTGTCAAGTTCCTCGCTGAGCTTCCCCACATTTATGAACAAGTCTACA

AGGAGCAAATGGAGATTGCAAAATCAAAAGTGCCAGGAGAGTTGTTGAATTGGGAGGACATCCAAAAG

ATGAAATATTCGTGGAACGTAGCTTGTGAAGTGATGAGACTTGCCCCTCCACTCCAAGGAGCTTTCAG

GGAAGCCATTACTGACTTCGTCTTCAACGGTTTCTCCATTCCAAAAGGCTGGAAGTTGTACTGGAGCG

CAAATTCCACCCACAAAAGTCCGGATTATTTCCCTGAGCCCGACAAGTTCGACCCAACTAGATTCGAA

GGAAATGGACCTGCGCCTTACACCTTTGTTCCATTTGGGGGAGGACCCAGGATGTGCCCGGGCAAAGA

GTATGCCCGATTGGAAATACTTGTGTTCATGCATAACTTGGTGAAGAGGTTCAAGTGGGAGAAATTGG

TTCCTGATGAAAAGATTGTGGTTGATCCAATGCCCATTCCAGCAAAGGGTCTTCCTGTTCGCCTTTAT

CCTCACAAAGCTTGA

SEQ ID NO: 4 - QsCYP716_2073932 (OQHZ-2073932) translated nucleotide
sequence (480aa):
MEHLYLSLVLLFVSSISLSLFFLFYKHKSMFTGANLPPGKIGYPLIGESLEFLSTGWKGHPEKFIFDR

MSKYSSQIFKTSILGEPTAVFPGAVCNKFLFSNENKLVNAWWPASVDKIFPSSLQTSSKEEAKKMRKL

LPQFLKPEALHRYIGIMDSIAQRHFADSWENKNQVIVFPLAKRYTFWLACRLFISVEDPTHVSRFADP

FQLLAAGIISIPIDLPGTPFRKAINASQFIRKELLAIIRQRKIDLGEGKASPTQDILSHMLLTCDENG

QYMNELDIADKILGLLVGGHDTASAACTFIVKFLAELPHIYEQVYKEQMEIAKSKVPGELLNWEDIQK

MKYSWNVACEVMRLAPPLQGAFREAITDFVENGFSIPKGWKLYWSANSTHKSPDYFPEPDKFDPTRFE

GNGPAPYTFVPFGGGPRMCPGKEYARLEILVFMHNLVKRFKWEKLVPDEKIVVDPMPIPAKGLPVRLY

PHKA*

SEQ ID NO: 5 - QsCYP716_2012090 (OQHZ-2012090) (C-16a oxidase) coding
sequence (1506bp/1443bp):
NB Long and short isoforms as described herein are distinguished by
the presence of the first 63 nucleotides, underlined in the sequences
below (21 amino acids).
<u>ATGATATATAATAATGATAGTAATGATAATGAATTAGTAATCAGCTCAGTTCAGCAACCATCCATGGA</u>

TCCTTTCTTCATTTTTGGCTTACTTCTCTTGGCTCTCTTTCTCTCTGTTTCTTTTCTTCTCTACCTTT

CCCGTAGAGCCTATGCTTCTCTCCCCAACCCTCCGCCGGGGAAGCTCGGCTTCCCCGTCGTCGGCGAG

AGTCTCGAATTTCTCTCCACCCGACGCAAAGGTGTTCCTGAGAAATTCGTCTTCGACAGAATGGCCAA

ATACTGTCGGGATGTCTTTAAGACATCAATATTGGGAGCAACCACCGCCGTCATGTGCGGCACCGCCG

GTAACAAATTCTTGTTCTCCAACGAGAAAAAACACGTCACTGGTTGGTGGCCGAAATCTGTAGAGCTG

ATTTTCCCAACCTCACTTGAGAAATCATCCAACGAAGAATCCATCATGATGAAACAATTCCTTCCCAA

CTTCTTGAAACCAGAACCTTTGCAGAAGTACATACCCGTTATGGACATAATTACCCAAAGACACTTCA

ATACAAGCTGGGAAGGACGCAACGTGGTCAAAGTGTTTCCTACGGCTGCCGAATTCACCACGTTGCTG

GCTTGTCGGGTATTCCTCAGTGTTGAGGATCCCATTGAAGTAGCCAAGATTTCAGAGCCATTTGAAAT

CTTAGCTGCTGGGTTTCTTTCAATACCCATAAATCTTCCGGGTACCAAATTAAATAAAGCGGTTAAGG

CAGCGGATCAGATTAGAGACGCAATTGTACAGATTTTGAAACGGAGAAGGGTTGAAATTGCGGAGAAT

AAAGCAAATGGAATGCAAGATATAGCGTCCATGTTGTTGACGACACCAACTAATGCTGGGTTTTATAT

GACCGAGGCTCACATTTCTGAGAAATTTTGGGTATGATTGTTGGTGGCCGTGATACTGCTAGTACTG

TTATCACCTTCATCATCAAGTATTTGGCAGAGAATCCTGAAATTTATAATAAGGTCTATGAGGAGCAA

ATGGAAGTGGTAAAGTCAAAGAAACCAGGTGAGTTGCTGAACTGGGAAGATGTGCAGAAAATGAAGTA

CTCTTGGTGCGTAGCATGTGAAGCTATGCGACTTGCTCCTCCTGTTCAAGGTGGTTTCAAGGTGGCCA

TTAATGACTTTGTGTATTCTGGGTTCAACATTCGCAAGGGTTGGAAGTTATATTGGAGTGCCATTGCA

ACACACATGAATCCAGAATATTTCCCAGAACCTGAGAAATTCAACCCCTCAAGGTTTGAAGGGAAGGG

ACCAGTACCTTACAGCTTCGTACCCTTCGGAGGCGGACCTCGGATGTGTCCCGGGAAAGAGTATTCCC

GGCTGGAAACACTTGTTTTCATGCATCATTTGGTGACGAGGTACAATTGGGAGAAAGTGTATCCCACA

GAGAAGATAACAGTGGATCCAATGCCATTCCCTGTCAACGGCCTCCCCATTCGCCTTATTCCTCACAA

GCACCAATGA

SEQ ID NO: 6 - QsCYP716_2073932 translated nucleotide sequence
(501aa/480aa):
MIYNNDSNDNELVISSVQQPSMDPFFIFGLLLLALFLSVSFLLYLSRRAYASLPNPPPGKLGFPVVGE

SLEFLSTRRKGVPEKFVFDRMAKYCRDVFKTSILGATTAVMCGTAGNKFLFSNEKKHVTGWWPKSVEL

IFPTSLEKSSNEESIMMKQFLPNFLKPEPLQKYIPVMDIITQRHENTSWEGRNVVKVFPTAAEFTTLL

ACRVFLSVEDPIEVAKISEPFEILAAGFLSIPINLPGTKLNKAVKAADQIRDAIVQILKRRRVEIAEN

KANGMQDIASMLLTTPTNAGFYMTEAHISEKILGMIVGGRDTASTVITFIIKYLAENPEIYNKVYEEQ

MEVVKSKKPGELLNWEDVQKMKYSWCVACEAMRLAPPVQGGFKVAINDFVYSGFNIRKGWKLYWSAIA

THMNPEYFPEPEKFNPSRFEGKGPVPYSFVPFGGGPRMCPGKEYSRLETLVFMHHLVTRYNWEKVYPT

EKITVDPMPFPVNGLPIRLIPHKHQ*

SEQ ID NO: 7 - QsCYP714_c36368 (C-23 candidate #7) coding sequence
(1524bp):
ATGTGGTTCACAGTAGGATTGGTCTTGGTTTTCGCCCTATTCATACGTCTCTACAGCAGTCTGTGGTT

GAAGCCTCGTGCAACTCGGATTAAGCTTAGCAATCAAGGAATTAAAGGTCCAAAACCAGCATTTCTTC

TGGGTAATGTTGCAGAGATGAGAAGATTTCAATCTAAGCTTCCAAAATCTGAACTCAAACAAGGCCAA

GTTTCTCATGATTGGGCTTCTAAATCTCTGTTTCCATTTTTCAGTCTTTGGTCCCAGAAATACGGAAA

TACGTTCGTGTTCTCATTGGGGAACATACAGGTGCTCTATGTTTCTGATCATGAGTTGGTGAAAGAAA

TTAATCAGAATACCTCTTTAGATTTGGGCAAACCCAAGTACCTGCAGAAGGAGCGTGGCCCTTTGCTG

GGACAAGGTATTTTGACCTCCAATGGACAGCTTTGGGCGTACCAGAGAAAAATCATGACTCCTGAACT

CTACAAGGAGAAAATCAAGGGCATGTGCGAGTTGATGGTGGAATCTGTAGCTTGGTTGGTTGAGGAAT

GGGGAACGAAGATCCAAGCTGAGGGTGGGCAGCAGACATTAGAATAGACGAGGATCTTAGAAGCTTC

TCTGGTGATGTAATTTCAAAAGCTTGTTTTGGGAGCTGCTATGCCGGAGGGAGGGAAATCTTTCTTAG

GCTCAGAGCTCTTCAACACCAAATTGCTTCCAAAGCCTTACTCATGGGCTTCCCTGGATTAAAGTACC

TGCCCATTAAGAGCAACAGAGAGATATGGAGATTGGAGAAGGAGATCTTCCAGCTGATTATGAAGCTG

GCTGAAGATAGAAAAAAAGAACAACATGAGAGAGACCTATTACAGATTATAATTGAGGGAGCTAAAAG

-continued

```
TAGTGATCTGAGTTCGGAAGCAATGGCAAAATTCATTGTGGACAACTGCAAGAATGTCTACTTGGCTG

GCCATGAAACTACTGCAATGTCTGCTGGTTGGACTTTGCTTCTCTTGGCTAATCATCCTGAGTGGCAA

GCCCGTGTCCGTGATGAGATTTTACAAGTCACCGAGGGCCGCAATCCTGATTTTGACATGCTGCACAA

GATGAAACTGTTAACAATGGTAATTCAGGAGGCACTGCGACTCTACCCAACAGTCATATTCATGTCAA

GAGAAGCATTGGAAGATATTAATGTTGGAAACATCCAAGTTCCAAAAGGTGTTAACATATGGATACCT

GTGGTAAATCTTCAAAGGGACACAACGGTATGGGGTGCAGACGCAAACGAGTTTAATCCTGAAAGGTT

TGCCAATGGAGTTAACAATTCATGCAAGGTTCCACAACTTTACCTACCATTTGGAGCTGGACCTCGCA

TTTGTCCTGGAATTAATCTGGCCATGACTGAGATCAAGATACTTCTGTGTATCCTGCTCACCAAGTTT

TCGTTTTCAGTTTCACCCAACTATCGCCACTCACCGGTGTTTAAATTGGTGCTTGAGCCTGAAAATGG

AATCAATGTCATCATGAAGAAGCTCTAA
```

SEQ ID NO: 8 - QsCYP714_c36368 (C-23 candidate #7) translated nucleotide sequence (507aa):
```
MWFTVGLVLVFALFIRLYSSLWLKPRATRIKLSNQGIKGPKPAFLLGNVAEMRRFQSKLPKSELKQGQ

VSHDWASKSLFPFFSLWSQKYGNTFVFSLGNIQVLYVSDHELVKEINQNTSLDLGKPKYLQKERGPLL

GQGILTSNGQLWAYQRKIMTPELYKEKIKGMCELMVESVAWLVEEWGTKIQAEGGAADIRIDEDLRSF

SGDVISKACFGSCYAGGREIFLRLRALQHQIASKALLMGFPGLKYLPIKSNREIWRLEKEIFQLIMKL

AEDRKKEQHERDLLQIIIEGAKSSDLSSEAMAKFIVDNCKNVYLAGHETTAMSAGWTLLLLANHPEWQ

ARVRDEILQVTEGRNPDFDMLHKMKLLTMVIQEALRLYPTVIFMSREALEDINVGNIQVPKGVNIWIP

VVNLQRDTTVWGADANEFNPERFANGVNNSCKVPQLYLPFGAGPRICPGINLAMTEIKILLCILLTKF

SFSVSPNYRHSPVFKLVLEPENGINVIMKKL****
```

SEQ ID NO: 9; BfCYP716Y1 (*Bupleurum falcatum* C-16α oxidase) coding sequence 1437bp):
```
ATGGAACTTTCTATCACTCTGATGCTTATTTTCTCAACAACCATCTTCTTTATATTCGTAATGTGTA

CAACCATCTCATCTCTAAACACAAAAACTATCCCCCTGGAAGTATGGGCTTGCCTTACATTGGCGAAA

CACTTAGTTTCGCGAGATACATCACCAAAGGAGTCCCTGAAAAATTCGTAATAGAAAGACAAAAGAAA

TATTCAACAACAATATTTAAGACCTCCTTGTTCGGAGAAAACATGGTGGTGTTGGGCAGTGCAGAGGG

CAACAAATTTATTTTTGGAAGCGAGGAGAAGTATTTACGAGTGTGGTTTCCAAGTTCTGTGGACAAAG

TGTTCAAAAAATCTCATAAGAGAACGTCGCAGGAAGAAGCTATTAGGTTGCGCAAAAACATGGTGCCA

TTTCTCAAAGCAGATTTGTTGAGAAGTTATGTACCAATAATGGACACATTTATGAAACAACATGTGAA

CTCGCATTGGAATTGCGAGACCTTGAAGGCTTGTCCTGTGATCAAGGATTTTACGTTTACTTTAGCTT

GTAAACTTTTTTTTAGTGTAGACAATCCTTTGGAGCTAGAGAAGTTAATCAAGCTATTTGTGAATATA

GTGAATGGCCTCCTTACGGTCCCTATTGATCTCCCGGGGACAAAATTTAGAGGAGTTATAAAGAGTGT

CAAGACTATTCGCCATGCGCTTAAAGTGTTGATCAGGCAACGAAAGGTGGATATTAGAGAGAAAAGAG

CCACACCTACGCAAGATATATTGTCGATAATGCTGGCACAGGCTGAGGACGAGAACTATGAAATGAAT

GATGAAGATGTGGCCAATGACTTTCTTGCAGTTTTGCTTGCTAGTTATGATTCTGCCAATACTACACT

CACCATGATTATGAAATATCTTGCTGAATATCCCGAAATGTATGATCGAGTTTTCAGAGAACAAATGG

AGGTGGCAAAGACGAAAGGAAAAGATGAATTACTCAACTTGGACGACTTGCAAAAGATGAATTATACT

TGGAATGTAGCTTGTGAAGTACTGAGAATTGCAACACCAACGTTCGGAGCATTCAGAGAGGTTATTGC

AGATTGTACATACGAAGGGTACACCATACCAAAAGGCTGGAAGCTATATTATGCCCCGCGTTTTACCC

ATGGAAGTGCAAAATACTTTCAAGATCCAGAGAAATTTGATCCATCGCGATTTGAAGGTGATGGTGCG

CCTCCTTATACATTCGTTCCATTCGGAGGAGGGCTCCGGATGTGCCCTGGATACAAGTATGCAAAGAT

TATAGTACTAGTGTTCATGCACAATATAGTTACAAAGTTCAAATGGGAGAAAGTTAACCCTAATGAGA

AAATGACAGTAGGAATCGTATCAGCGCCAAGTCAAGGACTTCCACTGCGTCTCCATCCCCACAAATCT
```

CCATCTTAA

SEQ ID NO: 10; BfCYP716Y1 (*Bupleurum falcatum* C-16α oxidase) coding sequence (478aa):
MELSITLMLIFSTTIFFIFRNVYNHLISKHKNYPPGSMGLPYIGETLSFARYITKGVPEKFVIERQKK

YSTTIFKTSLFGENMVVLGSAEGNKFIFGSEEKYLRVWFPSSVDKVFKKSHKRTSQEEAIRLRKNMVP

FLKADLLRSYVPIMDTFMKQHVNSHWNCETLKACPVIKDFTFTLACKLFFSVDNPLELEKLIKLFVNI

VNGLLTVPIDLPGTKFRGVIKSVKTIRHALKVLIRQRKVDIREKRATPTQDILSIMLAQAEDENYEMN

DEDVANDFLAVLLASYDSANTTLTMIMKYLAEYPEMYDRVFREQMEVAKTKGKDELLNLDDLQKMNYT

WNVACEVLRIATPTFGAFREVIADCTYEGYTIPKGWKLYYAPRFTHGSAKYFQDPEKFDPSRFEGDGA

PPYTFVPFGGGLRMCPGYKYAKIIVLVFMHNIVTKFKWEKVNPNEKMTVGIVSAPSQGLPLRLHPHKS

PS*

SEQ ID NO: 11; MlCYP87D16 (*Maesa lanceolata* C-16α oxidase) coding sequence 1428bp):
ATGTGGGTAGTGGGATTAATTGGTGTGGCTGTGGTAACAATATTGATAACTCAGTATGTATACAAATG

GAGAAATCCAAAGACTGTGGGTGTTCTGCCACCTGGTTCAATGGGTCTGCCTTTGATCGGGGAGACTC

TTCAACTTCTCAGCCGTAATCCATCCTTGGATCTTCATCCTTTCATCAAGAGCAGAATCCAAAGATAT

GGGCAGATATTCGCGACCAATATCGTAGGTCGACCCATAATAGTAACCGCTGATCCGCAGCTCAATAA

TTACCTTTTCCAACAAGAAGGAAGAGCAGTAGAACTGTGGTACTTGGACAGCTTTCAAAAGCTATTTA

ACTTAGAAGGTGCAAACAGGCCGAACGCAGTTGGTCACATTCACAAGTACGTTAGAAGTGTATACTTG

AGTCTCTTTGGCGTCGAGAGCCTTAAAACAAAGTTGCTTGCCGATATTGAGAAAACAGTCCGCAAAAA

TTGCTGCAAAATACTTGTTCGGACATGATTACGAGAAATCGAAAGAAGATGTAGGCAGCATAATCGAC

TCTTATTGGTGGGACAACCAAAGGCACCTTTGATGCAAAACATGCTTCTGCCAATATGGTTGCTGTTT

AACTTCGTACAAGGACTTCTCGCATTCCCATTGAATGTTCCCGGTACAAAGTTCCACAAATGTATGAA

GGACAAGAAAAGGCTGGAATCAATGATCACTAACAAGCTAAAGGAGAGAATAGCTGATCCGAACAGCG

GACAAGGGGATTTCCTTGATCAAGCAGTGAAAGACTTGAATAGCGAATTCTTCATAACAGAGACTTTT

ATCGTTTCGGTGACGATGGGAGCTTTATTTGCGACGGTTGAATCGGTTTCGACAGCAATTGGACTAGC

TTTCAAGTTTTTTGCAGAGCACCCCIGGGTTTTGGATGACCTCAAGGCTGAGCATGAGGCTGTCCTTA

GCAAAAGAGAGGATAGAAATTCACCTCTCACGTGGGACGAATATAGATCGATGACACACACGATGCAC

TTTATCAATGAAGTCGTCCGTTTGGGAAATGTTTTTCCTGGAATTTTGAGGAAAGCACTGAAAGATAT

TCCATATAATGGTTATACAATTCCGTCCGGTTGGACCATTATGATTGTGACCTCTACCCTTGCGATGA

ACCCTGAGATATTCAAGGATCCTCTTGCATTCAATCCGAAACGTTGGCGGGATATTGATCCCGAAACT

CAAACTAAAAACTTTATGCCTTTCGGTGGTGGGACGAGACAATGCGCAGGTGCAGAGCTAGCCAAGGC

ATTCTTTGCTACCTTCCTCCATGTTTTAATCAGCGAATATAGCTGGAAGAAAGTGAAGGGAGGAAGCG

TTGCTCGGACACCTATGTTAAGTTTTGAAGATGGCATATTTATTGAGGTCACCAAGAAAAACAAGTGA

SEQ ID NO: 12; MlCYP87D16 (*Maesa lanceolata* C-16α oxidase) coding sequence (475aa):
MWVVGLIGVAVVTILITQYVYKWRNPKTVGVLPPGSMGLPLIGETLQLLSRNPSLDLHPFIKSRIQRY

GQIFATNIVGRPIIVTADPQLNNYLFQQEGRAVELWYLDSFQKLENLEGANRPNAVGHIHKYVRSVYL

SLFGVESLKTKLLADIEKTVRKNLIGGTTKGTFDAKHASANMVAVFAAKYLFGHDYEKSKEDVGSIID

NFVQGLLAFPLNVPGTKFHKCMKDKKRLESMIINKLKERIADPNSGQGDFLDQAVKDLNSEFFITETF

IVSVTMGALFATVESVSTAIGLAFKFFAEHPWVLDDLKAEHEAVLSKREDRNSPLTWDEYRSMTHTMH

FINEVVRLGNVFPGILRKALKDIPYNGYTIPSGWTIMIVTSTLAMNPEIFKDPLAFNPKRWRDIDPET

QTKNFMPFGGGTRQCAGAELAKAFFATFLHVLISEYSWKKVKGGSVARTPMLSFEDGIFIEVTKKNK*

SEQ ID NO: 13; MtCYP72A68v2 (*Medicago truncatula* C-23 oxidase) coding
sequence 1563bp):
ATGGAATTATCTTGGGAAACAAAATCAGCCATAATTCTCATCACTGTGACATTTGGTTTGGTATACGC

ATGGAGGGTATTGAATTGGATGTGGCTGAAGCCAAAGAAGATAGAGAAGCTTTTAAGAGAACAAGGCC

TTCAAGGGAACCCTTATAGACTTTTGCTTGGAGATGCAAAGGATTATTTTGTGATGCAAAAGAAAGTT

CAATCCAAACCCATGAATCTATCTGATGATATTGCGCCACGTGTCGCTCCTTACATTCATCATGCTGT

TCAAACTCATGGGAAAAAGTCTTTTATTTGGTTTGGAATGAAACCATGGGTGATTCTCAATGAACCTG

AACAAATAAGAGAAGTATTCAACAAGATGTCTGAGTTCCCAAAGGTTCAATATAAGTTTATGAAGTTA

ATAACTCGCGGTCTTGTTAAACTAGAAGGAGAAAAGTGGAGCAAGCATAGAAGAATAATCAACCCTGC

GTTTCACATGGAAAAATTGAAGATTATGACACCAACATTCTTGAAAAGCTGCAATGATTTGATTAGCA

ATTGGGAAAAAATGTTGTCTTCAAATGGATCATGTGAAATGGACGTATGGCCTTCCCTTCAGAGCTTG

ACAAGTGATGTTATCGCTCGTTCGTCATTTGGAAGTAGTTATGAAGAAGGAAGAAAAGTATTTCAACT

TCAAATAGAGCAAGGTGAACTTATAATGAAAAATCTAATGAAATCTTTAATCCCTTTATGGAGGTTTT

TACCTACCGCTGATCATAGAAAGATAAATGAAAATGAAAAACAAATAGAAACTACTCTTAAGAATATA

ATTAACAAGAGGGAAAAAGCAATTAAGGCAGGTGAAGCCACTGAGAATGACTTATTAGGTCTCCTCCT

AGAGTCGAACCACAGAGAAATTAAAGAACATGGAAACGTCAAGAATATGGGATTGAGTCTTGAAGAAG

TAGTCGGGGAATGCAGGTTATTCCATGTTGCAGGGCAAGAGACTACTTCAGATTTGCTTGTTTGGACG

ATGGTGTTGTTGAGTAGGTACCCTGATTGGCAAGAACGTGCAAGGAAGGAAGTATTAGAGATATTTGG

CAATGAAAAACCCGACTTTGATGGACTAAATAAACTTAAGATTATGGCCATGATTTTGTATGAGGTTT

TGAGGTTGTACCCTCCTGTAACCGGCGTTGCTCGAAAAGTTGAGAATGATATAAAACTTGGAGACTTG

ACATTATATGCTGGAATGGAGGTTTACATGCCAATTGTTTTGATTCACCATGATTGTGAACTATGGGG

TGATGATGCTAAGATTTTCAATCCTGAGAGATTTTCTGGTGGAATTTCCAAAGCAACAAACGGTAGAT

TTTCATATTTTCCGTTTGGAGCGGGTCCTAGAATCTGCATTGGACAAAACTTTTCCCTGTTGGAAGCA

AAGATGGCAATGGCATTGATTTTAAAGAATTTTTCATTTGAACTTTCTCAAACATATGCTCATGCTCC

ATCTGTGGTGCTTTCTGTTCAGCCACAACATGGTGCTCATGTTATTCTACGCAAAATCAAAACATAA

SEQ ID NO: 14; MtCYP72A68v2 (*Medicago truncatula* C-23 oxidase)
translated nucleotide sequence 520aa):
MELSWETKSAIILITVTFGLVYAWRVLNWMWLKPKKIEKLLREQGLQGNPYRLLLGDAKDYFVMQKKV

QSKPMNLSDDIAPRVAPYIHHAVQTHGKKSFIWFGMKPWVILNEPEQIREVENKMSEFPKVQYKFMKL

ITRGLVKLEGEKWSKHRRIINPAFHMEKLKIMTPTFLKSCNDLISNWEKMLSSNGSCEMDVWPSLQSL

TSDVIARSSFGSSYEEGRKVFQLQIEQGELIMKNLMKSLIPLWRFLPTADHRKINENEKQIETTLKNI

INKREKAIKAGEATENDLLGLLLESNHREIKEHGNVKNMGLSLEEVVGECRLFHVAGQETTSDLLVWT

MVLLSRYPDWQERARKEVLEIFGNEKPDFDGLNKLKIMAMILYEVLRLYPPVTGVARKVENDIKLGDL

TLYAGMEVYMPIVLIHHDCELWGDDAKIFNPERFSGGISKAINGRESYFPFGAGPRICIGQNFSLLEA

KMAMALILKNFSFELSQTYAHAPSVVLSVQPQHGAHVILRKIKT*

SEQ ID NO: 15; AsCYP94D65 (*Avena strigosa* C-23 oxidase) coding
sequence 1551bp):
ATGGAGCCGGCGCCCTTGAGCTCATCGCCGGTGCTTATCTGCCTCCTACTCCTACTCCTACCCATCGT

CCTCTATTTTGTGTACCGGAAAAATAATCTGAAGAGGAAGCAGCAGCAGCAGCAGCAGAATGGGCCGC

GGGAGCTGCGGGCGTACCCGATCGTGGGCACGCTTCCACACTTCATCAAGAACGGGCGGCGCTTCCTG

GAGTGGTCGTCGGCCGTCATGCAGCGCAGCCCGACGCACACCATGATCCTCAAGGTGCTGGGCCTGTC

GGGCACCGTGTTCACGGCGAGCCCGGCCAGCGTGGAACACGTGCTGAAGACGCGCTTCGCGAACTACC

CGAAAGGCGGTCTGGTCGATATCCAGACCGACTTCCTTGGGCACGGCATCTTCAACTCGGACGGCGAG

GAGTGGCAGCAGCAGCGCAAGATGGCCAGCTACGAGTTCAACCAGCGGTCGCTCAGGAGCTTCGTGGT

```
GCACGCCGTCCGTTTCGAGGTGGTGGAGCGCCTGCTGCCGCTGCTGGAGCGGGCCGCCGGGGCTGGAG

CGGCCGTCGACCTGCAGGACGTGCTGGAGCGCTTCGCCTTCGACAACATCTGCCGCGTGGCTTTCGGC

CAGGACCCGGCATGCCTCACGGAGGAGAGCATGGGCGCGAGGCAGAGCGTGGAGTTGATGCACGCCTT

CGATGTGGCAAGCACCATCGTCATTACCAGGTTCGTGTCTCCACGTGGTTGTGGCGCCTGATGAAGC

TGCTCAACGTGGGGCCGGAGCGGCGGATGCGGAAGGCACTGGCATCCATCCACGGCTACGCCGACAAC

ATCATCCGGGAGAGGAAGAAGAAGAAGAAGACATCAGGGAAGGACGACGACCTCCTGTCGCGCTTCGC

CGATTCCGGCGAGCACAGCGACGAGAGCCTCCGCTACGTGATCACCAACTTCATACTCGCCGGCCGCG

ACTCCAGCTCCGCCGCGCTCACATGGTTTTTCTGGCTCGTCTCCACCAGGCCCGAGGTACAGGACAGG

ATCTCCAAGGAGATCCGAGCGGCGCGCCAGGCAAGCGCAACGACGACGGGGCCCTTCGGCCTGGAGGA

GCTGCGCGAGATGCACTACATCCACGCCGCCATCACGGAGTCCATGCGGCTCTACCCGCCGGTGCCCA

TCAACGCGCGCACCTCCACCGAGGACGATGTCCTTCCAGACGGCACCGTGGTCGGGAAAGGCTGGCGG

GTGATCTACTCCGCCTACGCCATGGGGCGGATGGAGGACGCCTGGGGAAAGGACGGGGACGAGTTCCG

GCCGGAGAGGTGGCTGGACGCGGAGACAGGGGTGTTCAGGCCGGAGGCACCCTGCAAGTACCCGGTGT

TCCACGTCGGCCCAAGAATGTGCCTCGGCAAAGAGATGGCCTACATACAGATGAAGTCCATCGTGGCG

TCCGTGTTTGAGAGGTTCAGCTTGCGCTACCTCGGCGGGGACGCCCATCCCGGCCTCCAGCTCGCTGG

AACTCTGCGCATGGAAGGCGGCTTGCCGATGCACCTAGAAATCAGTACTAACTAG
```

SEQ ID NO: 16; AsCYP94D65 (Avena strigosa C-23 oxidase) translated nucleotide sequence 516aa):
```
MEPAPLSSSPVLICLLLLLLPIVLYFVYRKNNLKRKQQQQQNGPRELRAYPIVGTLPHFIKNGRRFL

EWSSAVMQRSPTHTMILKVLGLSGTVFTASPASVEHVLKTRFANYPKGGLVDIQTDFLGHGIFNSDGE

EWQQQRKMASYEFNQRSLRSFVVHAVRFEVVERLLPLLERAAGAGAAVDLQDVLERFAFDNICRVAFG

QDPACLTEESMGARQSVELMHAFDVASTIVITRFVSPTWLWRLMKLLNVGPERRMRKALASIHGYADN

IIRERKKKKTSGKDDDLLSRFADSGEHSDESLRYVITNFILAGRDSSSAALTWFFWLVSTRPEVQDR

ISKEIRAARQASATTTGPFGLEELREMHYIHAAITESMRLYPPVPINARTSTEDDVLPDGTVVGKGWR

VIYSAYAMGRMEDAWGKDGDEFRPERWLDAETGVFRPEAPCKYPVFHVGPRMCLGKEMAYIQMKSIVA

SVFERFSLRYLGGDAHPGLQLAGTLRMEGGLPMHLEISTN*
```

SEQ ID NO: 17; MtCYP716A12 (Medicago truncatula C-28 oxidase) coding sequence 1440bp):
```
AAAGCCTTGAGTTCTTATCAACAGGATGGAAAGGACATCCTGAAAAATTCATTTTCGACCGTATGCGT

CATATTCTACAAACAGAAATCTCCATTAAATTTGCCACCTGGTAAAATGGGTTACCCAATCATAGGTG

ATGGAGCCTAATTTCTATCTCTCCCTTCTCCTTCTCTTTGTCACTTTCATATCTCTCTCTTTTTTT

AAATATTCCTCAGAACTCTTTAAAACATCAATCGTAGGAGAATCTACGGTGGTTTGTTGCGGAGCAGC

AAGTAACAAGTTTTTGTTTTCAAACGAGAATAAACTTGTGACTGCATGGTGGCCAGATAGTGTAAACA

AAATCTTCCCTACTACTTCTCTTGACTCTAACTTGAAGGAAGAATCCATCAAGATGAGAAAATTGCTT

CCACAATTCTTTAAACCCGAAGCTCTACAACGTTATGTTGGTGTCATGGATGTTATTGCTCAAAGACA

TTTTGTTACTCATTGGGATAATAAAAATGAAATCACCGTCTACCCCTTGGCCAAGAGGTACACCTTTT

TGTTAGCTTGTCGGTTGTTCATGAGCGTTGAAGACGAGAATCATGTAGCAAAATTTAGTGATCCATTT

CAGTTAATTGCGGCCGGAATCATATCTCTACCAATTGATTTGCCAGGAACACCATTCAACAAAGCTAT

AAAGGCCTCAAACTTTATAAGAAAGGAGTTGATTAAGATCATAAAGCAAAGGAGGGTAGATTTGGCAG

AAGGGACAGCATCACCAACACAAGATATATTGTCTCACATGTTGTTGACAAGTGATGAAAATGGAAAG

AGTATGAATGAACTTAATATTGCTGATAAGATTCTTGGCCTTTTGATCGGAGGACATGACACTGCTAG

CGTCGCATGCACTTTCCTTGTCAAATATCTCGGCGAGTTACCTCACATTTATGATAAAGTCTATCAAG
```

-continued

```
AGCAAATGGAAATTGCAAAATCGAAACCAGCAGGAGAATTGTTGAATTGGGATGACCTGAAGAAAATG

AAATACTCTTGGAACGTAGCTTGTGAAGTAATGAGACTTTCCCCTCCACTCCAAGGAGGTTTCAGGGA

AGCCATCACTGACTTTATGTTCAATGGATTCTCAATTCCTAAGGGATGGAAGCTTTATTGGAGTGCAA

ATTCAACACATAAGAACGCAGAATGTTTTCCCATGCCAGAGAAATTTGACCCAACAAGATTTGAAGGA

AATGGACCAGCTCCTTATACTTTTGTTCCCTTTGGTGGAGGACCAAGGATGTGTCCTGGAAAAGAGTA

TGCAAGATTAGAAATACTTGTTTTCATGCACAATTTGGTGAAAAGGTTTAAGTGGGAAAAGGTGATTC

CAGATGAGAAGATTATTGTTGATCCATTCCCCATCCCTGCAAAGGATCTTCCAATTCGCCTTTATCCA

CACAAAGCTTAA
```

SEQ ID NO: 18; MtCYP716A12 (*Medicago truncatula* C-28 oxidase) coding sequence (479aa):

```
MEPNFYLSLLLLFVTFISLSLFFIFYKQKSPLNLPPGKMGYPIIGESLEFLSTGWKGHPEKFIFDRMR

KYSSELFKTSIVGESTVVCCGAASNKFLFSNENKLVTAWWPDSVNKIFPTTSLDSNLKEESIKMRKLL

PQFFKPEALQRYVGVMDVIAQRHFVTHWDNKNEITVYPLAKRYTFLLACRLFMSVEDENHVAKFSDPF

QLIAAGIISLPIDLPGTPFNKAIKASNFIRKELIKIIKQRRVDLAEGTASPTQDILSHMLLTSDENGK

SMNELNIADKILGLLIGGHDTASVACTFLVKYLGELPHIYDKVYQEQMEIAKSKPAGELLNWDDLKKM

KYSWNVACEVMRLSPPLQGGFREAITDFMFNGFSIPKGWKLYWSANSTHKNAECFPMPEKFDPTRFEG

NGPAPYTFVPFGGGPRMCPGKEYARLEILVFMHNLVKRFKWEKVIPDEKIIVDPFPIPAKDLPIRLYP

HKA****
```

SEQ ID NO: 29; AsHMGR (*Avena strigosa* HMG-CoA reductase) coding sequence (1689bp):
NB: full-length HMGR sequence is provided below. The 5' region (underlined) can be removed to generate a truncated feedback-insensitive form (tHMGR). The sequence for tHMGR is also given separately below.

```
ATGGCTGTGGAGGTTCACCGCCGGGCTCCCGCGCCCCATGGCCGGGGCACCGGGGAGAAGGCCGCGT

GCAGGCCGGGGACGCGCTGCCGCTGCCGATCCGCCACACCAACCTCATCTTCTCGGCGCTCTTCGCCG

CCTCCCTCGCATACCTCATGCGCCGCTGGAGGGAGAAGATCCGCAACTCCACGCCGCTCCACGTCGTG

GGGCTCACCGAGATCTTCGCCATCTGCGGCCTCGTCGCCTCCCTCATCTACCTCCTCAGCTTCTTCGG

CATCGCCTTCGTGCAGTCCGTCGTATCCAACAGCGACGACGAGGACGAGGACTTCCTCATCGCGGCTG

CAGCATCCCAGGCCCCCCGCCGCCCTCCTCCAAGCCCGCGCCGCAGCAGTGCGCCCTGCTGCAGAGC

GCCGGAGTCGCGCCCGAGAAAATGCCCGAGGAGGACGAGGAAATCGTCGCCGGGGTCGTCGCAGGGAA

GATCCCCTCCTACGTGCTCGAGACCAGGCTAGGCGACTGCCGCAGGGCAGCCGGGATCCGCCGCGAGG

CGCTGCGCCGGATCACCGGCAGGGAGATCGACGGCCTTCCCCTCGACGGCTTCGACTACGACTCGATT

CTCGGACAGTGCTGCGAGATGCCCGTCGGGTACGTGCAGCTGCCGGTCGGCGTCGCGGGGCCGCTCGT

CCTCGACGGCCGCCGCATATACGTCCCGATGGCCACCACGGAGGGCTGCCTAATCGCCAGCACCAACC

GCGGATGCAAGGCCATTGCCGAGTCCGGAGGCGCATCCAGCGTCGTGTACCGCGACGGGATGACCCGC

GCCCCCGTAGCCCGCTTCCCCTCCGCACGACGCGCCGCAGAGCTCAAGGGCTTCCTGGAGAATCCGGC

CAACTACGACACCCTGTCCGTGGTCTTTAACAGATCAAGCAGATTTGCAAGGCTGCAGGGGGTCAAGT

GCGCCATGGCTGGGAGGAACTTGTACATGAGGTTCACCTGCAGCACCGGGGATGCCATGGGGATGAAC

ATGGTCTCCAAGGGCGTCCAAAATGTGCTCGACTATCTGCAGGAGGACTTCCCTGACATGGACGTTGT

CAGCATCTCAGGCAACTTTTGTTCCGACAAGAAATCAGCTGCTGTAAACTGGATTGAAGGCCGTGGAA

AGTCCGTGGTTTGTGAGGCAGTAATCAGAGAGGAAGTTGTCCACAAGGTTCTCAAGACCAACGTTCAG

TCACTCGTGGAGTTGAATGTGATCAAGAACCTTGCTGGCTCAGCAGTTGCTGGTGCTCTTGGGGGTTT

CAACGCCCACGCAAGCAACATCGTAACGGCTATCTTCATTGCCACTGGTCAGGATCCTGCACAGAATG

TGGAGAGCTCACAGTGTATCACTATGTTGGAAGCTGTAAATGATGGCAGAGACCTTCACATCTCCGTT
```

```
ACAATGCCATCTATCGAGGTGGGCACAGTTGGTGGAGGCACGCAGCTGGCCTCACAGTCGGCCTGCTT

GGACCTACTGGGCGTCAAAGGCGCCAACAGGGAATCTCCGGGGTCGAACGCTAGGCTGCTGGCCACGG

TGGTGGCTGGTGCCGTCCTAGCTGGGGAGCTGTCCCTCATCTCCGCCCAAGCTGCCGGCCATCTGGTC

CAGAGCCACATGAAATACAACAGATCCAGCAAGGACATGTCCAAGATCGCCTGCTGA
```

SEQ ID NO: 30; AsHMGR (*Avena strigosa* HMG-CoA reductase) translated
nucleotide sequence (562aa):
```
MAVEVHRRAPAPHGRGTGEKGRVQAGDALPLPIRHTNLIFSALFAASLAYLMRRWREKIRNSTPLHVV

GLTEIFAICGLVASLIYLLSFFGIAFVQSVVSNSDDEDEDFLIAAAASQAPPPPSSKPAPQQCALLQS

AGVAPEKMPEEDEEIVAGVVAGKIPSYVLETRLGDCRRAAGIRREALRRITGREIDGLPLDGFDYDSI

LGQCCEMPVGYVQLPVGVAGPLVLDGRRIYVPMATTEGCLIASTNRGCKAIAESGGASSVVYRDGMTR

APVARFPSARRAAELKGFLENPANYDTLSVVFNRSSRFARLQGVKCAMAGRNLYMRFTCSTGDAMGMN

MVSKGVQNVLDYLQEDFPDMDVVSISGNFCSDKKSAAVNWIEGRGKSVVCEAVIREEVVHKVLKTNVQ

SLVELNVIKNLAGSAVAGALGGFNAHASNIVTAIFIATGQDPAQNVESSQCITMLEAVNDGRDLHISV

TMPSIEVGTVGGGTQLASQSACLDLLGVKGANRESPGSNARLLATVVAGAVLAGELSLISAQAAGHLV

QSHMKYNRSSKDMSKIAC*
```

SEQ ID NO: 31; AstHMGR (*Avena strigosa* truncated HMG-CoA reductase)
coding sequence (1275bp):
```
ATGGCGCCCGAGAAAATGCCCGAGGAGGACGAGGAAATCGTCGCCGGGGTCGTCGCAGGGAAGATCCC

CTCCTACGTGCTCGAGACCAGGCTAGGCGACTGCCGCAGGGCAGCCGGGATCCGCCGCGAGGCGCTGC

GCCGGATCACCGGCAGGGAGATCGACGGCCTTCCCCTCGACGGCTTCGACTACGACTCGATTCTCGGA

CAGTGCTGCGAGATGCCCGTCGGGTACGTGCAGCTGCCGGTCGGCGTCGCGGGGCCGCTCGTCCTCGA

CGGCCGCCGCATATACGTCCCGATGGCCACCACGGAGGGCTGCCTAATCGCCAGCACCAACCGCGGAT

GCAAGGCCATTGCCGAGTCCGGAGGCGCATCCAGCGTCGTGTACCGCGACGGGATGACCCGCGCCCCC

GTAGCCCGCTTCCCCTCCGCACGACGCGCCGCAGAGCTCAAGGGCTTCCTGGAGAATCCGGCCAACTA

CGACACCCTGTCCGTGGTCTTTAACAGATCAAGCAGATTTGCAAGGCTGCAGGGGGTCAAGTGCGCCA

TGGCTGGGAGGAACTTGTACATGAGGTTCACCTGCAGCACCGGGGATGCCATGGGGATGAACATGGTC

TCCAAGGGCGTCCAAAATGTGCTCGACTATCTGCAGGAGGACTTCCCTGACATGGACGTTGTCAGCAT

CTCAGGCAACTTTTGTTCCGACAAGAAATCAGCTGCTGTAAACTGGATTGAAGGCCGTGGAAAGTCCG

TGGTTTGTGAGGCAGTAATCAGAGAGGAAGTTGTCCACAAGGTTCTCAAGACCAACGTTCAGTCACTC

GTGGAGTTGAATGTGATCAAGAACCTTGCTGGCTCAGCAGTTGCTGGTGCTCTTGGGGGTTTCAACGC

CCACGCAAGCAACATCGTAACGGCTATCTTCATTGCCACTGGTCAGGATCCTGCACAGAATGTGGAGA

GCTCACAGTGTATCACTATGTTGGAAGCTGTAAATGATGGCAGAGACCTTCACATCTCCGTTACAATG

CCATCTATCGAGGTGGGCACAGTTGGTGGAGGCACGCAGCTGGCCTCACAGTCGGCCTGCTTGGACCT

ACTGGGCGTCAAAGGCGCCAACAGGGAATCTCCGGGGTCGAACGCTAGGCTGCTGGCCACGGTGGTGG

CTGGTGCCGTCCTAGCTGGGGAGCTGTCCCTCATCTCCGCCCAAGCTGCCGGCCATCTGGTCCAGAGC

CACATGAAATACAACAGATCCAGCAAGGACATGTCCAAGATCGCCTGCTGA
```

SEQ ID NO: 32; AstHMGR (*Avena strigosa* truncated HMG-CoA reductase)
translated nucleotide sequence (424aa):
```
MAPEKMPEEDEEIVAGVVAGKIPSYVLETRLGDCRRAAGIRREALRRITGREIDGLPLDGFDYDSILG

QCCEMPVGYVQLPVGVAGPLVLDGRRIYVPMATTEGCLIASTNRGCKAIAESGGASSVVYRDGMTRAP

VARFPSARRAAELKGFLENPANYDTLSVVFNRSSRFARLQGVKCAMAGRNLYMRFTCSTGDAMGMNMV

SKGVQNVLDYLQEDFPDMDVVSISGNFCSDKKSAAVNWIEGRGKSVVCEAVIREEVVHKVLKTNVQSL
```

-continued

VELNVIKNLAGSAVAGALGGFNAHASNIVTAIFIATGQDPAQNVESSQCITMLEAVNDGRDLHISVTM

PSIEVGTVGGGTQLASQSACLDLLGVKGANRESPGSNARLLATVVAGAVLAGELSLISAQAAGHLVQS

HMKYNRSSKDMSKIAC****

SEQ ID NO: 33; AsSQS (Avena strigosa squalene synthase) coding
sequence (1212bp):
ATGGGGGCGCTGTCGCGGCCGGAGGAGGTGGTGGCGCTGGTCAAGCTGAGGGTGGCGGGGGGCAGAT

CAAGCGCCAGATCCCGGCCGAGGAACACTGGGCCTTCGCCTACGACATGCTCCAGAAGGTCTCCCGCA

GCTTCGCGCTCGTCATCCAGCAGCTCGGACCCGAACTCCGCAATGCCGTGTGCATCTTCTACCTCGTG

CTCCGGGCCCTGGACACCGTCGAGGACGACACCAGCATCCCCAACGACGTGAAGCTGCCCATCCTTCG

GGATTTCTACCGCCATGTCTACAACCCCGACTGGCGTTATTCATGTGGAACAAACCACTACAAGGTGC

TGATGGATAAGTTCAGACTCGTCTCCACGGCTTTCCTGGAGCTAGGCGAAGGATATCAAAAGGCAATT

GAAGAAATCACTAGGCGAATGGGAGCAGGAATGGCAAAATTTATATGCCAGGAGGTTGAAACGATTGA

TGACTATAATGAGTACTGCCACTATGTAGCAGGGCTAGTAGGCTATGGACTTTCCAGGCTCTTTCATG

CTGCTGGGACAGAAGATCTGGCTTCAGATCAACTTTCGAATTCAATGGGTTTGTTTCTTCAGAAAACC

AATATAATAAGGGATTATTTGGAGGATATAAATGAGATACCAAAGTGCCGTATGTTTTGGCCTCGAGA

AATATGGAGTAAATATGCAGATAAACTTGAGGACCTCAAGTATGAGGAAAATTCAGAAAAAGCAGTGC

AATGCTTGAATGATATGGTGACTAATGCTTTGGTCCACGCCGAAGACTGTCTTCAATACATGTCTGCG

TTGAAGGATAATACTAATTTTCGGTTTTGTGCAATACCTCAGATAATGGCAATTGGGACATGTGCTAT

TTGCTACAATAATGTGAAAGTCTTTAGAGGAGTTGTTAAGATGAGGCGTGGGCTCACTGCACGAATAA

TTGATGAGACAAAATCAATGTCAGATGTCTATTCTGCTTTCTATGAGTTCTCTTCATTGCTAGAGTCA

AAGATTGACGATAACGACCCAAGTTCTGCACTAACACGGAAGCGTGTAGAGGCAATAAAGAGGACTTG

CAAGTCATCCGGTTTACTAAAGAGAAGGGGATACGACCTGGAAAAGTCAAAGTATAGGCATATGTTGA

TCATGCTTGCACTTCTGTTGGTGGCTATTATCTTCGGTGTACTGTACGCCAAGTGA

SEQ ID NO: 34; AsSQS (Avena strigosa squalene synthase) translated
nucleotide sequence (403aa):
MGALSRPEEVVALVKLRVAAGQIKRQIPAEEHWAFAYDMLQKVSRSFALVIQQLGPELRNAVCIFYLV

LRALDTVEDDTSIPNDVKLPILRDFYRHVYNPDWRYSCGTNHYKVLMDKFRLVSTAFLELGEGYQKAI

EEITRRMGAGMAKFICQEVETIDDYNEYCHYVAGLVGYGLSRLFHAAGTEDLASDQLSNSMGLFLQKT

NIIRDYLEDINEIPKCRMFWPREIWSKYADKLEDLKYEENSEKAVQCLNDMVTNALVHAEDCLQYMSA

LKDNTNFRFCAIPQIMAIGTCAICYNNVKVFRGVVKMRRGLTARIIDETKSMSDVYSAFYEFSSLLES

KIDDNDPSSALTRKRVEAIKRTCKSSGLLKRRGYDLEKSKYRHMLIMLALLLVAIIFGVLYAK*

SEQ ID NO: 35; AtATR2 (Arabidopsis thali-
ana cytochrome P450 reductase
2) coding sequence (2325bp):
atgaaaaacatgatgaattataaattaaaactctgttctgtctcaaaaaactcaaaaggagtctctct ctcacctacaccacacctaaccaaaccccctacgattcacacagagagagatcttcttcttccttctt cttccttcttctttcttcttctttcttcttctagctacaacatctacaacgccatgtcctcttcttct tcttcgtcaacctccatgatcgatctcatggcagcaatcatcaaaggagagcctgtaattgtctccga cccagctaatgcctccgcttacgagtccgtagctgctgaattatcctctatgcttatagagaatcgtc aattcgccatgattgttaccacttccattgctgttcttattggttgcatcgttatgctcgtttggagg agatccggttctgggaattcaaaacgtgtcgagcctcttaagcctttggttattaagcctcgtgagga agagattgatgatgggcgtaagaaagttaccatcttttttcggtacacaaactggtactgctgaaggtt ttgcaaaggctttaggagaagaagctaaagcaagatatgaaaagaccagattcaaaatcgttgatttg gatgattacgcggctgatgatgatgagtatgaggagaaattgaagaaagaggatgtggctttcttctt -continued

```
cttagccacatatggagatggtgagcctaccgacaatgcagcgagattctacaaatggttcaccgagg ggaatgacagaggagaatggcttaagaacttgaagtatggagtgtttggattaggaaacagacaatat gagcattttaataaggttgccaaagttgtagatgacattcttgtcgaacaaggtgcacagcgtcttgt acaagttggtcttggagatgatgaccagtgtattgaagatgactttaccgcttggcgagaagcattgt ggcccgagcttgatacaatactgagggaagaaggggatacagctgttgccacaccatacactgcagct gtgttagaatacagagtttctattcacgactctgaagatgccaaattcaatgatataaacatggcaaa tgggaatggttacactgtgtttgatgctcaacatccttacaaagcaaatgtcgctgttaaaagggagc ttcatactcccgagtctgatcgttcttgtatccatttggaatttgacattgctggaagtggacttacg tatgaaactggagatcatgttggtgtactttgtgataacttaagtgaaactgtagatgaagctcttag attgctggatatgtcacctgatacttatttctcacttcacgctgaaaaagaagacggcacaccaatca gcagctcactgcctcctcccttcccaccttgcaacttgagaacagcgcttacacgatatgcatgtctt ttgagttctccaaagaagtctgctttagttgcgttggctgctcatgcatctgatcctaccgaagcaga acgattaaaacaccttgcttcacctgctggaaaggatgaatattcaaagtgggtagtagagagtcaaa gaagtctacttgaggtgatggccgagtttccttcagccaagccaccacttggtgtcttcttcgctgga gttgctccaaggttgcagcctaggttctattcgatatcatcatcgcccaagattgctgaaactagaat tcacgtcacatgtgcactggtttatgagaaaatgccaactggcaggattcataagggagtgtgttcca cttggatgaagaatgctgtgccttacgagaagagtgaaaactgttcctcggcgccgatatttgttagg caatccaacttcaagcttccttctgattctaaggtaccgatcatcatgatcggtccagggactggatt agctccattcagaggattccttcaggaaagactagcgttggtagaatctggtgttgaacttgggccat cagttttgttctttggatgcagaaaccgtagaatggatttcatctacgaggaagagctccagcgattt gttgagagtggtgctctcgcagagctaagtgtcgccttctctcgtgaaggacccaccaaagaatacgt acagcacaagatgatggacaaggcttctgatatctggaatatgatctctcaaggagcttatttatatg tttgtggtgacgccaaaggcatggcaagagatgttcacagatctctccacacaatagctcaagaacag gggtcaatggattcaactaaagcagagggcttcgtgaagaatctgcaaacgagtggaagatatcttag agatgtatggtaa
```

SEQ ID NO: 36; AtATR2 (*Arabidopsis thaliana* cytochrome P450 reductase 2) translated nucleotide sequence (774aa):
MKNMMNYKLKLCSVSKNSKGVSLSPTPHLTKPPTIHTERDLLLPSSSFFFLLLSSSSYNIYNAMSSSS

SSSTSMIDLMAAIIKGEPVIVSDPANASAYESVAAELSSMLIENRQFAMIVTTSIAVLIGCIVMLVWR

RSGSGNSKRVEPLKPLVIKPREEEIDDGRKKVTIFFGTQTGTAEGFAKALGEEAKARYEKTRFKIVDL

DDYAADDDEYEEKLKKEDVAFFFLATYGDGEPTDNAARFYKWFTEGNDRGEWLKNLKYGVFGLGNRQY

EHFNKVAKVVDDILVEQGAQRLVQVGLGDDDQCIEDDFTAWREALWPELDTILREEGDTAVATPYTAA

VLEYRVSIHDSEDAKFNDINMANGNGYTVFDAQHPYKANVAVKRELHTPESDRSCIHLEFDIAGSGLT

YETGDHVGVLCDNLSETVDEALRLLDMSPDTYFSLHAEKEDGTPISSSLPPPFPPCNLRTALTRYACL

LSSPKKSALVALAAHASDPTEAERLKHLASPAGKDEYSKWVVESQRSLLEVMAEFPSAKPPLGVFFAG

VAPRLQPRFYSISSSPKIAETRIHVTCALVYEKMPTGRIHKGVCSTWMKNAVPYEKSENCSSAPIFVR

QSNFKLPSDSKVPIIMIGPGTGLAPFRGFLQERLALVESGVELGPSVLFFGCRNRRMDFIYEEELQRF

VESGALAELSVAFSREGPTKEYVQHKMMDKASDIWNMISQGAYLYVCGDAKGMARDVHRSLHTIAQEQ

GSMDSTKAEGFVKNLQTSGRYLRDVW*

The invention claimed is:

1. A method of converting a host from a phenotype whereby the host is unable to carry out quillaic acid (QA) biosynthesis from 2,3-oxidosqualene (OS) to a phenotype whereby the host is able to carry out said QA biosynthesis, which method comprises the step of expressing a heterologous nucleic acid within the host or one or more cells thereof, following an earlier step of introducing the nucleic acid into the host or an ancestor of either,
wherein the heterologous nucleic acid comprises a plurality of nucleotide sequences each of which encodes a polypeptide which in combination have said QA biosynthesis activity,
wherein the nucleic acid encodes all of the following polypeptides:
  (i) a β-amyrin synthase (bAS) for cyclisation of OS to a triterpene, wherein the bAS has an amino acid sequence that is at least 90% identical to SEQ ID NO: 2;
  (ii) a C-28 oxidase capable of oxidising β-amyrin or an oxidised derivative thereof at the C-28 position to a carboxylic acid, wherein the CYP450 C-28 oxidase has an amino acid sequence that is at least 90% identical to SEQ ID NO: 4, SEQ ID NO: 18 or a polypeptide the encoded by any of SEQ ID NOs: 19-28;
  (iii) a C-16α oxidase capable of oxidising β-amyrin or an oxidised derivative thereof at the C-16α position to an alcohol, wherein the C-16α oxidase has an amino acid sequence that is at least 90% identical to any of SEQ ID NOS: 6, 10 or 12; and
  (iv) a C-23 oxidase capable of oxidising β-amyrin or an oxidised derivative thereof at the C-23 position to an aldehyde, wherein the C-16α oxidase has an amino acid sequence that is at least 90% identical to any of SEQ ID NOS: SEQ ID: No 8, 14 or 16.

2. A method as claimed in claim 1,
wherein each of the polypeptides is from *Quillaja saponaria*.

3. A method as claimed in claim 1 wherein each polypeptide is selected from the group consisting of:
  (i) the β-amyrin synthase (bAS) shown in SEQ ID: No 2;
  (ii) the C-28 oxidase shown in SEQ ID: No 4 or 18 or as encoded by any of SEQ ID NOs: 19-28;
  (iii) the C-16α oxidase shown in SEQ ID: No 6, 10 or 12; and
  (iv) the C-23 oxidase shown in SEQ ID: No 8, 14 or 16.

4. A method as claimed in claim 3 wherein each polypeptide is selected from the group consisting of:
  (i) the β-amyrin synthase (bAS) shown in SEQ ID: No 2;
  (ii) the C-28 oxidase shown in SEQ ID: No 4;
  (iii) the C-16α oxidase shown in SEQ ID: No 6; and
  (iv) the C-23 oxidase shown in the SEQ ID: No 8.

5. A method as claimed in claim 1 wherein the nucleic acid further encodes one or more of the following polypeptides:
  (i) an HMG-CoA reductase (HMGR); and
  (ii) a squalene synthase (SQS).

6. A method as claimed in claim 1 wherein the nucleotide sequences are present on two or more different nucleic acid molecules.

7. A method as claimed in claim 6 wherein the nucleic acid molecules are introduced by co-infiltration of a plurality of *Agrobacterium tumefaciens* strains each carrying one or more of the nucleic acid molecules.

8. A method as claimed in claim 7 wherein the nucleic acid molecules are transient expression vectors, wherein each of the transient expression vectors comprises an expression cassette comprising:
  (i) a promoter, operably linked to
  (ii) an enhancer sequence derived from the RNA-2 genome segment of a bipartite RNA virus, in which a target initiation site in the RNA-2 genome segment has been mutated;
  (iii) a nucleotide sequence encoding one of the polypeptides which in combination have said QA biosynthesis activity;
  (iv) a terminator sequence; and optionally
  (v) a 3' UTR located upstream of said terminator sequence.

9. A host cell containing or transformed with a heterologous nucleic acid which comprises a plurality of nucleotide sequences each of which encodes a polypeptide which in combination have quillaic acid (QA) from 2,3-oxidosqualene (OS) biosynthesis activity,
wherein the heterologous nucleic acid encodes all of the following polypeptides:
  (i) a β-amyrin synthase (bAS) for cyclisation of OS to a triterpene, wherein the bAS has an amino acid sequence that is at least 90% identical to SEQ ID NO: 2;
  (ii) a C-28 oxidase capable of oxidising β-amyrin or an oxidised derivative thereof at the C-28 position to a carboxylic acid, wherein the CYP450 C-28 oxidase has an amino acid sequence that is at least 90% identical to SEQ ID NO: 4, SEQ ID NO: 18 or a polypeptide the encoded by any of SEQ ID NOs: 19-28;
  (iii) a C-16α oxidase capable of oxidising β-amyrin or an oxidised derivative thereof at the C-16α position to an alcohol, wherein the C-16α oxidase has an amino acid sequence that is at least 90% identical to any of SEQ ID NOS: 6, 10 or 12; and (iv) a C-23 oxidase capable of oxidising β-amyrin or an oxidised derivative thereof at the C-23 position to an aldehyde, wherein the C-16α oxidase has an amino acid sequence that is at least 90% identical to any of SEQ ID NOS: SEQ ID: No 8, 14 or 16; and wherein expression of said nucleic acid imparts on the transformed host the ability to carry out QA biosynthesis.

10. A host cell as claimed in claim 9 wherein each of the polypeptides is obtained from *Q. saponaria*.

11. A process for producing the host cell of claim 9 comprising co-infiltrating a plurality of recombinant constructs comprising said heterologous nucleic acid into the cell for transient expression thereof.

12. A process for producing the host cell of claim 9 by transforming a cell with heterologous nucleic acid by introducing said heterologous nucleic acid into the cell via a vector and causing or allowing recombination between the vector and the cell genome to introduce the nucleic acid into the genome.

13. A method of claim 12, wherein the host cell is a plant cell and the method further comprises
regenerating a plant from a transformed plant cell.

14. A transgenic plant which is obtained by the method of claim 13, or which is a clone, or selfed or hybrid progeny or other descendant of said transgenic plant, wherein the transgenic plant comprises the heterologous nucleic acid and the plant is able to carry out QA synthesis.

15. A plant as claimed in claim 14 which is a crop plant or a moss.

16. A host cell as claimed in claim 9 which is a microorganism.

17. A host cell as claimed in claim 16 which is a yeast.

18. A host cell as claimed in claim 17 which further contains or is transformed with heterologous nucleic acid which comprises one or more nucleotide sequences each of which encodes a polypeptide which is a plant cytochrome P450 reductases (CPR).

19. A host cell as claimed in claim 18 wherein the CPR is shown in SEQ ID No: 35 or is a substantially homologous variant or fragment of said polypeptide.

20. A method of producing a product which is QA or a derivative thereof in a heterologous host, which method comprises culturing a host cell as claimed in claim 9.

21. A method of producing a product which is QA or a derivative thereof in a heterologous host, which method comprises growing a plant as claimed in claim 14 and then harvesting it and purifying the product therefrom.

22. A host cell containing or transformed with nucleic acids encoding:
(i) a β-amyrin synthase (bAS) for cyclisation of OS to a triterpene, wherein the bAS has an amino acid sequence that is at least 90% identical to SEQ ID NO: 2;
(ii) a C-28 oxidase capable of oxidising β-amyrin or an oxidised derivative thereof at the C-28 position to a carboxylic acid, wherein the CYP450 C-28 oxidase has an amino acid sequence that is at least 90% identical to SEQ ID NO: 4, SEQ ID NO: 18 or a polypeptide the encoded by any of SEQ ID NOs: 19-28;
(iii) a C-16α oxidase capable of oxidising β-amyrin or an oxidised derivative thereof at the C-16α position to an alcohol, wherein the C-16α oxidase has an amino acid sequence that is at least 90% identical to any of SEQ ID NOS: 6, 10 or 12; and
(iv) a C-23 oxidase capable of oxidising β-amyrin or an oxidised derivative thereof at the C-23 position to an aldehyde, wherein the C-16α oxidase has an amino acid sequence that is at least 90% identical to any of SEQ ID NOS: SEQ ID: No 8, 14 or 16, wherein the host cell carries out QA biosynthesis.

23. A host cell as claimed in claim 22 which is microbial.

24. A host cell of claim 22, wherein host cell is a plant and the nucleic acids are integrated into one or more chromosomes of the plant.

* * * * *

SEQUENCE LISTING

<160> NUMBER OF SEQ ID NOS: 45

<210> SEQ ID NO 1
<211> LENGTH: 2277
<212> TYPE: DNA
<213> ORGANISM: Quillaja saponaria

<400> SEQUENCE: 1

```
atgtggaggc tgaagatagc agaaggtggt tccgatccat atctgttcag cacaaacaac      60
ttcgtgggtc gccagacatg ggagttcgaa ccggaggccg gcacacctga ggagcgagca     120
gaggtcgaag ctgcccgcca aaacttttac aacaaccgtt accaggtcaa gccctgtgac     180
gacctccttt ggagatatca gttcctgaga gagaagaatt tcaaacaaac aataccgcct     240
gtcaaggttg aagatggcca agaaattact tatgagatgg ccacaacctc aatgcagagg     300
gcggcccgtc acctatcagc cttgcaggcc agcgatggcc attggccagc tcaaattgct     360
ggccccttgt tcttcatgcc acccttggtc ttttgtgtgt acattactgg gcatcttaat     420
acagtattcc catctgaaca tcgcaaagaa atccttcgtt acatgtacta tcaccagaac     480
gaagatggtg ggtggggact gcacatagag ggtcacagca ccatgttttg cacagcactc     540
aactacattt gtatgcgtat ccttggggaa ggaccagagg ggggtcaaga caatgcttgt     600
gccagagcac gaatgtggat tcttgatcat ggtggtgtaa cacatattcc atcttgggga     660
aagacctggc tttcgatact tggtctattt gagtggtctg gaagcaatcc aatgcctcca     720
gagttttgga tccttccttc atttcttcct atgcatccag caaaaatgtg gtgctattgc     780
cggatggttt acatgcccat gtcttattta tgggaaaaa ggtttgttgg cccaatcacg     840
cctctcattg ttcagttaag agaggaaata cacactcaaa attaccatga atcaactgg      900
aagtcagtcc gccatctatg tgcaaaggag gatatctact atccccatcc actcatccaa     960
gatttgattt gggacagttt gtacatacta acggagcctc ttctcactcg ctggcccttg    1020
aacaagttgg tgcgggagag ggctctccaa gtaacaatga agcatatcca ctatgaagat    1080
gaaaatagtc gatacataac cattggatgt gtggaaaagg tgttatgtat gcttgcttgt    1140
tgggttgatg atccaaatgg agatgctttc aagaagcacc ttgctcgagt cccagattac    1200
gtatgggtct ctgaagatgg aattactatg cagagttttg gtagtcaaga atgggatgct    1260
ggctttgccg tccaggctct gcttgcttct aatcttaccg aggaacttgg ccctgctctt    1320
gccaaaggac atgacttcat aaagcaatct caggttaagg acaatccttc aggtgacttc    1380
aaaagcatgt atcgtcacat ttctagagga tcatggacct tctctgacca agatcatgga    1440
tggcaagttt ctgattgcac tgcagaaggt ctgaagtgtt gcctgctttt gtcgatgttg    1500
ccaccagaaa ttgttggtga aaaatggaa ccacaaaggc tatttgattc tgtcaatgtg    1560
ctgctctctc tacagagcaa aaaaggtggt ttagctgcct gggagccagc agggcgcaa    1620
gattggttgg aattactcaa tcccacagaa ttttttgcgg acattgtcgt tgagcatgaa    1680
tatgttgaat gtactggatc agcaattcag gcattagttt tgttcaagaa gctgtatccg    1740
gggcacagga aaaagagat tgacagtttc attacaaatg ctgtccggtt ccttgagaat    1800
acacaaacgg cagatggctc ttggtatgga aactggggag tttgcttcac ctatggttgt    1860
tggttcgcac tgggagggct agcagcagct ggcaagactt acaacaactg tcctgcaata    1920
cgcaaagctg ttaattttcct acttacaaca caagagaag acggtggttg gggagaaagc    1980
tatcttcaa gccaaaaaa gatatatgta cccctggaag gaagccgatc aaatgtggta    2040
catactgcat gggctatgat gggtctaatt catgctgggc aggctgaaag agactcaact    2100
```

```
cctcttcatc gtgcagcaaa gttgatcatc aattatcaac tagaaaatgg cgattggccg    2160
caacaggaaa tcactggagt attcatgaaa aactgcatgt tacattaccc tatgtacaga    2220
aacatctacc caatgtgggc tcttgcagaa taccggaggc gggttccatt gccttaa      2277
```

<210> SEQ ID NO 2
<211> LENGTH: 758
<212> TYPE: PRT
<213> ORGANISM: Quillaja saponaria

<400> SEQUENCE: 2

```
Met Trp Arg Leu Lys Ile Ala Glu Gly Gly Ser Asp Pro Tyr Leu Phe
1               5                   10                  15

Ser Thr Asn Asn Phe Val Gly Arg Gln Thr Trp Glu Phe Glu Pro Glu
            20                  25                  30

Ala Gly Thr Pro Glu Glu Arg Ala Glu Val Glu Ala Ala Arg Gln Asn
        35                  40                  45

Phe Tyr Asn Asn Arg Tyr Gln Val Lys Pro Cys Asp Asp Leu Leu Trp
    50                  55                  60

Arg Tyr Gln Phe Leu Arg Glu Lys Asn Phe Lys Gln Thr Ile Pro Pro
65                  70                  75                  80

Val Lys Val Glu Asp Gly Gln Glu Ile Thr Tyr Glu Met Ala Thr Thr
                85                  90                  95

Ser Met Gln Arg Ala Ala Arg His Leu Ser Ala Leu Gln Ala Ser Asp
            100                 105                 110

Gly His Trp Pro Ala Gln Ile Ala Gly Pro Leu Phe Phe Met Pro Pro
        115                 120                 125

Leu Val Phe Cys Val Tyr Ile Thr Gly His Leu Asn Thr Val Phe Pro
    130                 135                 140

Ser Glu His Arg Lys Glu Ile Leu Arg Tyr Met Tyr His Gln Asn
145                 150                 155                 160

Glu Asp Gly Gly Trp Gly Leu His Ile Glu Gly His Ser Thr Met Phe
                165                 170                 175

Cys Thr Ala Leu Asn Tyr Ile Cys Met Arg Ile Leu Gly Glu Gly Pro
            180                 185                 190

Glu Gly Gly Gln Asp Asn Ala Cys Ala Arg Ala Arg Met Trp Ile Leu
        195                 200                 205

Asp His Gly Gly Val Thr His Ile Pro Ser Trp Gly Lys Thr Trp Leu
    210                 215                 220

Ser Ile Leu Gly Leu Phe Glu Trp Ser Gly Ser Asn Pro Met Pro Pro
225                 230                 235                 240

Glu Phe Trp Ile Leu Pro Ser Phe Leu Pro Met His Pro Ala Lys Met
                245                 250                 255

Trp Cys Tyr Cys Arg Met Val Tyr Met Pro Met Ser Tyr Leu Tyr Gly
            260                 265                 270

Lys Arg Phe Val Gly Pro Ile Thr Pro Leu Ile Val Gln Leu Arg Glu
        275                 280                 285

Glu Ile His Thr Gln Asn Tyr His Glu Ile Asn Trp Lys Ser Val Arg
    290                 295                 300

His Leu Cys Ala Lys Glu Asp Ile Tyr Tyr Pro His Pro Leu Ile Gln
305                 310                 315                 320

Asp Leu Ile Trp Asp Ser Leu Tyr Ile Leu Thr Glu Pro Leu Leu Thr
                325                 330                 335

Arg Trp Pro Leu Asn Lys Leu Val Arg Glu Arg Ala Leu Gln Val Thr
```

-continued

```
                340                 345                 350
Met Lys His Ile His Tyr Glu Asp Glu Asn Ser Arg Tyr Ile Thr Ile
            355                 360                 365
Gly Cys Val Glu Lys Val Leu Cys Met Leu Ala Cys Trp Val Asp Asp
        370                 375                 380
Pro Asn Gly Asp Ala Phe Lys Lys His Leu Ala Arg Val Pro Asp Tyr
385                 390                 395                 400
Val Trp Val Ser Glu Asp Gly Ile Thr Met Gln Ser Phe Gly Ser Gln
                405                 410                 415
Glu Trp Asp Ala Gly Phe Ala Val Gln Ala Leu Leu Ala Ser Asn Leu
            420                 425                 430
Thr Glu Glu Leu Gly Pro Ala Leu Ala Lys Gly His Asp Phe Ile Lys
        435                 440                 445
Gln Ser Gln Val Lys Asp Asn Pro Ser Gly Asp Phe Lys Ser Met Tyr
    450                 455                 460
Arg His Ile Ser Arg Gly Ser Trp Thr Phe Ser Asp Gln Asp His Gly
465                 470                 475                 480
Trp Gln Val Ser Asp Cys Thr Ala Glu Gly Leu Lys Cys Cys Leu Leu
                485                 490                 495
Leu Ser Met Leu Pro Pro Glu Ile Val Gly Glu Lys Met Glu Pro Gln
            500                 505                 510
Arg Leu Phe Asp Ser Val Asn Val Leu Leu Ser Leu Gln Ser Lys Lys
        515                 520                 525
Gly Gly Leu Ala Ala Trp Glu Pro Ala Gly Ala Gln Asp Trp Leu Glu
    530                 535                 540
Leu Leu Asn Pro Thr Glu Phe Phe Ala Asp Ile Val Val Glu His Glu
545                 550                 555                 560
Tyr Val Glu Cys Thr Gly Ser Ala Ile Gln Ala Leu Val Leu Phe Lys
                565                 570                 575
Lys Leu Tyr Pro Gly His Arg Lys Lys Glu Ile Asp Ser Phe Ile Thr
            580                 585                 590
Asn Ala Val Arg Phe Leu Glu Asn Thr Gln Thr Ala Asp Gly Ser Trp
        595                 600                 605
Tyr Gly Asn Trp Gly Val Cys Phe Thr Tyr Gly Cys Trp Phe Ala Leu
    610                 615                 620
Gly Gly Leu Ala Ala Gly Lys Thr Tyr Asn Asn Cys Pro Ala Ile
625                 630                 635                 640
Arg Lys Ala Val Asn Phe Leu Leu Thr Thr Gln Arg Glu Asp Gly Gly
                645                 650                 655
Trp Gly Glu Ser Tyr Leu Ser Ser Pro Lys Lys Ile Tyr Val Pro Leu
            660                 665                 670
Glu Gly Ser Arg Ser Asn Val Val His Thr Ala Trp Ala Met Met Gly
        675                 680                 685
Leu Ile His Ala Gly Gln Ala Glu Arg Asp Ser Thr Pro Leu His Arg
    690                 695                 700
Ala Ala Lys Leu Ile Ile Asn Tyr Gln Leu Glu Asn Gly Asp Trp Pro
705                 710                 715                 720
Gln Gln Glu Ile Thr Gly Val Phe Met Lys Asn Cys Met Leu His Tyr
                725                 730                 735
Pro Met Tyr Arg Asn Ile Tyr Pro Met Trp Ala Leu Ala Glu Tyr Arg
            740                 745                 750
Arg Arg Val Pro Leu Pro
        755
```

<210> SEQ ID NO 3
<211> LENGTH: 1443
<212> TYPE: DNA
<213> ORGANISM: Quillaja saponaria

<400> SEQUENCE: 3

| | | |
|---|---|---|
| atggagcact tgtatctctc ccttgtgctc ctgtttgttt cctcaatctc cctctccctc | 60 |
| ttcttcctgt tctacaaaca caaatctatg ttcaccgggg ccaacctacc acctggtaaa | 120 |
| atcggttacc cattgatcgg agagagcttg agttcttgt ccacgggatg aagggccac | 180 |
| ccggagaaat tcatcttcga tcgcatgagc aagtactcat cccaaatctt caagacctcg | 240 |
| attttagggg aaccaacggc ggtgttcccg ggagccgtat gcaacaagtt cctcttctcc | 300 |
| aacgagaaca agctggtgaa tgcatggtgg cctgcctccg tggacaagat ctttccttcc | 360 |
| tcactccaga catcctccaa agaagaggcc aagaagatga ggaagttgct tcctcagttt | 420 |
| ctcaagcccg aagctctgca ccgctacatt ggtattatgg attctattgc cagagacac | 480 |
| tttgccgata gctgggaaaa caaaaaccaa gtcattgtct ttcctctagc aaagaggtat | 540 |
| actttctggc tggcttgccg tttgttcatt agcgtcgagg atccgaccca cgtatccaga | 600 |
| tttgctgacc cgttccaact tttggccgcc ggaatcatat caatcccaat cgacttgcca | 660 |
| gggacaccgt tccgcaaggc aatcaatgcg tcccagttca tcaggaagga attgttggcc | 720 |
| atcatcaggc agagaaagat cgatttgggt gaagggaagg catctccgac gcaggacata | 780 |
| ctgtctcaca tgttgctcac atgcgacgag aacggacaat acatgaatga attggacatt | 840 |
| gccgacaaga ttcttggctt gttggtcggc ggacatgaca ctgccagtgc cgcttgcact | 900 |
| ttcattgtca agttcctcgc tgagcttccc cacatttatg aacaagtcta caaggagcaa | 960 |
| atggagattg caaaatcaaa agtgccagga gagttgttga attgggagga catccaaaag | 1020 |
| atgaaatatt cgtggaacgt agcttgtgaa gtgatgagac ttgcccctcc actccaagga | 1080 |
| gctttcaggg aagccattac tgacttcgtc ttcaacggtt tctccattcc aaaaggctgg | 1140 |
| aagttgtact ggagcgcaaa ttccacccac aaaagtccgg attatttccc tgagcccgac | 1200 |
| aagttcgacc caactagatt cgaaggaaat ggacctgcgc cttacacctt tgttccattt | 1260 |
| gggggaggac ccaggatgtg cccgggcaaa gagtatgccc gattggaaat acttgtgttc | 1320 |
| atgcataact tggtgaagag gttcaagtgg gagaaattgg ttcctgatga aaagattgtg | 1380 |
| gttgatccaa tgcccattcc agcaagggt cttcctgttc gcctttatcc tcacaaagct | 1440 |
| tga | 1443 |

<210> SEQ ID NO 4
<211> LENGTH: 480
<212> TYPE: PRT
<213> ORGANISM: Quillaja saponaria

<400> SEQUENCE: 4

```
Met Glu His Leu Tyr Leu Ser Leu Val Leu Leu Phe Val Ser Ser Ile
1               5                   10                  15

Ser Leu Ser Leu Phe Phe Leu Phe Tyr Lys His Lys Ser Met Phe Thr
            20                  25                  30

Gly Ala Asn Leu Pro Pro Gly Lys Ile Gly Tyr Pro Leu Ile Gly Glu
        35                  40                  45

Ser Leu Glu Phe Leu Ser Thr Gly Trp Lys Gly His Pro Glu Lys Phe
    50                  55                  60
```

```
Ile Phe Asp Arg Met Ser Lys Tyr Ser Ser Gln Ile Phe Lys Thr Ser
 65                  70                  75                  80

Ile Leu Gly Glu Pro Thr Ala Val Phe Pro Gly Ala Val Cys Asn Lys
                 85                  90                  95

Phe Leu Phe Ser Asn Glu Asn Lys Leu Val Asn Ala Trp Trp Pro Ala
            100                 105                 110

Ser Val Asp Lys Ile Phe Pro Ser Ser Leu Gln Thr Ser Ser Lys Glu
        115                 120                 125

Glu Ala Lys Lys Met Arg Lys Leu Leu Pro Gln Phe Leu Lys Pro Glu
    130                 135                 140

Ala Leu His Arg Tyr Ile Gly Ile Met Asp Ser Ile Ala Gln Arg His
145                 150                 155                 160

Phe Ala Asp Ser Trp Glu Asn Lys Asn Gln Val Ile Val Phe Pro Leu
                165                 170                 175

Ala Lys Arg Tyr Thr Phe Trp Leu Ala Cys Arg Leu Phe Ile Ser Val
            180                 185                 190

Glu Asp Pro Thr His Val Ser Arg Phe Ala Asp Pro Phe Gln Leu Leu
        195                 200                 205

Ala Ala Gly Ile Ile Ser Ile Pro Ile Asp Leu Pro Gly Thr Pro Phe
    210                 215                 220

Arg Lys Ala Ile Asn Ala Ser Gln Phe Ile Arg Lys Glu Leu Leu Ala
225                 230                 235                 240

Ile Ile Arg Gln Arg Lys Ile Asp Leu Gly Glu Gly Lys Ala Ser Pro
                245                 250                 255

Thr Gln Asp Ile Leu Ser His Met Leu Leu Thr Cys Asp Glu Asn Gly
            260                 265                 270

Gln Tyr Met Asn Glu Leu Asp Ile Ala Asp Lys Ile Leu Gly Leu Leu
        275                 280                 285

Val Gly Gly His Asp Thr Ala Ser Ala Ala Cys Thr Phe Ile Val Lys
    290                 295                 300

Phe Leu Ala Glu Leu Pro His Ile Tyr Glu Gln Val Tyr Lys Glu Gln
305                 310                 315                 320

Met Glu Ile Ala Lys Ser Lys Val Pro Gly Glu Leu Leu Asn Trp Glu
                325                 330                 335

Asp Ile Gln Lys Met Lys Tyr Ser Trp Asn Val Ala Cys Glu Val Met
            340                 345                 350

Arg Leu Ala Pro Pro Leu Gln Gly Ala Phe Arg Glu Ala Ile Thr Asp
        355                 360                 365

Phe Val Phe Asn Gly Phe Ser Ile Pro Lys Gly Trp Lys Leu Tyr Trp
    370                 375                 380

Ser Ala Asn Ser Thr His Lys Ser Pro Asp Tyr Phe Pro Glu Pro Asp
385                 390                 395                 400

Lys Phe Asp Pro Thr Arg Phe Glu Gly Asn Gly Pro Ala Pro Tyr Thr
                405                 410                 415

Phe Val Pro Phe Gly Gly Gly Pro Arg Met Cys Pro Gly Lys Glu Tyr
            420                 425                 430

Ala Arg Leu Glu Ile Leu Val Phe Met His Asn Leu Val Lys Arg Phe
        435                 440                 445

Lys Trp Glu Lys Leu Val Pro Asp Glu Lys Ile Val Val Asp Pro Met
    450                 455                 460

Pro Ile Pro Ala Lys Gly Leu Pro Val Arg Leu Tyr Pro His Lys Ala
465                 470                 475                 480
```

<210> SEQ ID NO 5
<211> LENGTH: 1506
<212> TYPE: DNA
<213> ORGANISM: Quillaja saponaria

<400> SEQUENCE: 5

```
atgatatata ataatgatag taatgataat gaattagtaa tcagctcagt tcagcaacca      60
tccatggatc ctttcttcat ttttggctta cttctcttgg ctctctttct ctctgtttct     120
tttcttctct acctttcccg tagagcctat gcttctctcc caaccctcc  gccggggaag     180
ctcggcttcc ccgtcgtcgg cgagagtctc gaatttctct ccacccgacg caaaggtgtt     240
cctgagaaat tcgtcttcga cagaatggcc aaatactgtc gggatgtctt aagacatca      300
atattgggag caaccaccgc cgtcatgtgc ggcaccgccg gtaacaaatt cttgttctcc     360
aacgagaaaa aacacgtcac tggttggtgg ccgaaatctg tagagctgat tttcccaacc     420
tcacttgaga atcatccaa  cgaagaatcc atcatgatga acaattcct  tcccaacttc     480
ttgaaaccag aacctttgca gaagtacata cccgttatgg acataattac caaagacac      540
ttcaatacaa gctgggaagg acgcaacgtg gtcaaagtgt ttcctacggc tgccgaattc     600
accacgttgc tggcttgtcg ggtattcctc agtgttgagg atcccattga agtagccaag     660
atttcagagc catttgaaat cttagctgct gggtttcttt caatacccat aaatcttccg     720
ggtaccaaat taaataaagc ggttaaggca gcggatcaga ttagagacgc aattgtacag     780
attttgaaac ggagaagggt tgaaattgcg gagaataaag caaatggaat gcaagatata     840
gcgtccatgt tgttgacgac accaactaat gctgggtttt atatgaccga ggctcacatt     900
tctgagaaaa ttttgggtat gattgttggt ggccgtgata ctgctagtac tgttatcacc     960
ttcatcatca gtatttggc  agagaatcct gaaatttata ataaggtcta tgaggagcaa    1020
atggaagtgg taaagtcaaa gaaaccaggt gagttgctga actgggaaga tgtgcagaaa    1080
atgaagtact cttggtgcgt agcatgtgaa gctatgcgac ttgctcctcc tgttcaaggt    1140
ggtttcaagg tggccattaa tgactttgtg tattctgggt tcaacattcg caagggttgg    1200
aagttatatt ggagtgccat tgcaacacac atgaatccag aatatttccc agaacctgag    1260
aaattcaacc cctcaaggtt tgaagggaag ggaccagtac cttacagctt cgtaccct tc    1320
ggaggcggac ctcggatgtg tcccgggaaa gagtattccc ggctggaaac acttgttttc    1380
atgcatcatt tggtgacgag gtacaattgg agaaagtgt  atcccacaga aagataaca     1440
gtggatccaa tgccattccc tgtcaacggc ctccccattc gccttattcc tcacaagcac    1500
caatga                                                               1506
```

<210> SEQ ID NO 6
<211> LENGTH: 501
<212> TYPE: PRT
<213> ORGANISM: Quillaja saponaria

<400> SEQUENCE: 6

```
Met Ile Tyr Asn Asn Asp Ser Asn Asp Asn Glu Leu Val Ile Ser Ser
1               5                   10                  15

Val Gln Gln Pro Ser Met Asp Pro Phe Phe Ile Phe Gly Leu Leu Leu
            20                  25                  30

Leu Ala Leu Phe Leu Ser Val Ser Phe Leu Leu Tyr Leu Ser Arg Arg
        35                  40                  45

Ala Tyr Ala Ser Leu Pro Asn Pro Pro Gly Lys Leu Gly Phe Pro
    50                  55                  60
```

```
Val Val Gly Glu Ser Leu Glu Phe Leu Ser Thr Arg Arg Lys Gly Val
 65                  70                  75                  80

Pro Glu Lys Phe Val Phe Asp Arg Met Ala Lys Tyr Cys Arg Asp Val
                 85                  90                  95

Phe Lys Thr Ser Ile Leu Gly Ala Thr Ala Val Met Cys Gly Thr
            100                 105                 110

Ala Gly Asn Lys Phe Leu Phe Ser Asn Glu Lys Lys His Val Thr Gly
            115                 120                 125

Trp Trp Pro Lys Ser Val Glu Leu Ile Phe Pro Thr Ser Leu Glu Lys
        130                 135                 140

Ser Ser Asn Glu Glu Ser Ile Met Met Lys Gln Phe Leu Pro Asn Phe
145                 150                 155                 160

Leu Lys Pro Glu Pro Leu Gln Lys Tyr Ile Pro Val Met Asp Ile Ile
                165                 170                 175

Thr Gln Arg His Phe Asn Thr Ser Trp Glu Gly Arg Asn Val Val Lys
            180                 185                 190

Val Phe Pro Thr Ala Ala Glu Phe Thr Thr Leu Leu Ala Cys Arg Val
        195                 200                 205

Phe Leu Ser Val Glu Asp Pro Ile Glu Val Ala Lys Ile Ser Glu Pro
        210                 215                 220

Phe Glu Ile Leu Ala Ala Gly Phe Leu Ser Ile Pro Ile Asn Leu Pro
225                 230                 235                 240

Gly Thr Lys Leu Asn Lys Ala Val Lys Ala Asp Gln Ile Arg Asp
                245                 250                 255

Ala Ile Val Gln Ile Leu Lys Arg Arg Arg Val Glu Ile Ala Glu Asn
                260                 265                 270

Lys Ala Asn Gly Met Gln Asp Ile Ala Ser Met Leu Leu Thr Thr Pro
            275                 280                 285

Thr Asn Ala Gly Phe Tyr Met Thr Glu Ala His Ile Ser Glu Lys Ile
            290                 295                 300

Leu Gly Met Ile Val Gly Gly Arg Asp Thr Ala Ser Thr Val Ile Thr
305                 310                 315                 320

Phe Ile Ile Lys Tyr Leu Ala Glu Asn Pro Glu Ile Tyr Asn Lys Val
                325                 330                 335

Tyr Glu Glu Gln Met Glu Val Val Lys Ser Lys Pro Gly Glu Leu
            340                 345                 350

Leu Asn Trp Glu Asp Val Gln Lys Met Lys Tyr Ser Trp Cys Val Ala
        355                 360                 365

Cys Glu Ala Met Arg Leu Ala Pro Pro Val Gln Gly Gly Phe Lys Val
        370                 375                 380

Ala Ile Asn Asp Phe Val Tyr Ser Gly Phe Asn Ile Arg Lys Gly Trp
385                 390                 395                 400

Lys Leu Tyr Trp Ser Ala Ile Ala Thr His Met Asn Pro Glu Tyr Phe
                405                 410                 415

Pro Glu Pro Glu Lys Phe Asn Pro Ser Arg Phe Glu Gly Lys Gly Pro
                420                 425                 430

Val Pro Tyr Ser Phe Val Pro Phe Gly Gly Gly Pro Arg Met Cys Pro
            435                 440                 445

Gly Lys Glu Tyr Ser Arg Leu Glu Thr Leu Val Phe Met His His Leu
            450                 455                 460

Val Thr Arg Tyr Asn Trp Glu Lys Val Tyr Pro Thr Glu Lys Ile Thr
465                 470                 475                 480

Val Asp Pro Met Pro Phe Pro Val Asn Gly Leu Pro Ile Arg Leu Ile
```

```
                485                 490                 495
Pro His Lys His Gln
        500
```

<210> SEQ ID NO 7
<211> LENGTH: 1524
<212> TYPE: DNA
<213> ORGANISM: Quillaja saponaria

<400> SEQUENCE: 7

```
atgtggttca cagtaggatt ggtcttggtt ttcgccctat tcatacgtct ctacagcagt    60
ctgtggttga agcctcgtgc aactcggatt aagcttagca atcaaggaat aaaggtcca    120
aaaccagcat tcttctggg taatgttgca gagatgagaa gatttcaatc taagcttcca    180
aaatctgaac tcaaacaagg ccaagtttct catgattggg cttctaaatc tctgtttcca    240
tttttcagtc tttggtccca gaaatacgga aatacgttcg tgttctcatt ggggaacata    300
caggtgctct atgtttctga tcatgagttg gtgaaagaaa ttaatcagaa tacctcttta    360
gatttgggca aacccaagta cctgcagaag gagcgtggcc ctttgctggg acaaggtatt    420
ttgacctcca atggacagct ttgggcgtac cagagaaaaa tcatgactcc tgaactctac    480
aaggagaaaa tcaagggcat gtgcgagttg atggtggaat ctgtagcttg gttggttgag    540
gaatggggaa cgaagatcca agctgagggt ggggcagcag acattagaat agacgaggat    600
cttagaagct tctctggtga tgtaatttca aaagcttgtt ttgggagctg ctatgccgga    660
gggagggaaa tctttcttag gctcagagct cttcaacacc aaattgcttc caaagcctta    720
ctcatgggct tccctggatt aaagtacctg cccattaaga gcaacagaga gatatggaga    780
ttggagaagg agatcttcca gctgattatg aagctggctg aagatagaaa aaagaacaa    840
catgagagag acctattaca gattataatt gagggagcta aagtagtga tctgagttcg    900
gaagcaatgg caaaattcat tgtggacaac tgcaagaatg tctacttggc tggccatgaa    960
actactgcaa tgtctgctgg ttggactttg cttctcttgg ctaatcatcc tgagtggcaa    1020
gcccgtgtcc gtgatgagat tttacaagtc accgagggcc gcaatcctga tttgacatg    1080
ctgcacaaga tgaaactgtt aacaatggta attcaggagg cactgcgact ctacccaaca    1140
gtcatattca tgtcaagaga agcattggaa gatattaatg ttggaaacat ccaagttcca    1200
aaaggtgtta acatatggat acctgtggta atcttcaaa gggacacaac ggtatggggt    1260
gcagacgcaa acgagtttaa tcctgaaagg tttgccaatg gagttaacaa ttcatgcaag    1320
gttccacaac tttacctacc atttggagct ggacctcgca tttgtcctgg aattaatctg    1380
gccatgactg agatcaagat acttctgtgt atcctgctca ccaagttttc gttttcagtt    1440
tcacccaact atcgccactc accggtgttt aaattggtgc ttgagcctga aaatggaatc    1500
aatgtcatca tgaagaagct ctaa                                          1524
```

<210> SEQ ID NO 8
<211> LENGTH: 507
<212> TYPE: PRT
<213> ORGANISM: Quillaja saponaria

<400> SEQUENCE: 8

```
Met Trp Phe Thr Val Gly Leu Val Leu Val Phe Ala Leu Phe Ile Arg
1               5                   10                  15

Leu Tyr Ser Ser Leu Trp Leu Lys Pro Arg Ala Thr Arg Ile Lys Leu
            20                  25                  30
```

```
Ser Asn Gln Gly Ile Lys Gly Pro Lys Pro Ala Phe Leu Gly Asn
        35                  40                  45

Val Ala Glu Met Arg Arg Phe Gln Ser Lys Leu Pro Lys Ser Glu Leu
 50                  55                  60

Lys Gln Gly Gln Val Ser His Asp Trp Ala Ser Lys Ser Leu Phe Pro
 65                  70                  75                  80

Phe Phe Ser Leu Trp Ser Gln Lys Tyr Gly Asn Thr Phe Val Phe Ser
                 85                  90                  95

Leu Gly Asn Ile Gln Val Leu Tyr Val Ser Asp His Glu Leu Val Lys
            100                 105                 110

Glu Ile Asn Gln Asn Thr Ser Leu Asp Leu Gly Lys Pro Lys Tyr Leu
            115                 120                 125

Gln Lys Glu Arg Gly Pro Leu Leu Gly Gln Gly Ile Leu Thr Ser Asn
130                 135                 140

Gly Gln Leu Trp Ala Tyr Gln Arg Lys Ile Met Thr Pro Glu Leu Tyr
145                 150                 155                 160

Lys Glu Lys Ile Lys Gly Met Cys Glu Leu Met Val Glu Ser Val Ala
                165                 170                 175

Trp Leu Val Glu Glu Trp Gly Thr Lys Ile Gln Ala Glu Gly Gly Ala
            180                 185                 190

Ala Asp Ile Arg Ile Asp Glu Asp Leu Arg Ser Phe Ser Gly Asp Val
            195                 200                 205

Ile Ser Lys Ala Cys Phe Gly Ser Cys Tyr Ala Gly Gly Arg Glu Ile
            210                 215                 220

Phe Leu Arg Leu Arg Ala Leu Gln His Gln Ile Ala Ser Lys Ala Leu
225                 230                 235                 240

Leu Met Gly Phe Pro Gly Leu Lys Tyr Leu Pro Ile Lys Ser Asn Arg
                245                 250                 255

Glu Ile Trp Arg Leu Glu Lys Glu Ile Phe Gln Leu Ile Met Lys Leu
            260                 265                 270

Ala Glu Asp Arg Lys Lys Glu Gln His Glu Arg Asp Leu Leu Gln Ile
            275                 280                 285

Ile Ile Glu Gly Ala Lys Ser Ser Asp Leu Ser Ser Glu Ala Met Ala
            290                 295                 300

Lys Phe Ile Val Asp Asn Cys Lys Asn Val Tyr Leu Ala Gly His Glu
305                 310                 315                 320

Thr Thr Ala Met Ser Ala Gly Trp Thr Leu Leu Leu Ala Asn His
                325                 330                 335

Pro Glu Trp Gln Ala Arg Val Arg Asp Glu Ile Leu Gln Val Thr Glu
            340                 345                 350

Gly Arg Asn Pro Asp Phe Asp Met Leu His Lys Met Lys Leu Leu Thr
            355                 360                 365

Met Val Ile Gln Glu Ala Leu Arg Leu Tyr Pro Thr Val Ile Phe Met
370                 375                 380

Ser Arg Glu Ala Leu Glu Asp Ile Asn Val Gly Asn Ile Gln Val Pro
385                 390                 395                 400

Lys Gly Val Asn Ile Trp Ile Pro Val Val Asn Leu Gln Arg Asp Thr
                405                 410                 415

Thr Val Trp Gly Ala Asp Ala Asn Glu Phe Asn Pro Glu Arg Phe Ala
            420                 425                 430

Asn Gly Val Asn Asn Ser Cys Lys Val Pro Gln Leu Tyr Leu Pro Phe
            435                 440                 445

Gly Ala Gly Pro Arg Ile Cys Pro Gly Ile Asn Leu Ala Met Thr Glu
```

```
                 450              455              460
Ile Lys Ile Leu Leu Cys Ile Leu Leu Thr Lys Phe Ser Phe Ser Val
465              470              475              480

Ser Pro Asn Tyr Arg His Ser Pro Val Phe Lys Leu Val Leu Glu Pro
                485              490              495

Glu Asn Gly Ile Asn Val Ile Met Lys Lys Leu
            500              505
```

<210> SEQ ID NO 9
<211> LENGTH: 1437
<212> TYPE: DNA
<213> ORGANISM: Bupleurum falcatum

<400> SEQUENCE: 9

```
atggaacttt ctatcactct gatgcttatt ttctcaacaa ccatcttctt tatatttcgt      60
aatgtgtaca accatctcat ctctaaacac aaaaactatc ccctggaag tatgggcttg     120
ccttacattg gcgaaacact tagtttcgcg agatacatca ccaaaggagt ccctgaaaaa    180
ttcgtaatag aaagacaaaa gaaatattca acaacaatat ttaagacctc cttgttcgga    240
gaaaacatgt ggtgttggg cagtgcagag ggcaacaaat ttattttggt aagcgaggag    300
aagtatttac gagtgtggtt ccaagttct gtggacaaag tgttcaaaaa atctcataag    360
agaacgtcgc aggaagaagc tattaggttg cgcaaaaaca tggtgccatt tctcaaagca    420
gatttgttga agttatgt accaataatg gacacattta tgaaacaaca tgtgaactcg    480
cattggaatt gcgagacctt gaaggcttgt cctgtgatca aggattttac gtttacttta    540
gcttgtaaac ttttttttag tgtagacaat cctttggagc tagagaagtt aatcaagcta    600
tttgtgaata tagtgaatgg cctccttacg gtccctattg atctcccggg acaaaattt    660
agaggagtta taaagagtgt caagactatt cgccatgcgc ttaaagtgtt gatcaggcaa    720
cgaaaggtgg atattagaga gaaaagagcc acacctacgc aagatatatt gtcgataatg    780
ctggcacagg ctgaggacga gaactatgaa atgaatgatg aagatgtggc caatgacttt    840
cttgcagttt tgcttgctag ttatgattct gccaatacta cactcaccat gattatgaaa    900
tatcttgctg aatatcccga atgtatgat cgagttttca gagaacaaat ggaggtggca    960
aagacgaaag aaaagatga attactcaac ttggacgact gcaaaagat gaattatact   1020
tggaatgtag cttgtgaagt actgagaatt gcaacaccaa cgttcggagc attcagagag   1080
gttattgcag attgtacata cgaagggtac accataccaa aaggctggaa gctatattat   1140
gccccgcgtt ttacccatgg aagtgcaaaa tactttcaag atccagagaa atttgatcca   1200
tcgcgatttg aaggtgatgg tgcgcctcct tatacattcg ttccattcgg aggagggctc   1260
cggatgtgcc ctggatacaa gtatgcaaag attatagtac tagtgttcat gcacaatata   1320
gttacaaagt tcaaatggga gaaagttaac cctaatgaga aatgacagt aggaatcgta   1380
tcagcgccaa gtcaaggact tccactgcgt ctccatcccc acaaatctcc atcttaa     1437
```

<210> SEQ ID NO 10
<211> LENGTH: 478
<212> TYPE: PRT
<213> ORGANISM: Bupleurum falcatum

<400> SEQUENCE: 10

```
Met Glu Leu Ser Ile Thr Leu Met Leu Ile Phe Ser Thr Thr Ile Phe
1               5                   10                  15

Phe Ile Phe Arg Asn Val Tyr Asn His Leu Ile Ser Lys His Lys Asn
```

-continued

```
                20                  25                  30
Tyr Pro Pro Gly Ser Met Gly Leu Pro Tyr Ile Gly Glu Thr Leu Ser
                35                  40                  45

Phe Ala Arg Tyr Ile Thr Lys Gly Val Pro Glu Lys Phe Val Ile Glu
 50                  55                  60

Arg Gln Lys Lys Tyr Ser Thr Thr Ile Phe Lys Thr Ser Leu Phe Gly
 65                  70                  75                  80

Glu Asn Met Val Val Leu Gly Ser Ala Glu Gly Asn Lys Phe Ile Phe
                85                  90                  95

Gly Ser Glu Glu Lys Tyr Leu Arg Val Trp Phe Pro Ser Ser Val Asp
                100                 105                 110

Lys Val Phe Lys Lys Ser His Lys Arg Thr Ser Gln Glu Glu Ala Ile
                115                 120                 125

Arg Leu Arg Lys Asn Met Val Pro Phe Leu Lys Ala Asp Leu Leu Arg
                130                 135                 140

Ser Tyr Val Pro Ile Met Asp Thr Phe Met Lys Gln His Val Asn Ser
145                 150                 155                 160

His Trp Asn Cys Glu Thr Leu Lys Ala Cys Pro Val Ile Lys Asp Phe
                165                 170                 175

Thr Phe Thr Leu Ala Cys Lys Leu Phe Phe Ser Val Asp Asn Pro Leu
                180                 185                 190

Glu Leu Glu Lys Leu Ile Lys Leu Phe Val Asn Ile Val Asn Gly Leu
                195                 200                 205

Leu Thr Val Pro Ile Asp Leu Pro Gly Thr Lys Phe Arg Gly Val Ile
                210                 215                 220

Lys Ser Val Lys Thr Ile Arg His Ala Leu Lys Val Leu Ile Arg Gln
225                 230                 235                 240

Arg Lys Val Asp Ile Arg Glu Lys Arg Ala Thr Pro Thr Gln Asp Ile
                245                 250                 255

Leu Ser Ile Met Leu Ala Gln Ala Glu Asp Glu Asn Tyr Glu Met Asn
                260                 265                 270

Asp Glu Asp Val Ala Asn Asp Phe Leu Ala Val Leu Leu Ala Ser Tyr
                275                 280                 285

Asp Ser Ala Asn Thr Thr Leu Thr Met Ile Met Lys Tyr Leu Ala Glu
                290                 295                 300

Tyr Pro Glu Met Tyr Asp Arg Val Phe Arg Glu Gln Met Glu Val Ala
305                 310                 315                 320

Lys Thr Lys Gly Lys Asp Glu Leu Leu Asn Leu Asp Asp Leu Gln Lys
                325                 330                 335

Met Asn Tyr Thr Trp Asn Val Ala Cys Glu Val Leu Arg Ile Ala Thr
                340                 345                 350

Pro Thr Phe Gly Ala Phe Arg Glu Val Ile Ala Asp Cys Thr Tyr Glu
                355                 360                 365

Gly Tyr Thr Ile Pro Lys Gly Trp Lys Leu Tyr Tyr Ala Pro Arg Phe
                370                 375                 380

Thr His Gly Ser Ala Lys Tyr Phe Gln Asp Pro Glu Lys Phe Asp Pro
385                 390                 395                 400

Ser Arg Phe Glu Gly Asp Gly Ala Pro Pro Tyr Thr Phe Val Pro Phe
                405                 410                 415

Gly Gly Gly Leu Arg Met Cys Pro Gly Tyr Lys Tyr Ala Lys Ile Ile
                420                 425                 430

Val Leu Val Phe Met His Asn Ile Val Thr Lys Phe Lys Trp Glu Lys
                435                 440                 445
```

Val Asn Pro Asn Glu Lys Met Thr Val Gly Ile Val Ser Ala Pro Ser
        450                 455                 460

Gln Gly Leu Pro Leu Arg Leu His Pro His Lys Ser Pro Ser
465                 470                 475

<210> SEQ ID NO 11
<211> LENGTH: 1428
<212> TYPE: DNA
<213> ORGANISM: Maesa lanceolata

<400> SEQUENCE: 11

| | | | | | |
|---|---|---|---|---|---|
| atgtgggtag | tgggattaat | tggtgtggct | gtggtaacaa | tattgataac | tcagtatgta | 60 |
| tacaaatgga | gaaatccaaa | gactgtgggt | gttctgccac | ctggttcaat | gggtctgcct | 120 |
| ttgatcgggg | agactcttca | acttctcagc | cgtaatccat | ccttggatct | tcatcctttc | 180 |
| atcaagagca | gaatccaaag | atatgggcag | atattcgcga | ccaatatcgt | aggtcgaccc | 240 |
| ataatagtaa | ccgctgatcc | gcagctcaat | aattaccttt | tccaacaaga | aggaagagca | 300 |
| gtagaactgt | ggtacttgga | cagctttcaa | aagctattta | acttagaagg | tgcaaacagg | 360 |
| ccgaacgcag | ttggtcacat | tcacaagtac | gttagaagtg | tatacttgag | tctcttttgg | 420 |
| gtcgagagcc | ttaaaacaaa | gttgcttgcc | gatattgaga | aacagtccg | caaaaatctt | 480 |
| attggtggga | caaccaaagg | cacctttgat | gcaaaacatg | cttctgccaa | tatggttgct | 540 |
| gtttttgctg | caaaatactt | gttcggacat | gattacgaga | atcgaaaga | agatgtaggc | 600 |
| agcataatcg | acaacttcgt | acaaggactt | ctcgcattcc | cattgaatgt | tcccggtaca | 660 |
| aagttccaca | aatgtatgaa | ggacaagaaa | aggctggaat | caatgatcac | taacaagcta | 720 |
| aaggagagaa | tagctgatcc | gaacagcgga | caagggatt | tccttgatca | agcagtgaaa | 780 |
| gacttgaata | gcgaattctt | cataacagag | acttttatcg | tttcggtgac | gatgggagct | 840 |
| ttatttgcga | cggttgaatc | ggtttcgaca | gcaattggac | tagctttcaa | gttttttgca | 900 |
| gagcacccct | gggttttgga | tgacctcaag | gctgagcatg | aggctgtcct | tagcaaaaga | 960 |
| gaggatagaa | attcacctct | cacgtgggac | gaatatagat | cgatgacaca | cacgatgcac | 1020 |
| tttatcaatg | aagtcgtccg | tttgggaaat | gttttttcctg | gaattttgag | gaaagcactg | 1080 |
| aaagatattc | catataatgg | ttatacaatt | ccgtccggtt | ggaccattat | gattgtgacc | 1140 |
| tctacccttg | cgatgaaccc | tgagatattc | aaggatcctc | ttgcattcaa | tccgaaacgt | 1200 |
| tggcgggata | ttgatcccga | aactcaaact | aaaaacttta | tgcctttcgg | tggtgggacg | 1260 |
| agacaatgcg | caggtgcaga | gctagccaag | gcattctttg | ctaccttcct | ccatgtttta | 1320 |
| atcagcgaat | atagctggaa | gaaagtgaag | ggaggaagcg | ttgctcggac | acctatgtta | 1380 |
| agttttgaag | atggcatatt | tattgaggtc | accaagaaaa | acaagtga | | 1428 |

<210> SEQ ID NO 12
<211> LENGTH: 475
<212> TYPE: PRT
<213> ORGANISM: Maesa lanceolata

<400> SEQUENCE: 12

Met Trp Val Val Gly Leu Ile Gly Val Ala Val Thr Ile Leu Ile
1               5                   10                  15

Thr Gln Tyr Val Tyr Lys Trp Arg Asn Pro Lys Thr Val Gly Val Leu
            20                  25                  30

Pro Pro Gly Ser Met Gly Leu Pro Leu Ile Gly Glu Thr Leu Gln Leu
        35                  40                  45

```
Leu Ser Arg Asn Pro Ser Leu Asp Leu His Pro Phe Ile Lys Ser Arg
    50                  55                  60

Ile Gln Arg Tyr Gly Gln Ile Phe Ala Thr Asn Ile Val Gly Arg Pro
65                  70                  75                  80

Ile Ile Val Thr Ala Asp Pro Gln Leu Asn Asn Tyr Leu Phe Gln Gln
                85                  90                  95

Glu Gly Arg Ala Val Glu Leu Trp Tyr Leu Asp Ser Phe Gln Lys Leu
            100                 105                 110

Phe Asn Leu Glu Gly Ala Asn Arg Pro Asn Ala Val Gly His Ile His
            115                 120                 125

Lys Tyr Val Arg Ser Val Tyr Leu Ser Leu Phe Gly Val Glu Ser Leu
    130                 135                 140

Lys Thr Lys Leu Leu Ala Asp Ile Glu Lys Thr Val Arg Lys Asn Leu
145                 150                 155                 160

Ile Gly Gly Thr Thr Lys Gly Thr Phe Asp Ala Lys His Ala Ser Ala
                165                 170                 175

Asn Met Val Ala Val Phe Ala Ala Lys Tyr Leu Phe Gly His Asp Tyr
            180                 185                 190

Glu Lys Ser Lys Glu Asp Val Gly Ser Ile Ile Asp Asn Phe Val Gln
    195                 200                 205

Gly Leu Leu Ala Phe Pro Leu Asn Val Pro Gly Thr Lys Phe His Lys
    210                 215                 220

Cys Met Lys Asp Lys Lys Arg Leu Glu Ser Met Ile Thr Asn Lys Leu
225                 230                 235                 240

Lys Glu Arg Ile Ala Asp Pro Asn Ser Gly Gln Gly Asp Phe Leu Asp
                245                 250                 255

Gln Ala Val Lys Asp Leu Asn Ser Glu Phe Phe Ile Thr Glu Thr Phe
            260                 265                 270

Ile Val Ser Val Thr Met Gly Ala Leu Phe Ala Thr Val Glu Ser Val
    275                 280                 285

Ser Thr Ala Ile Gly Leu Ala Phe Lys Phe Phe Ala Glu His Pro Trp
    290                 295                 300

Val Leu Asp Asp Leu Lys Ala Glu His Glu Ala Val Leu Ser Lys Arg
305                 310                 315                 320

Glu Asp Arg Asn Ser Pro Leu Thr Trp Asp Glu Tyr Arg Ser Met Thr
                325                 330                 335

His Thr Met His Phe Ile Asn Glu Val Val Arg Leu Gly Asn Val Phe
            340                 345                 350

Pro Gly Ile Leu Arg Lys Ala Leu Lys Asp Ile Pro Tyr Asn Gly Tyr
    355                 360                 365

Thr Ile Pro Ser Gly Trp Thr Ile Met Ile Val Thr Ser Thr Leu Ala
    370                 375                 380

Met Asn Pro Glu Ile Phe Lys Asp Pro Leu Ala Phe Asn Pro Lys Arg
385                 390                 395                 400

Trp Arg Asp Ile Asp Pro Glu Thr Gln Thr Lys Asn Phe Met Pro Phe
                405                 410                 415

Gly Gly Gly Thr Arg Gln Cys Ala Gly Ala Glu Leu Ala Lys Ala Phe
            420                 425                 430

Phe Ala Thr Phe Leu His Val Leu Ile Ser Glu Tyr Ser Trp Lys Lys
    435                 440                 445

Val Lys Gly Gly Ser Val Ala Arg Thr Pro Met Leu Ser Phe Glu Asp
    450                 455                 460
```

Gly Ile Phe Ile Glu Val Thr Lys Lys Asn Lys
465                 470                 475

<210> SEQ ID NO 13
<211> LENGTH: 1563
<212> TYPE: DNA
<213> ORGANISM: Medicago truncatula

<400> SEQUENCE: 13

```
atggaattat cttgggaaac aaaatcagcc ataattctca tcactgtgac atttggtttg      60
gtatacgcat ggagggtatt gaattggatg tggctgaagc caaagaagat agagaagctt    120
ttaagagaac aaggccttca agggaaccct tatagacttt tgcttggaga tgcaaaggat    180
tattttgtga tgcaaaagaa agttcaatcc aaacccatga atctatctga tgatattgcg    240
ccacgtgtcg ctccttacat tcatcatgct gttcaaactc atgggaaaaa gtcttttatt    300
tggtttggaa tgaaaccatg ggtgattctc aatgaacctg aacaaataag agaagtattc    360
aacaagatgt ctgagttccc aaaggttcaa tataagttta tgaagttaat aactcgcgt    420
cttgttaaac tagaaggaga aaagtggagc aagcatagaa gaataatcaa ccctgcgttt    480
cacatggaaa aattgaagat tatgacacca acattcttga aaagctgcaa tgatttgatt    540
agcaattggg aaaaaatgtt gtcttcaaat ggatcatgtg aaatggacgt atggccttcc    600
cttcagagct tgacaagtga tgttatcgct cgttcgtcat ttggaagtag ttatgaagaa    660
ggaagaaaag tatttcaact tcaaatagag caaggtgaac ttataatgaa aaatctaatg    720
aaatctttaa tcccttatg gaggttttta cctaccgctg atcatagaaa gataaatgaa    780
aatgaaaaac aaatagaaac tactcttaag aatataatta caagaggga aaaagcaatt    840
aaggcaggtg aagccactga gaatgactta ttaggtctcc tcctagagtc gaaccacaga    900
gaaattaaag aacatggaaa cgtcaagaat atgggattga gtcttgaaga gtagtcggg    960
gaatgcaggt tattccatgt tgcagggcaa gagactactt cagatttgct tgtttggacg   1020
atggtgttgt tgagtaggta ccctgattgg caagaacgtg caaggaagga agtattagag   1080
atatttggca atgaaaaacc cgactttgat ggactaaata aacttaagat tatggccatg   1140
attttgtatg aggttttgag gttgtaccct cctgtaaccg gcgttgctcg aaaagttgag   1200
aatgatataa aacttggaga cttgacatta tatgctggaa tggaggttta catgccaatt   1260
gttttgattc accatgattg tgaactatgg ggtgatgatg ctaagatttt caatcctgag   1320
agattttctg gtggaatttc caaagcaaca aacggtagat tttcatattt tccgtttgga   1380
gcgggtccta gaatctgcat ggacaaaaac ttttccctgt tggaagcaaa gatggcaatg   1440
gcattgattt taaagaattt ttcatttgaa ctttctcaaa catatgctca tgctccatct   1500
gtggtgcttt ctgttcagcc acaacatggt gctcatgtta ttctacgcaa aatcaaaaca   1560
taa                                                                 1563
```

<210> SEQ ID NO 14
<211> LENGTH: 520
<212> TYPE: PRT
<213> ORGANISM: Medicago truncatula

<400> SEQUENCE: 14

Met Glu Leu Ser Trp Glu Thr Lys Ser Ala Ile Ile Leu Ile Thr Val
1               5                   10                  15

Thr Phe Gly Leu Val Tyr Ala Trp Arg Val Leu Asn Trp Met Trp Leu
            20                  25                  30

```
Lys Pro Lys Ile Glu Lys Leu Arg Glu Gln Gly Leu Gln Gly
        35                  40                  45

Asn Pro Tyr Arg Leu Leu Leu Gly Asp Ala Lys Asp Tyr Phe Val Met
 50                  55                  60

Gln Lys Lys Val Gln Ser Lys Pro Met Asn Leu Ser Asp Asp Ile Ala
 65                  70                  75                  80

Pro Arg Val Ala Pro Tyr Ile His His Ala Val Gln Thr His Gly Lys
                 85                  90                  95

Lys Ser Phe Ile Trp Phe Gly Met Lys Pro Trp Val Ile Leu Asn Glu
                100                 105                 110

Pro Glu Gln Ile Arg Glu Val Phe Asn Lys Met Ser Glu Phe Pro Lys
                115                 120                 125

Val Gln Tyr Lys Phe Met Lys Leu Ile Thr Arg Gly Leu Val Lys Leu
    130                 135                 140

Glu Gly Glu Lys Trp Ser Lys His Arg Arg Ile Ile Asn Pro Ala Phe
145                 150                 155                 160

His Met Glu Lys Leu Lys Ile Met Thr Pro Thr Phe Leu Lys Ser Cys
                165                 170                 175

Asn Asp Leu Ile Ser Asn Trp Glu Lys Met Leu Ser Ser Asn Gly Ser
                180                 185                 190

Cys Glu Met Asp Val Trp Pro Ser Leu Gln Ser Leu Thr Ser Asp Val
            195                 200                 205

Ile Ala Arg Ser Ser Phe Gly Ser Ser Tyr Glu Glu Gly Arg Lys Val
        210                 215                 220

Phe Gln Leu Gln Ile Glu Gln Gly Glu Leu Ile Met Lys Asn Leu Met
225                 230                 235                 240

Lys Ser Leu Ile Pro Leu Trp Arg Phe Leu Pro Thr Ala Asp His Arg
                245                 250                 255

Lys Ile Asn Glu Asn Glu Lys Gln Ile Glu Thr Thr Leu Lys Asn Ile
                260                 265                 270

Ile Asn Lys Arg Glu Lys Ala Ile Lys Ala Gly Glu Ala Thr Glu Asn
            275                 280                 285

Asp Leu Leu Gly Leu Leu Leu Glu Ser Asn His Arg Glu Ile Lys Glu
290                 295                 300

His Gly Asn Val Lys Asn Met Gly Leu Ser Leu Glu Glu Val Val Gly
305                 310                 315                 320

Glu Cys Arg Leu Phe His Val Ala Gly Gln Glu Thr Thr Ser Asp Leu
                325                 330                 335

Leu Val Trp Thr Met Val Leu Leu Ser Arg Tyr Pro Asp Trp Gln Glu
            340                 345                 350

Arg Ala Arg Lys Glu Val Leu Glu Ile Phe Gly Asn Glu Lys Pro Asp
            355                 360                 365

Phe Asp Gly Leu Asn Lys Leu Lys Ile Met Ala Met Ile Leu Tyr Glu
    370                 375                 380

Val Leu Arg Leu Tyr Pro Pro Val Thr Gly Val Ala Arg Lys Val Glu
385                 390                 395                 400

Asn Asp Ile Lys Leu Gly Asp Leu Thr Leu Tyr Ala Gly Met Glu Val
                405                 410                 415

Tyr Met Pro Ile Val Leu Ile His His Asp Cys Glu Leu Trp Gly Asp
            420                 425                 430

Asp Ala Lys Ile Phe Asn Pro Glu Arg Phe Ser Gly Gly Ile Ser Lys
            435                 440                 445

Ala Thr Asn Gly Arg Phe Ser Tyr Phe Pro Phe Gly Ala Gly Pro Arg
```

```
                450             455             460
Ile Cys Ile Gly Gln Asn Phe Ser Leu Leu Glu Ala Lys Met Ala Met
465                 470                 475                 480

Ala Leu Ile Leu Lys Asn Phe Ser Phe Glu Leu Ser Gln Thr Tyr Ala
                485                 490                 495

His Ala Pro Ser Val Val Leu Ser Val Gln Pro Gln His Gly Ala His
            500                 505                 510

Val Ile Leu Arg Lys Ile Lys Thr
            515                 520

<210> SEQ ID NO 15
<211> LENGTH: 1551
<212> TYPE: DNA
<213> ORGANISM: Avena strigosa

<400> SEQUENCE: 15
atggagccgg cgcccttgag ctcatcgccg gtgcttatct gcctcctact cctactccta      60
cccatcgtcc tctattttgt gtaccggaaa ataatctga agaggaagca gcagcagcag     120
cagcagaatg ggccgcggga gctgcgggcg tacccgatcg tgggcacgct tccacacttc     180
atcaagaacg gcggcgcttc cctggagtgg tcgtcggccg tcatgcagcg cagcccgacg     240
cacaccatga tcctcaaggt gctgggcctg tcgggcaccg tgttcacggc gagcccggcc     300
agcgtggaac acgtgctgaa acgcgcttc gcgaactacc cgaaaggcgg tctggtcgat     360
atccagaccg acttccttgg gcacggcatc ttcaactcgg acggcgagga gtggcagcag     420
cagcgcaaga tggccagcta cgagttcaac cagcggtcgc tcaggagctt cgtggtgcac     480
gccgtccgtt cgaggtggt ggagcgcctg ctgccgctgc tggagcgggc cgccggggct     540
ggagcggccg tcgacctgca ggacgtgctg agcgcttcg ccttcgacaa catctgccgc     600
gtggctttcg ccaggacccc ggcatgcctc acggaggaga gcatgggcgc gaggcagagc     660
gtggagttga tgcacgcctt cgatgtggca agcaccatcg tcattaccag gttcgtgtct     720
ccgacgtggt tgtggcgcct gatgaagctg ctcaacgtgg ggccggagcg gcggatgcgg     780
aaggcactgg catccatcca cggctacgcc gacaacatca tccgggagag gaagaagaag     840
aagaagacat cagggaagga cgacgacctc ctgtcgcgct tcgccgattc cggcgagcac     900
agcgacgaga gcctccgcta cgtgatcacc aacttcatac tcgccggccg cgactccagc     960
tccgccgcgc tcacatggtt tttctggctc gtctccacca ggcccgaggt acaggacagg    1020
atctccaagg gatccgagc ggcgcgccag gcaagcgcaa cgacgacggg gcccttcggc    1080
ctggaggagc tgcgcgagat gcactacatc cacgccgcca tcacggagtc catgcggctc    1140
tacccgccgg tgcccatcaa cgcgcgcacc tccaccgagg acgatgtcct tccagacggc    1200
accgtggtcg ggaaaggctg gcgggtgatc tactccgcct acgccatggg gcggatggag    1260
gacgcctggg gaaaggacgg ggacgagttc cggccggaga ggtggctgga cgcggagaca    1320
ggggtgttca ggccggaggc accctgcaag tacccggtgt tccacgtcgg cccaagaatg    1380
tgcctcggca agagatggc ctacatacag atgaagtcca tcgtggcgtc cgtgtttgag    1440
aggttcagct tgcgctacct cggcggggac gcccatcccg gcctccagct cgctggaact    1500
ctgcgcatgg aaggcggctt gccgatgcac ctagaaatca gtactaacta g           1551

<210> SEQ ID NO 16
<211> LENGTH: 516
<212> TYPE: PRT
<213> ORGANISM: Avena strigosa
```

-continued

```
<400> SEQUENCE: 16

Met Glu Pro Ala Pro Leu Ser Ser Pro Val Leu Ile Cys Leu Leu
1               5                   10                  15

Leu Leu Leu Leu Pro Ile Val Leu Tyr Phe Val Tyr Arg Lys Asn Asn
            20                  25                  30

Leu Lys Arg Lys Gln Gln Gln Gln Gln Asn Gly Pro Arg Glu Leu
        35                  40                  45

Arg Ala Tyr Pro Ile Val Gly Thr Leu Pro His Phe Ile Lys Asn Gly
    50                  55                  60

Arg Arg Phe Leu Glu Trp Ser Ser Ala Val Met Gln Arg Ser Pro Thr
65              70                  75                  80

His Thr Met Ile Leu Lys Val Leu Gly Leu Ser Gly Thr Val Phe Thr
                85                  90                  95

Ala Ser Pro Ala Ser Val Glu His Val Leu Lys Thr Arg Phe Ala Asn
            100                 105                 110

Tyr Pro Lys Gly Gly Leu Val Asp Ile Gln Thr Asp Phe Leu Gly His
        115                 120                 125

Gly Ile Phe Asn Ser Asp Gly Glu Glu Trp Gln Gln Gln Arg Lys Met
130                 135                 140

Ala Ser Tyr Glu Phe Asn Gln Arg Ser Leu Arg Ser Phe Val Val His
145                 150                 155                 160

Ala Val Arg Phe Glu Val Val Glu Arg Leu Leu Pro Leu Leu Glu Arg
                165                 170                 175

Ala Ala Gly Ala Gly Ala Ala Val Asp Leu Gln Asp Val Leu Glu Arg
            180                 185                 190

Phe Ala Phe Asp Asn Ile Cys Arg Val Ala Phe Gly Gln Asp Pro Ala
        195                 200                 205

Cys Leu Thr Glu Glu Ser Met Gly Ala Arg Gln Ser Val Glu Leu Met
210                 215                 220

His Ala Phe Asp Val Ala Ser Thr Ile Val Ile Thr Arg Phe Val Ser
225                 230                 235                 240

Pro Thr Trp Leu Trp Arg Leu Met Lys Leu Leu Asn Val Gly Pro Glu
                245                 250                 255

Arg Arg Met Arg Lys Ala Leu Ala Ser Ile His Gly Tyr Ala Asp Asn
            260                 265                 270

Ile Ile Arg Glu Arg Lys Lys Lys Lys Thr Ser Gly Lys Asp Asp
        275                 280                 285

Asp Leu Leu Ser Arg Phe Ala Asp Ser Gly Glu His Ser Asp Glu Ser
    290                 295                 300

Leu Arg Tyr Val Ile Thr Asn Phe Ile Leu Ala Gly Arg Asp Ser Ser
305                 310                 315                 320

Ser Ala Ala Leu Thr Trp Phe Phe Trp Leu Val Ser Thr Arg Pro Glu
                325                 330                 335

Val Gln Asp Arg Ile Ser Lys Glu Ile Arg Ala Ala Arg Gln Ala Ser
            340                 345                 350

Ala Thr Thr Thr Gly Pro Phe Gly Leu Glu Glu Leu Arg Glu Met His
        355                 360                 365

Tyr Ile His Ala Ala Ile Thr Glu Ser Met Arg Leu Tyr Pro Pro Val
    370                 375                 380

Pro Ile Asn Ala Arg Thr Ser Thr Glu Asp Asp Val Leu Pro Asp Gly
385                 390                 395                 400

Thr Val Val Gly Lys Gly Trp Arg Val Ile Tyr Ser Ala Tyr Ala Met
```

```
              405                 410                 415
Gly Arg Met Glu Asp Ala Trp Gly Lys Asp Gly Asp Glu Phe Arg Pro
            420                 425                 430

Glu Arg Trp Leu Asp Ala Glu Thr Gly Val Phe Arg Pro Glu Ala Pro
        435                 440                 445

Cys Lys Tyr Pro Val Phe His Val Gly Pro Arg Met Cys Leu Gly Lys
    450                 455                 460

Glu Met Ala Tyr Ile Gln Met Lys Ser Ile Val Ala Ser Val Phe Glu
465                 470                 475                 480

Arg Phe Ser Leu Arg Tyr Leu Gly Gly Asp Ala His Pro Gly Leu Gln
                485                 490                 495

Leu Ala Gly Thr Leu Arg Met Glu Gly Gly Leu Pro Met His Leu Glu
            500                 505                 510

Ile Ser Thr Asn
        515

<210> SEQ ID NO 17
<211> LENGTH: 1440
<212> TYPE: DNA
<213> ORGANISM: Medicago truncatula

<400> SEQUENCE: 17
```

| | | | | | |
|---|---|---|---|---|---|
| atggagccta | atttctatct | ctcccttctc | cttctctttg | tcactttcat | atctctctct | 60 |
| cttttttca | tattctacaa | acagaaatct | ccattaaatt | tgccacctgg | taaaatgggt | 120 |
| tacccaatca | taggtgaaag | ccttgagttc | ttatcaacag | gatggaaagg | acatcctgaa | 180 |
| aaattcattt | tcgaccgtat | gcgtaaatat | tcctcagaac | tctttaaaac | atcaatcgta | 240 |
| ggagaatcta | cggtggtttg | ttgcggagca | gcaagtaaca | agtttttgtt | ttcaaacgag | 300 |
| aataaacttg | tgactgcatg | gtggccagat | agtgtaaaca | aaatcttccc | tactacttct | 360 |
| cttgactcta | acttgaagga | agaatccatc | aagatgagaa | aattgcttcc | acaattcttt | 420 |
| aaacccgaag | ctctacaacg | ttatgttggt | gtcatggatg | ttattgctca | aagacatttt | 480 |
| gttactcatt | gggataataa | aaatgaaatc | accgtctacc | ccttggccaa | gaggtacacc | 540 |
| ttttttgttag | cttgtcggtt | gttcatgagc | gttgaagacg | agaatcatgt | agcaaaattt | 600 |
| agtgatccat | tcagttaat | tgcggccgga | atcatatctc | taccaattga | tttgccagga | 660 |
| acaccattca | caaagctat | aaaggcctca | aactttataa | gaaaggagtt | gattaagatc | 720 |
| ataaagcaaa | ggagggtaga | tttggcagaa | gggacagcat | caccaacaca | agatatattg | 780 |
| tctcacatgt | tgttgacaag | tgatgaaaat | ggaaagagta | tgaatgaact | taatattgct | 840 |
| gataagattc | ttggccttt | gatcggagga | catgacactg | ctagcgtcgc | atgcactttc | 900 |
| cttgtcaaat | atctcggcga | gttacctcac | atttatgata | aagtctatca | agagcaaatg | 960 |
| gaaattgcaa | aatcgaaacc | agcaggagaa | ttgttgaatt | gggatgaccct | gaagaaaatg | 1020 |
| aaatactctt | ggaacgtagc | ttgtgaagta | atgagacttt | cccctccact | ccaaggaggt | 1080 |
| ttcagggaag | ccatcactga | ctttatgttc | aatggattct | caattcctaa | gggatggaag | 1140 |
| ctttattgga | gtgcaaattc | aacacataag | aacgcagaat | gttttcccat | gccagagaaa | 1200 |
| tttgacccca | aagatttga | aggaaatgga | ccagctcctt | atacttttgt | tcccttggt | 1260 |
| ggaggaccaa | ggatgtgtcc | tggaaaagag | tatgcaagat | agaaatact | tgttttcatg | 1320 |
| cacaatttgg | tgaaaaggtt | taagtgggaa | aaggtgattc | cagatgagaa | gattattgtt | 1380 |
| gatccattcc | ccatccctgc | aaaggatctt | ccaattcgcc | tttatccaca | caaagcttaa | 1440 |

```
<210> SEQ ID NO 18
<211> LENGTH: 479
<212> TYPE: PRT
<213> ORGANISM: Medicago trunatula

<400> SEQUENCE: 18

Met Glu Pro Asn Phe Tyr Leu Ser Leu Leu Leu Phe Val Thr Phe
1               5                   10                  15

Ile Ser Leu Ser Leu Phe Phe Ile Phe Tyr Lys Gln Lys Ser Pro Leu
            20                  25                  30

Asn Leu Pro Pro Gly Lys Met Gly Tyr Pro Ile Ile Gly Glu Ser Leu
            35                  40                  45

Glu Phe Leu Ser Thr Gly Trp Lys Gly His Pro Glu Lys Phe Ile Phe
    50                  55                  60

Asp Arg Met Arg Lys Tyr Ser Ser Glu Leu Phe Lys Thr Ser Ile Val
65                  70                  75                  80

Gly Glu Ser Thr Val Val Cys Cys Gly Ala Ala Ser Asn Lys Phe Leu
                85                  90                  95

Phe Ser Asn Glu Asn Lys Leu Val Thr Ala Trp Trp Pro Asp Ser Val
            100                 105                 110

Asn Lys Ile Phe Pro Thr Thr Ser Leu Asp Ser Asn Leu Lys Glu Glu
            115                 120                 125

Ser Ile Lys Met Arg Lys Leu Leu Pro Gln Phe Phe Lys Pro Glu Ala
    130                 135                 140

Leu Gln Arg Tyr Val Gly Val Met Asp Val Ile Ala Gln Arg His Phe
145                 150                 155                 160

Val Thr His Trp Asp Asn Lys Asn Glu Ile Thr Val Tyr Pro Leu Ala
                165                 170                 175

Lys Arg Tyr Thr Phe Leu Leu Ala Cys Arg Leu Phe Met Ser Val Glu
            180                 185                 190

Asp Glu Asn His Val Ala Lys Phe Ser Asp Pro Phe Gln Leu Ile Ala
        195                 200                 205

Ala Gly Ile Ile Ser Leu Pro Ile Asp Leu Pro Gly Thr Pro Phe Asn
    210                 215                 220

Lys Ala Ile Lys Ala Ser Asn Phe Ile Arg Lys Glu Leu Ile Lys Ile
225                 230                 235                 240

Ile Lys Gln Arg Arg Val Asp Leu Ala Glu Gly Thr Ala Ser Pro Thr
                245                 250                 255

Gln Asp Ile Leu Ser His Met Leu Leu Thr Ser Asp Glu Asn Gly Lys
            260                 265                 270

Ser Met Asn Glu Leu Asn Ile Ala Asp Lys Ile Leu Gly Leu Leu Ile
        275                 280                 285

Gly Gly His Asp Thr Ala Ser Val Ala Cys Thr Phe Leu Val Lys Tyr
    290                 295                 300

Leu Gly Glu Leu Pro His Ile Tyr Asp Lys Val Tyr Gln Glu Gln Met
305                 310                 315                 320

Glu Ile Ala Lys Ser Lys Pro Ala Gly Glu Leu Leu Asn Trp Asp Asp
                325                 330                 335

Leu Lys Lys Met Lys Tyr Ser Trp Asn Val Ala Cys Glu Val Met Arg
            340                 345                 350

Leu Ser Pro Pro Leu Gln Gly Gly Phe Arg Glu Ala Ile Thr Asp Phe
        355                 360                 365

Met Phe Asn Gly Phe Ser Ile Pro Lys Gly Trp Lys Leu Tyr Trp Ser
    370                 375                 380
```

```
Ala Asn Ser Thr His Lys Asn Ala Glu Cys Phe Pro Met Pro Glu Lys
385                 390                 395                 400

Phe Asp Pro Thr Arg Phe Glu Gly Asn Gly Pro Ala Pro Tyr Thr Phe
            405                 410                 415

Val Pro Phe Gly Gly Pro Arg Met Cys Pro Gly Lys Glu Tyr Ala
        420                 425                 430

Arg Leu Glu Ile Leu Val Phe Met His Asn Leu Val Lys Arg Phe Lys
        435                 440                 445

Trp Glu Lys Val Ile Pro Asp Glu Lys Ile Ile Val Asp Pro Phe Pro
        450                 455                 460

Ile Pro Ala Lys Asp Leu Pro Ile Arg Leu Tyr Pro His Lys Ala
465                 470                 475
```

<210> SEQ ID NO 19
<211> LENGTH: 1443
<212> TYPE: DNA
<213> ORGANISM: Vitis vinifera

<400> SEQUENCE: 19

```
atggaggtgt tcttcctctc cctgctcctc atctttgtgc tctcagtctc catcggactt      60
cacttgctct tctacaagca tagatcccac ttcactggcc ccaatctccc tcctggcaag     120
attggttggc ctatggttgg tgaaagcctt gaattcctct ccaccggctg aaaggccac     180
ccggaaaaat tcatcttcga tcgcatctcc aaatactcct ctgaagtctt caagacctcc     240
ctcctcggag agcctgctgc cgtctttgct ggcgctgcgg gcaacaagtt tttgttctcc     300
aacgaaaaca aacttgttca tgcgtggtgg cctagctctg tcgacaaggt cttccctcc     360
tccacccaaa cctcatccaa agaggaggcc aagaagatga ggaagttgct ccctcagttc     420
tttaagcctg aagccttgca acgttacatt ggcatcatgg atcacattgc gcagaggcat     480
tttgctgata gctgggacaa cagagatgaa gtcattgtat tccactggc aagaggttc     540
actttctggc tagcttgccg cctgtttatg agcatagaag atcctgccca cgtcgctaaa     600
tttgaaaagc ccttccatgt cttggcctca ggactcatca ccgtcccaat tgacttgcct     660
gggacacctt tccaccgcgc tatcaaggcc tccaacttca tcagaaagga gcttagagcc     720
atcatcaagc aaaggaagat cgatctggct gagggcaagg cctcacaaaa tcaagatata     780
ttgtcccaca tgcttctggc tacagatgaa gatggatgcc acatgaatga aatggaaatt     840
gctgataaaa tcctcggttt gttgattggt ggccatgaca ctgccagtgc tgccattaca     900
ttccttatca agtacatggc tgagctgcct cacatctacg agaaagtcta cgaggagcaa     960
atggaaattg ccaattcaaa agcaccaggt gaattgctga actgggatga tgttcaaaac    1020
atgagatatt catggaatgt tgcctgtgaa gtgatgagac ttgcacccc actccaagga    1080
gctttccggg aagcaatcac tgacttcgtg ttcaacggtt tctccattcc taagggttgg    1140
aagctgtact ggagcgcaaa ctcaacccac aaaagcccag aatgcttccc tcaacccgaa    1200
aattttgacc ctacaagatt tgaaggaaac gggcctgctc cttacacatt cgttcccttt    1260
ggtggcggac ctaggatgtg ccctggtaaa gagtacgccc gcttggaaat actagtcttc    1320
atgcacaacg tggttaaaag gttcaaatgg gataaattgc ttcctgatga agataatc    1380
gttgacccca tgcccatgcc tgctaaggga cttccagttc gcctccatcc tcacaaacca    1440
tag                                                                 1443
```

<210> SEQ ID NO 20

<211> LENGTH: 1443
<212> TYPE: DNA
<213> ORGANISM: Vitis vinifera

<400> SEQUENCE: 20

| | | | | |
|---|---|---|---|---|
| atggaggtgt | tcttcctctc | cctgctcctc | atctctgtgc | tctcagtctc catcagactt | 60 |
| tacttgctct | tatacaagca | tagatcccac | ttcactggcc | ccaatctccc tcctggcaag | 120 |
| attggttggc | caatggttgg | tgaaagcctt | gaattcctct | ccaccggctg aaaggccac | 180 |
| ccggaaaaat | tcatcttcga | tcgcatctcc | aaatactcct | ctgaagtctt caagacctcc | 240 |
| ctcctcggag | agcctgctgc | cgtctttgct | ggcgctgcgg | gcaacaagtt tttgttctcc | 300 |
| aacgaaaaca | aacttgttca | tgcatggtgg | cctagctccg | tcgacaaggt cttcccctcc | 360 |
| tccacccaaa | cctcatccaa | agaggaggcc | aagaagatga | ggaagttgct ccctcagttc | 420 |
| cttaagcctg | aagccttgca | acgttacacc | ggcatcatgg | atcacattgc acagaggcat | 480 |
| tttgctgata | gctgggacaa | cagagatgaa | gtcattgtat | tccactggc caagaggttc | 540 |
| actttctggc | tagcttgccg | cctgtttatg | agcatagaag | atcctgccca cgtcgctaaa | 600 |
| tttgaaaagc | ccttccacgt | cttggcctca | ggactcatca | ccatcccaat tgacctgcct | 660 |
| gggacaccct | tccaccgcgc | tatcaaggcc | tccaacttca | tcagaaagga gcttagagcc | 720 |
| atcatcaagc | aaaggaagat | cgatctggct | gagagcaagg | cctcaaaaac tcaagatata | 780 |
| ttgtcccaca | tgcttctggc | tacagatgaa | gatggatgcc | acatgaatga atgagtatt | 840 |
| gctgataaaa | tcctcggttt | gttgattggt | ggccatgaca | ctgccagttc tgccattaca | 900 |
| ttccttgtca | gtacatggc | tgagctgcct | cacatctacg | agaaagtcta caaggagcaa | 960 |
| atggaaattg | ccaattcaaa | agcaccaggt | gaattgctga | actgggatga tgttcaaaag | 1020 |
| atgagatatt | catggaatgt | tgcctgtgaa | gtgatgagac | ttgcaccccc actccaagga | 1080 |
| gctttccggg | aagcaatcac | tgacttcgtg | ttcaacggtt | tctccattcc taagggttgg | 1140 |
| aagctgtact | ggagcgcaaa | ctcaacccac | aaaagcctag | aatgcttccc tcaacccgaa | 1200 |
| aaatttgacc | ctacaagatt | tgaaggagcc | gggcctgctc | cttacacatt cgttcccttt | 1260 |
| ggtggcggac | ctaggatgtg | ccctggtaaa | gagtacgccc | gcttggagat acttatcttc | 1320 |
| atgcacaact | tggttaaaag | gttcaaatgg | gataaattgc | ttcctgatga agataatc | 1380 |
| gttgaccca | tgcccatgcc | tgctaaggga | cttccagttc | gcctccatcc tcacaaacca | 1440 |
| tag | | | | | 1443 |

<210> SEQ ID NO 21
<211> LENGTH: 1779
<212> TYPE: DNA
<213> ORGANISM: Panax ginseng

<400> SEQUENCE: 21

| | | | | |
|---|---|---|---|---|
| ttatcttcag | tcccaaaaat | caaacatttc | ttgtatttgt | ccctaacta cctagaaagc | 60 |
| aaaagggcgc | catcaagaaa | tggaactctt | ctatgtccct | ctcctctcac tcttgttct | 120 |
| cttcatctct | ttatcattcc | acttcctctt | ctacaagtcc | aaacccagct cctccggcgg | 180 |
| gtttcctctc | ccgccgggca | agactggtg | gcccattatt | ggagagagct acgagtttct | 240 |
| ctccacggga | tggaaaggct | acccggagaa | gttcatattt | gaccgtatga ccaagtactc | 300 |
| ctcaaatgtc | tttaaaacct | ctattttcgg | agagcccgcc | gcagtattct gcggcgcggc | 360 |
| ttgtaacaag | ttcttgttct | cgaacgagaa | taagcttgtt | caggcctggt ggcctgactc | 420 |
| cgtgaacaaa | gtttttcctt | catcaaccca | aacctcttcg | aaagaagagg cgattaagat | 480 |

```
gcgaaaaatg ctgccaaact tctttaaacc ggaggctttg cagcgctaca tcggcctcat      540
ggaccaaatc gctgcaaatc actttgaatc cggttgggaa aataaaaacg aagtggttgt      600
atttcccctg gcaaaatcct acacgttttg gatcgcgtgt aaggtatttg ttagcgtaga      660
ggaacctgcg caggttgcgg agctgttgga accattcagc gcgattgctt ctgggattat      720
atccgtccca atagatttgc ccggcacgcc gtttaacagt gccataaaat catcgaaaat      780
tgttaggagg aagcttgtgg ggattattaa gcagaggaaa attgatttag gggagggaaa      840
ggcttcagca acacaagaca tattgtcaca catgctgttg acaagtgatg aaagtggcaa      900
gtttatgggt gaggggggata ttgccgataa gatattgggg ttgttgattg gaggccatga      960
cactgcaagt tctgcatgta cttttgttgt caagtttctt gctgagctgc ctcagattta     1020
tgagggagtc taccaggagc aaatggagat agtgaaatct aaaaaggcag agaattatt      1080 gaagtgggag gacatacaaa agatgaaata ttcgtggaat gtagcctgtg aagtgctgag     1140
acttgcacca cctcttcaag gagcttttag agaagccctc tccgatttca cctacaacgg     1200
tttctcaatc cctaaaggct ggaagctata ttggagtgca aattcaaccc acataaactc     1260
agaagttttc ccggagccac taaaatttga tccatcaaga ttcgacggag ccgggccgcc     1320
gccgttctcg ttcgtgccgt tcggcggcgg gccgagaatg tgccccggaa aagagtatgc     1380
ccggctggaa atactggtgt ttatgcacca tcttgtcaag aggttcaagt gggaaaaggt     1440
tattcctgat gagaaaattg ttgttaatcc catgccaatt cctgccaacg gacttcctgt     1500
tcgcctattt ccacacaaag cctaagatta tgacttaatt aaatgtttaa tttcaaacta     1560
ttttaattaa tttacttata ctttatgtat aaacgttgaa ctagtaattg cttggccaat     1620
ttgttagata ctactactat gcggtaataa tgacaattac taaagattat gttactgttt     1680
gactcacttg agatcatttt catccctagt tagatctcgt attggacggt gagagatgtc     1740
tttgttaaaa tagtattcat agtaactatt tgctatgta                           1779
```

<210> SEQ ID NO 22
<211> LENGTH: 1671
<212> TYPE: DNA
<213> ORGANISM: Maesa lanceolata

<400> SEQUENCE: 22

```
atggagcttc tgttcgtctc tctcctctct ctcttcctcc tcatcctcct ccctctctct       60
ctcctcttcc tcttcccctc ttccttctcc accaccacca ccgaggccaa taaaaactcc      120
gccaacctcc ccccgggtct cacggggtgg ccggtcgttg cgagagcttc cagtttctc       180 gccgcggggt ggcgcggcaa cccggagaaa ttcatattcg accgcatcgc caagtactct      240
tcgtacgtgt ataagacgaa cttgatgctg agcgcaccg cagtgttctg cggggctcca       300
gcgcacaagt ttttgttctc gaatgagaac aagctggtgc agtcgtggtg ccaagctcg       360 gtgaacaaga tcttcccgtc gtcgaaccag acgtcgtcga aggaggaggc gatgaagatg      420
aggaagatgc tgccgaactt cttcaaaccg gaggcattgc aggggtatat cgggatcatg      480
gataccatcg cgcagcgcca tttcgccgcc gactgggaca ataaggatta catcgtagtt      540
ttcccactat gcaagcgcta cacatttggg ttggcctgta aaatattcat gagcatagaa      600
gatcctaaag atgtggatag attccttgcc cgttttaatc tcgtggcgga gggattgtta      660
tccattccaa tcgatttgcc gggaaccccg ttccaccact ctattaaggc agcggagttc      720
atcagggaac accttgttgc aattattaag caaagaaaga tcgacctggc tgaaggaaag      780
```

| | |
|---|---|
| gcgtcgccga cccaagatat aatgtcgtat atgcttctaa cacccgacga ggatggaaag | 840 |
| tttatgaagg agtatgacat cgcggacaag attttgggat tacttgtcgg tggccatgac | 900 |
| accgcaagct ctgcttgcgc ttttattgtc aagtatttgg cggagctgcc ccaggtctac | 960 |
| caaggagttt ataaggagca aatggagatt gccaagtcca aagggccagg tgaattattg | 1020 |
| aattgggatg acattcagaa gatgaagtat tcatggaacg tagcatgtga agtgttgaga | 1080 |
| cttgcaccac cactccaggg tgctttcaga gatgtgttga agatttcat gtatgaaggc | 1140 |
| ttctacattc caaagggttg aaggtgtat tggagtgctc attcgacgca caaaaatcct | 1200 |
| gaatacttcc cagaaccata taagtttgac ccatcaagat ttgatggatc tggaccagct | 1260 |
| ccttacacat ttgtaccatt cggcggaggg ccaaggatgt gtcctgggaa agagtatgca | 1320 |
| agattggaaa tactcgtctt catgcataat cttgtgaaga ggtttcgatg gaaaaattg | 1380 |
| atccccgatg aaaaaattgt tgtcaatccc atgcccgtcc cagagaaggg tcttccgatc | 1440 |
| cgactcttct catatgatgc ttagattttg tttcgatttc tgttgttttt ccttgttttcc | 1500 |
| cttttaatt ctcattcagt ggccatgccc tgtcttggag aagctagttg tctctaaatc | 1560 |
| ttggtcgact tctttaggta cataaagttg tacgttaaat cgggaaataa cttcaaaaga | 1620 |
| atggttcttt tgttcactgc atcaaaaaaa aaaaaaaaa aaaaaaaaa a | 1671 |

<210> SEQ ID NO 23
<211> LENGTH: 1452
<212> TYPE: DNA
<213> ORGANISM: Chenopodium album

<400> SEQUENCE: 23

| | |
|---|---|
| atggagctct tcttcttggc tagcatagcc cttatttcct ccttatctct accttttctc | 60 |
| tatctattct ataggcatta ttcgacctgg gggtacaagc tacccccagg atcgatggga | 120 |
| tggcccgtgg tgggcgaatc cctagagttt ttctctaccg gttggaaggg atacccggag | 180 |
| aagttcatct ttgatagact taaaaagtac aaacctagcc aagtgttcaa gacttccatc | 240 |
| tttggtgaaa aggttgcaat tttatgtggc gcgacaggta acaaattctt gtactcgaac | 300 |
| gagaacaagt tagtacaagc ttggtggcct aaatcagttg acaagatctt tcctgctgcc | 360 |
| acccaacatt cctccataga agaagctagg actatgcgga agcttatccc tcttttcctt | 420 |
| aagcccgaat ctttacaaag gtacataccc atcatggaca ccatagccac caggcacatg | 480 |
| gagtccgggt gggagggcaa ggacaaggta gaagtgttcc cattagctaa gcgatacacc | 540 |
| ttttgggtgg cttgtaggct cttcttgagc attgaggacc cggtccatgt agccaagttc | 600 |
| gcggacccct tcaatgagat agccgcaggg atcatatcca tcccaataga tctcccaggg | 660 |
| acaccgttcc acaaagggat caaatcttct gaaatcgtaa ggaaagagtt gagtgcaatt | 720 |
| atcaagcaaa ggaaattaga cttagcagat ggcaaagctt cacctacaca agatattcta | 780 |
| tctcatatgt tgttaacttc tactgatgat gggaagttta tgaatgaaat ggatattgct | 840 |
| aataaaattt tgggacttct tattggtgga catgatactg ctagtgcttc ttgtacctttt | 900 |
| attgtcaagt ttcttgctga acttcctcac atctatgaag gtgtttacaa agagcaaatg | 960 |
| gagatagcaa attcaaaaaa accaggggag cttctaaatt gggaggacat acaaaagatg | 1020 |
| aaatactcat ggaatgtggc atgtgaagtg atgcgtttgg ctcctccact ccaaggtggt | 1080 |
| tttagagaag ccatttccga ctttatgtac aacgggttcc aaattcccaa gggctggaag | 1140 |
| ctatattgga gtgcaaatac aacacatttg aacccagaat ttttccctga accgacgaaa | 1200 |
| ttcgacccat cgaggttcga tgggtccggg ccagcaccat acacattcgt acccttttga | 1260 |

```
ggggggaccaa gaatgtgccc aggaaaagag tatgcaagac tagagatatt ggtgttcatg    1320
taccatattg tcaagaggtt taaatgggaa aaagtgcttc ctagtgagaa agttattgtt    1380
aatcccatgc ctattccgga gcacggcctt cccgtccgcc ttttcccaca tcctcaaacc    1440
acggttgctt aa                                                         1452

<210> SEQ ID NO 24
<211> LENGTH: 1452
<212> TYPE: DNA
<213> ORGANISM: Chenopodium quinoa

<400> SEQUENCE: 24
atggagctct tcttcttgtg tagcatagcc cttgttttct tcctatctct gccttttctc      60
tacctattct ataggcataa ttcgacccgg gggtacaagc taccccccagg gtcgatggga    120 tggcctgtgg tgggcgagtc cctagagttt ttctctaccg ggtggaaggg ataccccgag    180
aagttcatct ttgatagact aaagaagtac aaacctagcc aagtgttcaa gacttccatc    240
tttggagaac aagttgcgat tttatgtggc gcgacaggta acaagttctt gtactcgaac    300
gagaacaagt tagtacaagc ttggtggcct aaatcagttg ataagatctt tcctgctgcc    360
acccaacatt cctccataga agaagctagg actatgcgga agcttatccc tctcttcctt    420
aagcccgagt ctttacaaag gtacataccc atcatggaca ccatagccac ccggcacatg    480
gagtccgggt gggagggcaa ggacaaggta gaagtgttcc ccttagcaaa gcgatacacc    540 tttttgggtcg cttgtaggct cttcttgagc attgaggacc cggtccatgt agccaagttt    600
gccgacccct tcaatgagat agccgcaggg atcatatcca tcccaataga tctccccggg    660
acaccgttcc acaaagggat caagtcttcc gaaatcgtaa ggaaagagtt gagagcaatt    720
atcaagcaaa ggaaattaga ttttgcagat ggcaaagctt caccaacaca agatattcta    780
tctcatatgt tgttaacttc taccgaagat gggaagttta tgaatgagat ggatattgct    840
aataaaattt tgggacttct tattggtgga catgatactg ctagtgcttc ttgtaccttt    900
attgtcaagt tcttgctga gcttcctcac atctatgaag gtgtttacaa agagcaaatg    960
gagatagcaa attcaaaaaa accaggggag cttctaaatt gggaggacat acaaaagatg   1020
aaatactcat ggaatgtggc atgtgaagtg atgcgtttgg ctcctccact ccaaggtggt   1080
tttagagaag ccatttccga cttttatgtac aatggattcc aaattcccaa gggttggaag   1140
ctatattgga gtgcaaatac aacacatttg aacccagaat gcttcccaga gccacagaaa   1200
tttgacccat cgaggtttga tgggtcgggg ccagcaccat acacattcgt acccttgga    1260 ggggaccaa gaatgtgccc aggaaggag tatgcaaggc tagagatatt ggtgttcatg    1320
taccacattg tcaagaggtt taaatgggaa aaagtgcttc ctaatgagaa agttattgtt    1380
aatcccatgc ctattccgga gcatggcctt cccgtccgcc ttttcccaca tcctcaaacc    1440
gcagttgctt aa                                                         1452

<210> SEQ ID NO 25
<211> LENGTH: 1428
<212> TYPE: DNA
<213> ORGANISM: Barbarea vulgaris

<400> SEQUENCE: 25
atgtatttga caatcctatt cctcttcgtc agctccattc ttctttctct catgttcctc      60
ctaagaaaac atttatcaca cttctcctat caaaatcttc ctccgggaaa gactggcttt    120
```

```
cccttaatcg gagagagttt atccttcctc tctgaaggca gtcaaggcca tccggagaag      180
ttcatcactg accgagttcg tcggttcatc tcctcctcct caggtgtctt caagacccac      240
ctctttggat ctcccaccgc agtgatgacc ggtgcatccg gtaacaagtt tctattcacc      300
aatgagaaca agctcgtggt ctcgtggtgg ccagattccg tgaagaagat cttcccttat      360
acgcagtcga cctacacaga ggagtccaag aaactgagga tacttctttt gcagttcatg      420
aagcctgaag ctttgaggaa gtatataggt gttatggatg aggttactca gagacatttt      480
gagactgaat ggaccaataa aaaacagctc attgtctacc ctctctcaaa aaagttgacg      540
ttttcaatag catgccgttt atttctaagc atggacgacc ccgaaagagt aagcaaacta      600
gaagagcgat tcaattcggt agtgatgggg atctattcaa tccctataga cttgccagga      660
acacggttta accgatccat caaggcgtca agattaatca gaaaagaggt ttgcgcgatc      720
atcgggcaaa ggagagaaga gctaaaggcc gggagagcat ccgcggaaca agacgtccta      780
tctcacatgt tgacgagtgt aggagagacc aaagacgagg atttggctaa ctatttgatt      840
ggaatcttaa tcggaggaca tgacacagcg gctatcgcaa ccactttcat tatcagttat      900
cttgctgagt accctcatgt ctaccaacgt gttctacaag agcaaaagga gatactaaac      960
gaaaagaaag aaaaagaaag attaaagtgg gaggacattg agaaaatgaa atattcatgg     1020
aatgttgcat gtgaagtgat gagacttgtt cctcctctta ctggcacttt tcgtgaggcc     1080
atcgatcact tcacttttaa aggttttttac atccccaaag gatggaagtt atactggagt     1140
gccactgcaa cacatatgaa tccagactac ttccccgaac cagagagatt tgagccaaac     1200
cgatttgaag gaagtggtcc aaagccttat acatatattc catttggagg aggaccaagg     1260
atgtgtcccg ggagagagtt tgcccgtcta gagattcttg taattatcca caatcttgtt     1320
aatagattta gtgggaaaaa agtgtctcca aatgaaaata aaatagtggt agatcctttta     1380 ccaaaaccag gcaatggtct ccctattcga atttttcctc acttttga                 1428
```

<210> SEQ ID NO 26
<211> LENGTH: 1428
<212> TYPE: DNA
<213> ORGANISM: Barbarea vulgaris

<400> SEQUENCE: 26

```
atgtatttga caatcctatt cctcttcgtc agctccattc ttctttctct catgttcctc       60
ctaagaaaac atttatcaca cttctcctat caaaatcttc ctccgggaaa gactggcttc      120
cccttaatcg gagagagttt atccttcctc tctgagggcc gtcaaggccg tcccgagaag      180
ttcgtcactg accgagttcg tcggttcatc tcctcctcca caggtgtctt caagacccac      240
ctctttggat atcccaccgc agtgatgact ggtgcctccg gtaacaagtt tctattcacc      300
aatgagaaca agctcgtggt ctcgtggtgg ccagattccg tgaagaagat cttcccttat      360
acgcagtcga cctacacaga tgagtccaag aaactgagga tacttcttat gcagttcatg      420
aagcctgaag ctttgaggaa gtatataggt gttatggatg aggttgctca gagacatttt      480
gagactctat ggaccaatca aaaacagctt attgtctacc ctctctcaaa aaagttgacg      540
ttttcagtag catgccgttt atttctaagc atggacgacc ccgaaagagt aagcaaacta      600
gaagaccgat tcaattcggt agtgacaggg atctattcag tccctataga cttgccagga      660
acacggttta accgatccat caaggcgtca aggttactca gaaaagaggt ttgcgcgatc      720
atcgggcaaa ggagagaaga gctaaaggcc gggagagcat ccgcggaaca agacgtccta      780
tctcacatgt tgatgagtgt aggagagacc aaagacgagg atttggctaa ctatttgatt      840
```

```
ggaatcttaa tcggaggaca tgacacagcg gctatcgcaa ccactttcat tatcaattat    900
cttgctgagt accctcatgt ctaccaacgt gttctacaag agcaaaagga gatactaaag    960
gaaaagaaag aagaagaaag attaaagtgg gaggacattg agaaaatgaa atattcatgg   1020
aatgttgcat gtgaagtgat gagacttgtt cctcctctta ctggcaattt tcgtgaggcc   1080
atcgatcact tcacttttaa aggtttttac atccccaagg gatggaagtt atactggagt   1140
gccactgcaa cacatatgaa tccagactac ttccccgaac cagagagatt tgagccaaac   1200
cgattcgaag gaagtggtcc aaagccttat tcatatattc catttggagg aggaccaagg   1260
atgtgtcccg ggagagagtt tgcccgtcta gagattcttg taattatcca caatcttgtt   1320
aatagattta agtgggaaaa agtgtttcca aatgaaaata aaatagtggt agatccttta   1380
ccaaaaccag gcaatggtct ccctattcga atttttcctc acttttga                1428
```

<210> SEQ ID NO 27
<211> LENGTH: 1760
<212> TYPE: DNA
<213> ORGANISM: Malus domestica

<400> SEQUENCE: 27

```
cacttccatc aaacaaacaa actcaaggca cgttcctcgc ttcttaaaca acaacaaaat     60
ggagcacttc tatctgaccc tcctcttagg gtttgtctcc ttcatcactc tttctctctc    120
cgtgctcttt taccggcaca gagcgcagtt cgtcggcacc aacctgccgc ctggcaaagt    180
tggttaccca gtgatcggcg agacctacca gttcctagcc acaggatgga aaggtcaccc    240
ggagaaattc atcttcgacc gcatgaccaa gtactcctcc gaagtgttca agacctcact    300
catgggcgag aaggccgcca tcttctgcgg tgcagcctgc aacaagttct tgttctccaa    360
cgagaacaag ctcgtcactg catggtggcc cagctcagtc aacaaggtct tcccttcttc    420
tttggagact tctgccaagg aggaggccaa gaagatgaga aagatgcttc ccaacttcat    480
gaagcccgag gctctccagc gatacatcgg catcatggac accgtcgccc gacgccactt    540
cgctgagggc tgggaaaaca agaaggaagt tgaagtcttt cccctcgcca agaactatac    600
cttttggctt gctgcacggt tgtttgtgag cctggaggac tcggttgaga tcgccaagtt    660
aggcgacccg ttcgcagttt tggcctcggg aatcatatcg atgcctctgg atttcccggg    720
gactccgttt tacaaagcga tcaaggcgtc caacttcatc agggaggagc tgacgaagat    780
catcaagcag aggaagatag acttggcgga gggcaaagcg tcgccaacgc aagatatatt    840
gtctcacatg ttgttgttgt gcgacgagca cggaagtcac atgaaggaac acgatatcgc    900
ggataagatt ttggggctgc tgatcggtgg ccatgacact gctagcgcta cctgcacttt    960
tattgttaag tatcttgccg agcttcctca catttatgac gaagtctaca aggagcaaat   1020
ggaggtccta agcgcaaaag caccagggga cttgttgaac tgggatgacc tacagaagat   1080
gaaatactca tggaacgtag ctcaggaagt tctcagattg gctccacctc ttcaaggagc   1140
tttcagggaa gccttatctg actttgtctt caatggtttc accattccaa aaggctggaa   1200
gttgtattgg agtgcaaatt caacacacaa gaacgcagct tacttcccgg aaccattcaa   1260
attcgaccct acaagattcg aaggaaatgg tccagcacca tacacgtttg tgccctttgg   1320
aggaggtcct aggatgtgcc ccggcaaaga gtacgcccga ttggaaatcc tagtgttcat   1380
gcacaacttg gtgaagaggt tcaaatggga aaaagttctt cccgacgagc agatcgtagt   1440
tgacccactg cccatgcccg ccaagggact ccccgtccgc cttttccctc accctaagac   1500
```

| agccacaact taattatcta gctaagctta tacttaaaag taaaaaaaa aaaaaaaaaa | 1560 |
| cccatcaaac aaggctttat ttcttggtta ttgtattcgt tcttcatatt tgatctctgt | 1620 |
| acgcccatag ttttttttaa tgcaatcact tctactgtat taaaatctag acttgtacct | 1680 |
| ggccacttga tgttcatgtt tcaagacatg aaaattgtat aattgagaaa ttaagaataa | 1740 |
| acatggtata ttgtttacta | 1760 |

<210> SEQ ID NO 28
<211> LENGTH: 1443
<212> TYPE: DNA
<213> ORGANISM: Catharanthus roseus

<400> SEQUENCE: 28

| atggagatct tctatgtcac tctccttagc ttattcgttc tccttgtttc cctttccttt | 60 |
| catttcctct tctacaaaaa caaatcaacc ttgccgggac cgttacctcc gggccggacc | 120 |
| ggctggccga tggtgggaga agtcttcaa tttctctcag cgggctggaa aggccatcct | 180 |
| gaaaaattca tatttgatcg tatggctaag tattcttcga atgtctttag gtcacatcta | 240 |
| ctaggtgaac ctgccgcggt attttgtggt gcaattggaa ataaattttt attctcaaat | 300 |
| gaaaataaac ttgttcaagc atggtggcct gattcagtaa caaagttttt cccatcttca | 360 |
| aatcaaactt cttcaaaaga agaagctatt aaaatgcgaa agatgcttcc gaattttctt | 420 |
| aaaccggaag ctttacaacg ttacataggt ttaatggacc aaattgccca aaaacatttt | 480 |
| tcttccggtt gggaaaatag ggaacaagtt gaagtttttc ctttagccaa aaattatact | 540 |
| ttttggttag cttcaagatt atttgttagt gttgaagatc caattgaagt tgcaaaatta | 600 |
| cttgaaccct ttaatgtttt ggcctcggga ctaatttctg tccctattga tttgcctggt | 660 |
| acaccttta atcgtgctat aaaggcatca aatcaagtaa gaaaaatgct tatttctata | 720 |
| attaaacaaa gaaaaattga tttagctgaa ggaaaagcat ctccaacaca agatattttg | 780 |
| tcacatatgc ttttaacaag tgatgaaaat ggtaaattca tgcatgaatt ggatattgct | 840 |
| gataaaatcc ttggtttgtt aattggtgga catgatactg caagttctgc atgtactttt | 900 |
| attgtcaagt tccttggaga attgccagag atatatgaag gagtttataa agaacaaatg | 960 |
| gagattgcca actcaaaagc ccctggtgaa ttcttgaatt gggaagatat tcaaaagatg | 1020 |
| aaatattcat ggaatgtagc atgtgaagtg ttgagacttg caccacctct ccaaggtgct | 1080 |
| tttagagaag ccctaaatga tttcatgttc catggattct ctattccaaa aggatggaag | 1140 |
| atttactgga gtgtgaattc aacacacaga atccagaat gttttccaga tccacttaaa | 1200 |
| tttgacccgt caagatttga tggatctgga cctgctccat atacatttgt accatttggt | 1260 |
| ggaggaccaa gaatgtgccc tggaaaagaa tacgctaggc tggaaattct ggtttttatg | 1320 |
| cataatcttg tgaagagatt caagtgggaa aaaattatcc caaatgaaaa gattgttgtt | 1380 |
| gatccaatgc caattcctga aaaggactt cctgttcgac tttatcctca cattaatgca | 1440 |
| taa | 1443 |

<210> SEQ ID NO 29
<211> LENGTH: 1689
<212> TYPE: DNA
<213> ORGANISM: Avena strigosa

<400> SEQUENCE: 29

| atggctgtgg aggttcaccg ccgggctccc gcgcccatg gccggggcac cggggagaag | 60 |
| ggccgcgtgc aggccgggga cgcgctgccg ctgccgatcc gccacaccaa cctcatcttc | 120 |

```
tcggcgctct tcgccgcctc cctcgcatac ctcatgcgcc gctggaggga aagatccgc       180 aactccacgc cgctccacgt cgtggggctc accgagatct tcgccatctg cggcctcgtc       240
gcctccctca tctacctcct cagcttcttc ggcatcgcct tcgtgcagtc cgtcgtatcc       300
aacagcgacg acgaggacga ggacttcctc atcgcggctg cagcatccca ggcccccccg       360
ccgccctcct ccaagcccgc gccgcagcag tgcgccctgc tgcagagcgc cggagtcgcg       420
cccgagaaaa tgcccgagga ggacgaggaa atcgtcgccg ggtcgtcgc agggaagatc        480 ccctcctacg tgctcgagac caggctaggc gactgccgca gggcagccgg gatccgccgc       540
gaggcgctgc gccggatcac cggcaggag atcgacggcc ttccctcga cggcttcgac         600 tacgactcga ttctcggaca gtgctgcgag atgcccgtcg ggtacgtgca gctgccggtc       660
ggcgtcgcgg ggccgctcgt cctcgacggc cgccgcatat acgtcccgat ggccaccacg       720
gagggctgcc taatcgccag caccaaccgc ggatgcaagg ccattgccga gtccggaggc       780
gcatccagcg tcgtgtaccg cgacgggatg accgcgcccc cgtagcccg cttcccctcc        840 gcacgacgcg ccgcagagct caagggcttc ctggagaatc cggccaacta cgacaccctg       900
tccgtggtct ttaacagatc aagcagattt gcaaggctgc aggggtcaa gtgcgccatg       960 gctgggagga acttgtacat gaggttcacc tgcagcaccg gggatgccat ggggatgaac       1020
atggtctcca agggcgtcca aaatgtgctc gactatctgc aggaggactt ccctgacatg       1080
gacgttgtca gcatctcagg caacttttgt tccgacaaga atcagctgc tgtaaactgg        1140 attgaaggcc gtggaaagtc cgtggtttgt gaggcagtaa tcagagagga agttgtccac       1200
aaggttctca agaccaacgt tcagtcactc gtggagttga atgtgatcaa gaaccttgct      1260
ggctcagcag ttgctggtgc tcttgggggt ttcaacgccc acgcaagcaa catcgtaacg      1320
gctatcttca ttgccactgg tcaggatcct gcacagaatg tggagagctc acagtgtatc      1380
actatgttgg aagctgtaaa tgatggcaga gaccttcaca tctccgttac aatgccatct     1440
atcgaggtgg gcacagttgg tggaggcacg cagctggcct cacagtcggc ctgcttggac      1500
ctactgggcg tcaaaggcgc caacagggaa tctccggggt cgaacgctag gctgctggcc      1560
acggtggtgg ctggtgccgt cctagctggg gagctgtccc tcatctccgc caagctgcc       1620 ggccatctgg tccagagcca catgaaatac aacagatcca gcaaggacat gtccaagatc       1680
gcctgctga                                                                 1689
```

<210> SEQ ID NO 30
<211> LENGTH: 562
<212> TYPE: PRT
<213> ORGANISM: Avena strigosa

<400> SEQUENCE: 30

```
Met Ala Val Glu Val His Arg Arg Ala Pro Ala Pro His Gly Arg Gly
1               5                   10                  15

Thr Gly Glu Lys Gly Arg Val Gln Ala Gly Asp Ala Leu Pro Leu Pro
            20                  25                  30

Ile Arg His Thr Asn Leu Ile Phe Ser Ala Leu Phe Ala Ala Ser Leu
        35                  40                  45

Ala Tyr Leu Met Arg Arg Trp Arg Glu Lys Ile Arg Asn Ser Thr Pro
    50                  55                  60

Leu His Val Val Gly Leu Thr Glu Ile Phe Ala Ile Cys Gly Leu Val
65                  70                  75                  80

Ala Ser Leu Ile Tyr Leu Leu Ser Phe Phe Gly Ile Ala Phe Val Gln
```

-continued

```
                85                  90                  95

Ser Val Val Ser Asn Ser Asp Asp Glu Asp Glu Asp Phe Leu Ile Ala
            100                 105                 110

Ala Ala Ala Ser Gln Ala Pro Pro Pro Ser Ser Lys Pro Ala Pro
            115                 120                 125

Gln Gln Cys Ala Leu Leu Gln Ser Ala Gly Val Ala Pro Glu Lys Met
130                 135                 140

Pro Glu Glu Asp Glu Glu Ile Val Ala Gly Val Val Ala Gly Lys Ile
145                 150                 155                 160

Pro Ser Tyr Val Leu Glu Thr Arg Leu Gly Asp Cys Arg Arg Ala Ala
                165                 170                 175

Gly Ile Arg Arg Glu Ala Leu Arg Arg Ile Thr Gly Arg Glu Ile Asp
            180                 185                 190

Gly Leu Pro Leu Asp Gly Phe Asp Tyr Asp Ser Ile Leu Gly Gln Cys
            195                 200                 205

Cys Glu Met Pro Val Gly Tyr Val Gln Leu Pro Val Gly Val Ala Gly
            210                 215                 220

Pro Leu Val Leu Asp Gly Arg Arg Ile Tyr Val Pro Met Ala Thr Thr
225                 230                 235                 240

Glu Gly Cys Leu Ile Ala Ser Thr Asn Arg Gly Cys Lys Ala Ile Ala
                245                 250                 255

Glu Ser Gly Gly Ala Ser Ser Val Val Tyr Arg Asp Gly Met Thr Arg
            260                 265                 270

Ala Pro Val Ala Arg Phe Pro Ser Ala Arg Ala Ala Glu Leu Lys
            275                 280                 285

Gly Phe Leu Glu Asn Pro Ala Asn Tyr Asp Thr Leu Ser Val Val Phe
            290                 295                 300

Asn Arg Ser Ser Arg Phe Ala Arg Leu Gln Gly Val Lys Cys Ala Met
305                 310                 315                 320

Ala Gly Arg Asn Leu Tyr Met Arg Phe Thr Cys Ser Thr Gly Asp Ala
                325                 330                 335

Met Gly Met Asn Met Val Ser Lys Gly Val Gln Asn Val Leu Asp Tyr
            340                 345                 350

Leu Gln Glu Asp Phe Pro Asp Met Asp Val Val Ser Ile Ser Gly Asn
            355                 360                 365

Phe Cys Ser Asp Lys Lys Ser Ala Ala Val Asn Trp Ile Glu Gly Arg
            370                 375                 380

Gly Lys Ser Val Val Cys Glu Ala Val Ile Arg Glu Glu Val His
385                 390                 395                 400

Lys Val Leu Lys Thr Asn Val Gln Ser Leu Val Glu Leu Asn Val Ile
                405                 410                 415

Lys Asn Leu Ala Gly Ser Ala Val Ala Gly Ala Leu Gly Gly Phe Asn
            420                 425                 430

Ala His Ala Ser Asn Ile Val Thr Ala Ile Phe Ile Ala Thr Gly Gln
            435                 440                 445

Asp Pro Ala Gln Asn Val Glu Ser Ser Gln Cys Ile Thr Met Leu Glu
            450                 455                 460

Ala Val Asn Asp Gly Arg Asp Leu His Ile Ser Val Thr Met Pro Ser
465                 470                 475                 480

Ile Glu Val Gly Thr Val Gly Gly Thr Gln Leu Ala Ser Gln Ser
                485                 490                 495

Ala Cys Leu Asp Leu Leu Gly Val Lys Gly Ala Asn Arg Glu Ser Pro
            500                 505                 510
```

Gly Ser Asn Ala Arg Leu Leu Ala Thr Val Val Ala Gly Ala Val Leu
            515                 520                 525

Ala Gly Glu Leu Ser Leu Ile Ser Ala Gln Ala Gly His Leu Val
        530                 535                 540

Gln Ser His Met Lys Tyr Asn Arg Ser Ser Lys Asp Met Ser Lys Ile
545                 550                 555                 560

Ala Cys

<210> SEQ ID NO 31
<211> LENGTH: 1275
<212> TYPE: DNA
<213> ORGANISM: Avena strigosa

<400> SEQUENCE: 31

```
atggcgcccg agaaaatgcc cgaggaggac gaggaaatcg tcgccggggt cgtcgcaggg      60
aagatcccct cctacgtgct cgagaccagg ctaggcgact gccgcagggc agccgggatc     120
cgccgcgagg cgctgcgccg gatcaccggc agggagatca cggccttcc cctcgacggc     180
ttcgactacg actcgattct cggacagtgc tgcgagatgc ccgtcgggta cgtgcagctg     240
ccggtcggcg tcgcggggcc gctcgtcctc gacggccgcc gcatatacgt cccgatggcc     300
accacggagg gctgcctaat cgccagcacc aaccgcggat gcaaggccat tgccgagtcc     360
ggaggcgcat ccagcgtcgt gtaccgcgac gggatgaccc gcgcccccgt agcccgcttc     420
ccctccgcac gacgcgccgc agagctcaag ggcttcctgg agaatccggc caactacgac     480
accctgtccg tggtctttaa cagatcaagc agatttgcaa ggctgcaggg ggtcaagtgc     540
gccatggctg ggaggaactt gtacatgagg ttcacctgca gcaccgggga tgccatgggg     600
atgaacatgg tctccaaggg cgtccaaaat gtgctcgact atctgcagga ggacttccct     660
gacatggacg ttgtcagcat ctcaggcaac ttttgttccg acaagaaatc agctgctgta     720
aactggattg aaggccgtgg aaagtccgtg gtttgtgagg cagtaatcag agaggaagtt     780
gtccacaagg ttctcaagac caacgttcag tcactcgtgg agttgaatgt gatcaagaac     840
cttgctggct cagcagttgc tggtgctctt gggggtttca acgccacgc aagcaacatc     900
gtaacggcta tcttcattgc cactggtcag atcctgcac agaatgtgga gagctcacag     960
tgtatcacta tgttggaagc tgtaaatgat ggcagagacc ttcacatctc cgttacaatg    1020
ccatctatcg aggtgggcac agttggtgga ggcacgcagc tggcctcaca gtcggcctgc    1080
ttggacctac tgggcgtcaa aggcgccaac agggaatctc cggggtcgaa cgctaggctg    1140
ctggccacgg tggtggctgg tgccgtccta gctggggagc tgtccctcat ctccgcccaa    1200
gctgccggcc atctggtcca gagccacatg aaatacaaca gatccagcaa ggacatgtcc    1260
aagatcgcct gctga                                                     1275
```

<210> SEQ ID NO 32
<211> LENGTH: 424
<212> TYPE: PRT
<213> ORGANISM: Avena strigosa

<400> SEQUENCE: 32

Met Ala Pro Glu Lys Met Pro Glu Glu Asp Glu Glu Ile Val Ala Gly
1               5                  10                  15

Val Val Ala Gly Lys Ile Pro Ser Tyr Val Leu Glu Thr Arg Leu Gly
            20                  25                  30

Asp Cys Arg Arg Ala Ala Gly Ile Arg Arg Glu Ala Leu Arg Arg Ile

```
            35                  40                  45
Thr Gly Arg Glu Ile Asp Gly Leu Pro Leu Asp Gly Phe Asp Tyr Asp
 50                  55                  60
Ser Ile Leu Gly Gln Cys Cys Glu Met Pro Val Gly Tyr Val Gln Leu
 65                  70                  75                  80
Pro Val Gly Val Ala Gly Pro Leu Val Leu Asp Gly Arg Arg Ile Tyr
                 85                  90                  95
Val Pro Met Ala Thr Thr Glu Gly Cys Leu Ile Ala Ser Thr Asn Arg
                100                 105                 110
Gly Cys Lys Ala Ile Ala Glu Ser Gly Ala Ser Val Val Tyr
                115                 120                 125
Arg Asp Gly Met Thr Arg Ala Pro Val Ala Arg Phe Pro Ser Ala Arg
                130                 135                 140
Arg Ala Ala Glu Leu Lys Gly Phe Leu Glu Asn Pro Ala Asn Tyr Asp
145                 150                 155                 160
Thr Leu Ser Val Val Phe Asn Arg Ser Ser Arg Phe Ala Arg Leu Gln
                165                 170                 175
Gly Val Lys Cys Ala Met Ala Gly Arg Asn Leu Tyr Met Arg Phe Thr
                180                 185                 190
Cys Ser Thr Gly Asp Ala Met Gly Met Asn Met Val Ser Lys Gly Val
                195                 200                 205
Gln Asn Val Leu Asp Tyr Leu Gln Glu Asp Phe Pro Asp Met Asp Val
210                 215                 220
Val Ser Ile Ser Gly Asn Phe Cys Ser Asp Lys Lys Ser Ala Ala Val
225                 230                 235                 240
Asn Trp Ile Glu Gly Arg Gly Lys Ser Val Val Cys Glu Ala Val Ile
                245                 250                 255
Arg Glu Glu Val Val His Lys Val Leu Lys Thr Asn Val Gln Ser Leu
                260                 265                 270
Val Glu Leu Asn Val Ile Lys Asn Leu Ala Gly Ser Ala Val Ala Gly
                275                 280                 285
Ala Leu Gly Gly Phe Asn Ala His Ala Ser Asn Ile Val Thr Ala Ile
                290                 295                 300
Phe Ile Ala Thr Gly Gln Asp Pro Ala Gln Asn Val Glu Ser Ser Gln
305                 310                 315                 320
Cys Ile Thr Met Leu Glu Ala Val Asn Asp Gly Arg Asp Leu His Ile
                325                 330                 335
Ser Val Thr Met Pro Ser Ile Glu Val Gly Thr Val Gly Gly Gly Thr
                340                 345                 350
Gln Leu Ala Ser Gln Ser Ala Cys Leu Asp Leu Leu Gly Val Lys Gly
                355                 360                 365
Ala Asn Arg Glu Ser Pro Gly Ser Asn Ala Arg Leu Leu Ala Thr Val
                370                 375                 380
Val Ala Gly Ala Val Leu Ala Gly Glu Leu Ser Leu Ile Ser Ala Gln
385                 390                 395                 400
Ala Ala Gly His Leu Val Gln Ser His Met Lys Tyr Asn Arg Ser Ser
                405                 410                 415
Lys Asp Met Ser Lys Ile Ala Cys
                420

<210> SEQ ID NO 33
<211> LENGTH: 1212
<212> TYPE: DNA
<213> ORGANISM: Avena strigosa
```

<400> SEQUENCE: 33

```
atgggggcgc tgtcgcggcc ggaggaggtg gtggcgctgg tcaagctgag ggtggcggcg        60
gggcagatca agcgccagat cccggccgag aacactggg ccttcgccta cgacatgctc       120
cagaaggtct cccgcagctt cgcgctcgtc atccagcagc tcggacccga actccgcaat      180
gccgtgtgca tcttctacct cgtgctccgg gccctggaca ccgtcgagga cgacaccagc      240
atccccaacg acgtgaagct gcccatcctt cgggatttct accgccatgt ctacaacccc      300
gactggcgtt attcatgtgg aacaaaccac tacaaggtgc tgatggataa gttcagactc      360
gtctccacgc ctttcctgga gctaggcgaa ggatatcaaa aggcaattga agaaatcact      420
aggcgaatgg gagcaggaat ggcaaaattt atatgccagg aggttgaaac gattgatgac      480
tataatgagt actgccacta gtagcaggg ctagtaggct atggactttc caggctcttt       540
catgctgctg gacagaaga tctggcttca gatcaacttt cgaattcaat gggtttgttt       600
cttcagaaaa ccaatataat aagggattat ttggaggata taatgagat accaaagtgc       660
cgtatgtttt ggcctcgaga aatatggagt aaatatgcag ataaacttga ggacctcaag      720
tatgaggaaa attcagaaaa agcagtgcaa tgcttgaatg atatggtgac taatgctttg      780
gtccacgccg aagactgtct tcaatacatg tctgcgttga aggataatac taattttcgg      840
ttttgtgcaa tacctcagat aatggcaatt gggacatgtg ctatttgcta caataatgtg      900
aaagtcttta gaggagttgt taagatgagg cgtgggctca ctgcacgaat aattgatgag      960
acaaaatcaa tgtcagatgt ctattctgct ttctatgagt tctcttcatt gctagagtca     1020
aagattgacg ataacgaccc aagttctgca ctaacacgga agcgtgtaga ggcaataaag     1080
aggacttgca agtcatccgg tttactaaag agaaggggat acgacctgga aaagtcaaag     1140
tataggcata tgttgatcat gcttgcactt ctgttggtgg ctattatctt cggtgtactg     1200
tacgccaagt ga                                                          1212
```

<210> SEQ ID NO 34
<211> LENGTH: 403
<212> TYPE: PRT
<213> ORGANISM: Avena strigosa

<400> SEQUENCE: 34

```
Met Gly Ala Leu Ser Arg Pro Glu Glu Val Val Ala Leu Val Lys Leu
1               5                   10                  15

Arg Val Ala Ala Gly Gln Ile Lys Arg Gln Ile Pro Ala Glu Glu His
            20                  25                  30

Trp Ala Phe Ala Tyr Asp Met Leu Gln Lys Val Ser Arg Ser Phe Ala
        35                  40                  45

Leu Val Ile Gln Gln Leu Gly Pro Glu Leu Arg Asn Ala Val Cys Ile
    50                  55                  60

Phe Tyr Leu Val Leu Arg Ala Leu Asp Thr Val Glu Asp Asp Thr Ser
65                  70                  75                  80

Ile Pro Asn Asp Val Lys Leu Pro Ile Leu Arg Asp Phe Tyr Arg His
                85                  90                  95

Val Tyr Asn Pro Asp Trp Arg Tyr Ser Cys Gly Thr Asn His Tyr Lys
            100                 105                 110

Val Leu Met Asp Lys Phe Arg Leu Val Ser Thr Ala Phe Leu Glu Leu
        115                 120                 125

Gly Glu Gly Tyr Gln Lys Ala Ile Glu Glu Ile Thr Arg Arg Met Gly
    130                 135                 140
```

Ala Gly Met Ala Lys Phe Ile Cys Gln Glu Val Glu Thr Ile Asp Asp
145                 150                 155                 160

Tyr Asn Glu Tyr Cys His Tyr Val Ala Gly Leu Val Gly Tyr Gly Leu
            165                 170                 175

Ser Arg Leu Phe His Ala Ala Gly Thr Glu Asp Leu Ala Ser Asp Gln
        180                 185                 190

Leu Ser Asn Ser Met Gly Leu Phe Leu Gln Lys Thr Asn Ile Ile Arg
        195                 200                 205

Asp Tyr Leu Glu Asp Ile Asn Glu Ile Pro Lys Cys Arg Met Phe Trp
210                 215                 220

Pro Arg Glu Ile Trp Ser Lys Tyr Ala Asp Lys Leu Glu Asp Leu Lys
225                 230                 235                 240

Tyr Glu Glu Asn Ser Glu Lys Ala Val Gln Cys Leu Asn Asp Met Val
                245                 250                 255

Thr Asn Ala Leu Val His Ala Glu Asp Cys Leu Gln Tyr Met Ser Ala
            260                 265                 270

Leu Lys Asp Asn Thr Asn Phe Arg Phe Cys Ala Ile Pro Gln Ile Met
        275                 280                 285

Ala Ile Gly Thr Cys Ala Ile Cys Tyr Asn Asn Val Lys Val Phe Arg
        290                 295                 300

Gly Val Val Lys Met Arg Arg Gly Leu Thr Ala Arg Ile Ile Asp Glu
305                 310                 315                 320

Thr Lys Ser Met Ser Asp Val Tyr Ser Ala Phe Tyr Glu Phe Ser Ser
                325                 330                 335

Leu Leu Glu Ser Lys Ile Asp Asp Asn Asp Pro Ser Ser Ala Leu Thr
                340                 345                 350

Arg Lys Arg Val Glu Ala Ile Lys Arg Thr Cys Lys Ser Ser Gly Leu
            355                 360                 365

Leu Lys Arg Arg Gly Tyr Asp Leu Glu Lys Ser Lys Tyr Arg His Met
        370                 375                 380

Leu Ile Met Leu Ala Leu Leu Val Ala Ile Ile Phe Gly Val Leu
385                 390                 395                 400

Tyr Ala Lys

<210> SEQ ID NO 35
<211> LENGTH: 2325
<212> TYPE: DNA
<213> ORGANISM: Arabidopsis thaliana

<400> SEQUENCE: 35

```
atgaaaaaca tgatgaatta taaattaaaa ctctgttctg tctcaaaaaa ctcaaaagga      60
gtctctctct cacctacacc acacctaacc aaacccccta cgattcacac agagagagat     120
cttcttcttc cttcttcttc cttcttcttt cttcttcttt cttcttctag ctacaacatc     180
tacaacgcca tgtcctcttc ttcttcttcg tcaacctcca tgatcgatct catggcagca     240
atcatcaaag gagagcctgt aattgtctcc gacccagcta atgcctccgc ttacgagtcc     300
gtagctgctg aattatcctc tatgcttata gagaatcgtc aattcgccat gattgttacc     360
acttccattg ctgttcttat tggttgcatc gttatgctcg tttggaggag atccggttct     420
gggaattcaa acgtgtcgac gcctcttaag cctttggtta ttaagcctcg tgaggaagag     480
attgatgatg gcgtaagaa agttaccatc tttttcggta cacaaactgg tactgctgaa     540
ggttttgcaa aggctttagg agaagaagct aaagcaagat atgaaaagac cagattcaaa     600
```

| | |
|---|---|
| atcgttgatt tggatgatta cgcggctgat gatgatgagt atgaggagaa attgaagaaa | 660 |
| gaggatgtgg ctttcttctt cttagccaca tatggagatg gtgagcctac cgacaatgca | 720 |
| gcgagattct acaaatggtt caccgagggg aatgacagag gagaatggct taagaacttg | 780 |
| aagtatggag tgtttggatt aggaaacaga caatatgagc attttaataa ggttgccaaa | 840 |
| gttgtagatg acattcttgt cgaacaaggt gcacagcgtc ttgtacaagt tggtcttgga | 900 |
| gatgatgacc agtgtattga agatgacttt accgcttggc gagaagcatt gtggcccgag | 960 |
| cttgatacaa tactgaggga agaaggggat acagctgttg ccacaccata cactgcagct | 1020 |
| gtgttagaat acagagtttc tattcacgac tctgaagatg ccaaattcaa tgatataaac | 1080 |
| atggcaaatg ggaatggtta cactgtgttt gatgctcaac atccttacaa agcaaatgtc | 1140 |
| gctgttaaaa gggagcttca tactcccgag tctgatcgtt cttgtatcca tttggaattt | 1200 |
| gacattgctg gaagtggact tacgtatgaa actggagatc atgttggtgt actttgtgat | 1260 |
| aacttaagtg aaactgtaga tgaagctctt agattgctgg atatgtcacc tgatacttat | 1320 |
| ttctcacttc acgctgaaaa agaagacggc acaccaatca gcagctcact gcctcctccc | 1380 |
| ttcccacctt gcaacttgag aacagcgctt acacgatatg catgtctttt gagttctcca | 1440 |
| aagaagtctg ctttagttgc gttggctgct catgcatctg atcctaccga agcagaacga | 1500 |
| ttaaaacacc ttgcttcacc tgctggaaag gatgaatatt caaagtgggt agtagagagt | 1560 |
| caaagaagtc tacttgaggt gatggccgag tttccttcag ccaagccacc acttggtgtc | 1620 |
| ttcttcgctg gagttgctcc aaggttgcag cctaggttct attcgatatc atcatcgccc | 1680 |
| aagattgctg aaactagaat tcacgtcaca tgtgcactgg tttatgagaa atgccaact | 1740 |
| ggcaggattc ataagggagt gtgttccact tggatgaaga atgctgtgcc ttacgagaag | 1800 |
| agtgaaaact gttcctcggc gccgatattt gttaggcaat ccaacttcaa gcttccttct | 1860 |
| gattctaagg taccgatcat catgatcggt ccagggactg gattagctcc attcagagga | 1920 |
| ttccttcagg aaagactagc gttggtagaa tctggtgttg aacttgggcc atcagttttg | 1980 |
| ttctttggat gcagaaaccg tagaatggat ttcatctacg aggaagagct ccagcgattt | 2040 |
| gttgagagtg tgctctcgc agagctaagt gtcgccttct ctcgtgaagg acccaccaaa | 2100 |
| gaatacgtac agcacaagat gatggacaag gcttctgata tctggaatat gatctctcaa | 2160 |
| ggagcttatt tatatgtttg tggtgacgcc aaaggcatgg caagagatgt tcacagatct | 2220 |
| ctccacacaa tagctcaaga acaggggtca atggattcaa ctaaagcaga gggcttcgtg | 2280 |
| aagaatctgc aaacgagtgg aagatatctt agagatgtat ggtaa | 2325 |

<210> SEQ ID NO 36
<211> LENGTH: 774
<212> TYPE: PRT
<213> ORGANISM: Arabidopsis thaliana

<400> SEQUENCE: 36

Met Lys Asn Met Met Asn Tyr Lys Leu Lys Leu Cys Ser Val Ser Lys
1               5                   10                  15

Asn Ser Lys Gly Val Ser Leu Ser Pro Thr Pro His Leu Thr Lys Pro
            20                  25                  30

Pro Thr Ile His Thr Glu Arg Asp Leu Leu Pro Ser Ser Ser Phe
        35                  40                  45

Phe Phe Leu Leu Leu Ser Ser Ser Ser Tyr Asn Ile Tyr Asn Ala Met
    50                  55                  60

Ser Ser Ser Ser Ser Ser Ser Thr Ser Met Ile Asp Leu Met Ala Ala

-continued

```
         65                  70                  75                  80
Ile Ile Lys Gly Glu Pro Val Ile Val Ser Asp Pro Ala Asn Ala Ser
                 85                  90                  95

Ala Tyr Glu Ser Val Ala Ala Glu Leu Ser Ser Met Leu Ile Glu Asn
                100                 105                 110

Arg Gln Phe Ala Met Ile Val Thr Thr Ser Ile Ala Val Leu Ile Gly
                115                 120                 125

Cys Ile Val Met Leu Val Trp Arg Arg Ser Gly Ser Gly Asn Ser Lys
130                 135                 140

Arg Val Glu Pro Leu Lys Pro Leu Val Ile Lys Pro Arg Glu Glu Glu
145                 150                 155                 160

Ile Asp Asp Gly Arg Lys Lys Val Thr Ile Phe Phe Gly Thr Gln Thr
                165                 170                 175

Gly Thr Ala Glu Gly Phe Ala Lys Ala Leu Gly Glu Glu Ala Lys Ala
                180                 185                 190

Arg Tyr Glu Lys Thr Arg Phe Lys Ile Val Asp Leu Asp Asp Tyr Ala
                195                 200                 205

Ala Asp Asp Asp Glu Tyr Glu Glu Lys Leu Lys Lys Glu Asp Val Ala
210                 215                 220

Phe Phe Phe Leu Ala Thr Tyr Gly Asp Gly Glu Pro Thr Asp Asn Ala
225                 230                 235                 240

Ala Arg Phe Tyr Lys Trp Phe Thr Glu Gly Asn Asp Arg Gly Glu Trp
                245                 250                 255

Leu Lys Asn Leu Lys Tyr Gly Val Phe Gly Leu Gly Asn Arg Gln Tyr
                260                 265                 270

Glu His Phe Asn Lys Val Ala Lys Val Val Asp Asp Ile Leu Val Glu
                275                 280                 285

Gln Gly Ala Gln Arg Leu Val Gln Val Gly Leu Gly Asp Asp Asp Gln
                290                 295                 300

Cys Ile Glu Asp Asp Phe Thr Ala Trp Arg Glu Ala Leu Trp Pro Glu
305                 310                 315                 320

Leu Asp Thr Ile Leu Arg Glu Glu Gly Asp Thr Ala Val Ala Thr Pro
                325                 330                 335

Tyr Thr Ala Ala Val Leu Glu Tyr Arg Val Ser Ile His Asp Ser Glu
                340                 345                 350

Asp Ala Lys Phe Asn Asp Ile Asn Met Ala Asn Gly Asn Gly Tyr Thr
                355                 360                 365

Val Phe Asp Ala Gln His Pro Tyr Lys Ala Asn Val Ala Val Lys Arg
                370                 375                 380

Glu Leu His Thr Pro Glu Ser Asp Arg Ser Cys Ile His Leu Glu Phe
385                 390                 395                 400

Asp Ile Ala Gly Ser Gly Leu Thr Tyr Glu Thr Gly Asp His Val Gly
                405                 410                 415

Val Leu Cys Asp Asn Leu Ser Glu Thr Val Asp Glu Ala Leu Arg Leu
                420                 425                 430

Leu Asp Met Ser Pro Asp Thr Tyr Phe Ser Leu His Ala Glu Lys Glu
                435                 440                 445

Asp Gly Thr Pro Ile Ser Ser Ser Leu Pro Pro Pro Phe Pro Pro Cys
                450                 455                 460

Asn Leu Arg Thr Ala Leu Thr Arg Tyr Ala Cys Leu Leu Ser Ser Pro
465                 470                 475                 480

Lys Lys Ser Ala Leu Val Ala Leu Ala Ala His Ala Ser Asp Pro Thr
                485                 490                 495
```

```
Glu Ala Glu Arg Leu Lys His Leu Ala Ser Pro Ala Gly Lys Asp Glu
            500                 505                 510

Tyr Ser Lys Trp Val Val Glu Ser Gln Arg Ser Leu Leu Glu Val Met
            515                 520                 525

Ala Glu Phe Pro Ser Ala Lys Pro Pro Leu Gly Val Phe Phe Ala Gly
            530                 535                 540

Val Ala Pro Arg Leu Gln Pro Arg Phe Tyr Ser Ile Ser Ser Ser Pro
545                 550                 555                 560

Lys Ile Ala Glu Thr Arg Ile His Val Thr Cys Ala Leu Val Tyr Glu
                565                 570                 575

Lys Met Pro Thr Gly Arg Ile His Lys Gly Val Cys Ser Thr Trp Met
                580                 585                 590

Lys Asn Ala Val Pro Tyr Glu Lys Ser Glu Asn Cys Ser Ser Ala Pro
                595                 600                 605

Ile Phe Val Arg Gln Ser Asn Phe Lys Leu Pro Ser Asp Ser Lys Val
            610                 615                 620

Pro Ile Ile Met Ile Gly Pro Gly Thr Gly Leu Ala Pro Phe Arg Gly
625                 630                 635                 640

Phe Leu Gln Glu Arg Leu Ala Leu Val Glu Ser Gly Val Glu Leu Gly
                645                 650                 655

Pro Ser Val Leu Phe Phe Gly Cys Arg Asn Arg Arg Met Asp Phe Ile
                660                 665                 670

Tyr Glu Glu Glu Leu Gln Arg Phe Val Glu Ser Gly Ala Leu Ala Glu
            675                 680                 685

Leu Ser Val Ala Phe Ser Arg Glu Gly Pro Thr Lys Glu Tyr Val Gln
            690                 695                 700

His Lys Met Met Asp Lys Ala Ser Asp Ile Trp Asn Met Ile Ser Gln
705                 710                 715                 720

Gly Ala Tyr Leu Tyr Val Cys Gly Asp Ala Lys Gly Met Ala Arg Asp
                725                 730                 735

Val His Arg Ser Leu His Thr Ile Ala Gln Glu Gln Gly Ser Met Asp
                740                 745                 750

Ser Thr Lys Ala Glu Gly Phe Val Lys Asn Leu Gln Thr Ser Gly Arg
            755                 760                 765

Tyr Leu Arg Asp Val Trp
    770
```

<210> SEQ ID NO 37
<211> LENGTH: 57
<212> TYPE: DNA
<213> ORGANISM: Artificial Sequence
<220> FEATURE:
<223> OTHER INFORMATION: Synthetic Oligonucleotide Primer QsbAS1_F

<400> SEQUENCE: 37
ggggacaagt ttgtacaaaa aagcaggctt aatgtggagg ctgaagatag cagaagg    57

<210> SEQ ID NO 38
<211> LENGTH: 53
<212> TYPE: DNA
<213> ORGANISM: Artificial Sequence
<220> FEATURE:
<223> OTHER INFORMATION: Synthetic Oligonucleotide Primer QsbAS1_R

<400> SEQUENCE: 38
ggggaccact ttgtacaaga aagctgggta ttaaggcaat ggaacccgcc tcc    53

```
<210> SEQ ID NO 39
<211> LENGTH: 62
<212> TYPE: DNA
<213> ORGANISM: Artificial Sequence
<220> FEATURE:
<223> OTHER INFORMATION: Synthetic Oligonucleotide Primer
      QsCYP716_2012090L_F

<400> SEQUENCE: 39 gggacaagt tgtacaaaaa aagcaggctt aatgatatat aataatgata gtaatgataa    60
tg                                                                  62

<210> SEQ ID NO 40
<211> LENGTH: 55
<212> TYPE: DNA
<213> ORGANISM: Artificial Sequence
<220> FEATURE:
<223> OTHER INFORMATION: Synthetic Oligonucleotide Primer
      QsCYP716_2012090S_F

<400> SEQUENCE: 40 gggacaagt tgtacaaaaa aagcaggctt aatggatcct ttcttcattt ttggc          55

<210> SEQ ID NO 41
<211> LENGTH: 48
<212> TYPE: DNA
<213> ORGANISM: Artificial Sequence
<220> FEATURE:
<223> OTHER INFORMATION: Synthetic Oligonucleotide Primer
      QsCYP716_2012090_R

<400> SEQUENCE: 41
ggggaccact tgtacaaga aagctgggta tcattggtgc ttgtgagg                  48

<210> SEQ ID NO 42
<211> LENGTH: 58
<212> TYPE: DNA
<213> ORGANISM: Artificial Sequence
<220> FEATURE:
<223> OTHER INFORMATION: Synthetic Oligonucleotide Primer
      QsCYP716_2073932_F

<400> SEQUENCE: 42 gggacaagt tgtacaaaaa aagcaggctt aatggagcac ttgtatctct cccttgtg      58

<210> SEQ ID NO 43
<211> LENGTH: 57
<212> TYPE: DNA
<213> ORGANISM: Artificial Sequence
<220> FEATURE:
<223> OTHER INFORMATION: Synthetic Oligonucleotide Primer
      QsCYP716_2073932_R

<400> SEQUENCE: 43
ggggaccact tgtacaaga aagctgggta tcaagctttg tgaggataaa ggcgaac       57

<210> SEQ ID NO 44
<211> LENGTH: 53
<212> TYPE: DNA
<213> ORGANISM: Artificial Sequence
<220> FEATURE:
<223> OTHER INFORMATION: Synthetic Oligonucleotide Primer
      QsCYP714_2018687_F

<400> SEQUENCE: 44 gggacaagt tgtacaaaaa aagcaggctt aatgtggttc acagtaggat tgg           53
```

```
<210> SEQ ID NO 45
<211> LENGTH: 55
<212> TYPE: DNA
<213> ORGANISM: Artificial Sequence
<220> FEATURE:
<223> OTHER INFORMATION: Synthetic Oligonucleotide Primer
      QsCYP714_2018687 R

<400> SEQUENCE: 45
ggggaccact tgtacaaga aagctgggta ttagagcttc ttcatgatga cattg          55
```